United States Patent
Goodnow, Jr. et al.

(10) Patent No.: US 9,650,363 B2
(45) Date of Patent: May 16, 2017

(54) INTEGRIN ANTAGONIST CONJUGATES FOR TARGETED DELIVERY TO CELLS EXPRESSING LFA-1

(71) Applicant: Hoffmann-La Roche Inc., Nutley, NJ (US)

(72) Inventors: Robert Alan Goodnow, Jr., Gillette, NJ (US); Matthew Michael Hamilton, Hackettstown, NJ (US); Agnieszka Kowalczyk, Mine Hill, NJ (US); Achyutharao Sidduri, West Orange, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/373,989

(22) PCT Filed: Jan. 24, 2013

(86) PCT No.: PCT/EP2013/051273
§ 371 (c)(1),
(2) Date: Jul. 23, 2014

(87) PCT Pub. No.: WO2013/110679
PCT Pub. Date: Aug. 1, 2013

(65) Prior Publication Data
US 2015/0065534 A1 Mar. 5, 2015

Related U.S. Application Data

(60) Provisional application No. 61/591,297, filed on Jan. 27, 2012, provisional application No. 61/678,673, filed on Aug. 2, 2012.

(51) Int. Cl.
| | | |
|---|---|---|
| *C07D 403/12* | (2006.01) | |
| *C07C 327/06* | (2006.01) | |
| *C07D 207/46* | (2006.01) | |
| *C07D 213/71* | (2006.01) | |
| *C07H 21/02* | (2006.01) | |
| *A61K 47/48* | (2006.01) | |
| *C07C 381/00* | (2006.01) | |
| *C07D 207/36* | (2006.01) | |

(52) U.S. Cl.
CPC ...... *C07D 403/12* (2013.01); *A61K 47/48023* (2013.01); *A61K 47/48061* (2013.01); *C07C 327/06* (2013.01); *C07C 381/00* (2013.01); *C07D 207/36* (2013.01); *C07D 207/46* (2013.01); *C07D 213/71* (2013.01); *C07H 21/02* (2013.01)

(58) Field of Classification Search
CPC .. C07D 403/12; C07D 207/36; C07D 207/46; C07D 213/71; C07C 327/06; C07C 381/00; C07H 21/02; A61K 47/48023; A61K 47/48061
See application file for complete search history.

(56) References Cited

U.S. PATENT DOCUMENTS

| | | | | |
|---|---|---|---|---|
| 6,229,011 B1* | 5/2001 | Chen | ..................... | C07C 233/87 544/171 |
| 2012/0270875 A1* | 10/2012 | Gillespie | .............. | C07D 239/42 514/235.8 |
| 2013/0197059 A1* | 8/2013 | Goodnow, Jr. | ........ | C07C 327/06 514/44 A |
| 2015/0038523 A1* | 2/2015 | Goodnow, Jr. | .. | A61K 47/48061 514/275 |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
H.A. Fine, Neoplasms of the Central Nervous System in, 2 Cancer Principles & Practice of Oncology 1834-1887 (V.T. DeVita, Jr. et al. eds., 5th ed., 2005).*
D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*

(Continued)

*Primary Examiner* — Alexander R Pagano

(57) ABSTRACT

The invention relates to compounds of formula (I), wherein R1, R2, and n are defined in the detailed description and claims. In particular, the present invention relates to the compounds of formula I for use in the manufacture and delivery of conjugated moieties such as small molecules, peptides, nucleic acids, fluorescent moieties, and polymers which are linked to LFA-1 integrin antagonists to target cells expressing LFA-1.

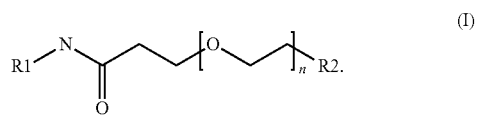

(I)

62 Claims, 20 Drawing Sheets

(56) References Cited

OTHER PUBLICATIONS

Fogarty et al., 1804 Biochimica et Biophysica Acta, 581-591 (2010).*
S Hariharan et al., 18 Annals of Oncology, 1400-1407 (2006).*
R. Max et al., 71 International Journal of Cancer, 320-324 (1997).*
X. Duan et al., 21 Clinical & Experimental Metastasis, 747-753 (2004).*
A. Abdollahi et al., 11 Clinical Cancer Research, 6270-6279 (2005).*
A.J. Lyons et al., 34 International Journal of Oral and Maxillofacial Surgery, 912-914 (2005).*
M. Rolli et al., 100 PNAS, 9482-9487 (2003).*
N. Reinmuth et al., 63 Cancer Research, 2079-2087 (2003).*
B. Felding-Habermann, 19 Clinical & Experimental Metastasis, 427-436 (2002).*
S. Takayama et al., 25 Anticancer Research, 79-84 (2005).*
M. Lorger et al., 106 PNAS, 10666-10671 (2009).*
N.J. Kenyon et al., 603 European Journal of Pharmacology 138-146 (2009).*
C.C. Feral et al., 57 Diabetes, 1842-1851 (2008).*

* cited by examiner

Table 1: Summaries of the composition of 5'-derivatized siRNA single and double strands

| Duplex -ID | Sense -ID | Sequence 5'-->3' | Antisense -ID | Sequence 5'-->3' |
|---|---|---|---|---|
| Duplex -1 | Sense -1 | GGAuGAAGuGGAGAuuAGu dTsdT (SEQ ID NO.1) | Antisense -1 | ACuAAUCUCcACUUcAUC CdTsdT (SEQ ID NO.2) |
| Duplex -2 | Sense -2 | LFA-1 Ligand Reagent 1-(SC6)GGAuGAAGuGGAGAu uAGudTsdT | Antisense -1 | ACuAAUCUCcACUUcAUC CdTsdT |
| Duplex -3 | Sense -3 | LFA-1 Ligand Reagent 3-(SC6)GGAuGAAGuGGAGAu uAGudTsdT | Antisense -1 | ACuAAUCUCcACUUcAUC CdTsdT |
| Duplex -8 | Sense -8 | LFA-1 Ligand Reagent 6-(SC6)GGAuGAAGuGGAGAu uAGudTsdT | Antisense -1 | ACuAAUCUCcACUUcAUC CdTsdT |
| Duplex -9 | Sense -9 | LFA-1 Ligand Reagent 5-(SC6)GGAuGAAGuGGAGAu uAGudTsdT | Antisense -1 | ACuAAUCUCcACUUcAUC CdTsdT |

Fig. 1A

| Duplex -ID | Sense -ID | Sequence 5'-->3' | Antisense -ID | Sequence 5'-->3' |
|---|---|---|---|---|
| Duplex -10 | Sense -10 | LFA-1 Ligand Reagent 4-(SC6)GGAuGAAGuGGAGAuuAGudTsdT | Antisense -1 | ACuAAUCUCcACUUcAUCCdTsdT |
| Duplex -19 | Sense -19 | LFA-1 Ligand Reagent 8-(SC6)GGAuGAAGuGGAGAuuAGudTsdT | Antisense -1 | ACuAAUCUCcACUUcAUCCdTsdT |
| Duplex -20 | Sense -20 | LFA-1 Ligand Reagent 9-(SC6)GGAuGAAGuGGAGAuuAGudTsdT | Antisense -1 | ACuAAUCUCcACUUcAUCCdTsdT |
| Duplex -21 | Sense -21 | LFA-1 Ligand Reagent 10-(SC6)GGAuGAAGuGGAGAuuAGudTsdT | Antisense -1 | ACuAAUCUCcACUUcAUCCdTsdT |

Fig. 1B

Table 2: Analytical Data for small molecule siRNA conjugates

| Small Molecule | Target | Number | Sequence (5'–3') | Calc. Mass | Exp. Mass | IEX % FLP |
|---|---|---|---|---|---|---|
| LFA-1-PEG4-maleimide | Aha1 | Sense-2 | LFA-1 Ligand Reagent 1:-(SC6)GGAuGAAGuGGAGAuuAGudTsdT | 7882.13 | 7884.8 | 86 |
| LFA-1-PEG12-maleimide | Aha1 | Sense-3 | LFA-1 Ligand Reagent 3-(SC6)GGAuGAAGuGGAGAuuAGudTsdT | 8233.84 | 8237.5 | 88.8 |
| LFA-1-PEG12-maleimide | Aha1 | Sense-8 | LFA-1 Ligand Reagent 6-(SC6)GGAuGAAGuGGAGAuuAGudTsdT | 8562.13 | 8562 | 90.9 |
| LFA-1-PEG4-maleimide | Aha1 | Sense-9 | LFA-1 Ligand Reagent 5-(SC6)GGAuGAAGuGGAGAuuAGudTsdT | 8209.7 | 8210 | 92.9 |
| LFA-1-PEG8-maleimide | Aha1 | Sense-10 | LFA-1 Ligand Reagent 4-(SC6)GGAuGAAGuGGAGAuuAGudTsdT | 8385.92 | 8386 | 93.4 |

Fig. 1C

Table 3: Summary of siRNA sequences where in the 5'-antisense strand has been derivatized with Nu547

| Duplex-ID | Sense-ID | Sequence 5'→3' | Antisense-ID | Sequence 5'→3' |
|---|---|---|---|---|
| Duplex-22 | Sense-22 | LFA-1 Ligand Reagent 1:-(SC6)GGAuGAAGuGGAGAuuAGudTsdT | Antisense-1 | (Nu547)ACuAAUCUCcACUUcAUCCdTsdT |
| Duplex-23 | Sense-23 | LFA-1 Ligand Reagent 3-(SC6)GGAuGAAGuGGAGAuuAGudTsdT | Antisense-1 | (Nu547)ACuAAUCUCcACUUcAUCCdTsdT |
| Duplex-28 | Sense-28 | LFA-1 Ligand Reagent 6-(SC6)GGAuGAAGuGGAGAuuAGudTsdT | Antisense-1 | (Nu547)ACuAAUCUCcACUUcAUCCdTsdT |
| Duplex-29 | Sense-29 | LFA-1 Ligand Reagent 5-(SC6)GGAuGAAGuGGAGAuuAGudTsdT | Antisense-1 | (Nu547)ACuAAUCUCcACUUcAUCCdTsdT |
| Duplex-30 | Sense-30 | LFA-1 Ligand Reagent 4-(SC6)GGAuGAAGuGGAGAuuAGudTsdT | Antisense-1 | (Nu547)ACuAAUCUCcACUUcAUCCdTsdT |
| Duplex-35 | Sense-35 | LFA-1 Ligand Reagent 8-(SC6)GGAuGAAGuGGAGA | Antisense-1 | (Nu547)ACuAAUCUCcACUUcAUCCdTsdT |

Fig. 1D

| Duplex-ID | Sense-ID | Sequence 5'-->3' | Antisense-ID | Sequence 5'-->3' |
|---|---|---|---|---|
| | | uuAGudTsdT | | |
| Duplex-36 | Sense-36 | LFA-1 Ligand Reagent 9-(SC6)GGAuGAAGuGGAGAuuAGudTsdT | Antisense-1 | (Nu547)ACuAAUCUCcACUUcAUCCdTsdT |
| Duplex-37 | Sense-37 | LFA-1 Ligand Reagent 10-(SC6)GGAuGAAGuGGAGAuuAGudTsdT | Antisense-1 | (Nu547)ACuAAUCUCcACUUcAUCCdTsdT |

Fig. 1E

Table 4: Summary of small molecule-siRNA conjugate potencies in integrin antagonists assays and siRNA KD data

| Targeting Element | Configuration | | | | siRNA derivative | Jurkat Cells/VCAM-1 Adhesion Assay (nM) | αVβ3 Adhesion Assay (nM) | LFA1 Adhesion Assay (nM) | AH A1 % KD |
| --- | --- | --- | --- | --- | --- | --- | --- | --- | --- |
| | Small molecule Ligand Reagent | siRNA | Duplex | Fluoro-chrome | | | | | |
| None | | AH A-1 | Duplex-1 | No | RD-03518 | >200 | | | 98 |
| None | | AH A-1 | Duplex-1N | Nu547 | RD-05170 | >200 | | | |
| LFA-1 Ligand 1-PEG 4 | LFA-1 Ligand Reagent 1 | AH A-1 | Duplex-2 | No | RD-04705 | | | 870 | 97 |
| LFA-1 Ligand 1-PEG 12 | LFA-1 Ligand Reagent 3 | AH A-1 | Duplex-3 | No | RD-04706 | >200 | | 1090 | 97 |
| LFA-1 Ligand | LFA-1 Ligand Reagent 1: | AH A-1 | Duplex-22 | Nu547 | RD-04712 | | | 700 | 4 |

Fig. 1F

| Targeting Element | Configuration | | | Fluoro-chrome | siRNA derivative | Jurkat Cells/VCAM-1 Adhesion Assay (nM) | αVβ3 Adhesion Assay (nM) | LFA1 Adhesion Assay (nM) | AH A1 % KD |
|---|---|---|---|---|---|---|---|---|---|
| | Small molecule Ligand Reagent | siRNA | | | | | | | |
| 1-PEG 4 | | | | | | | | | |
| LFA-1 Ligand 1-PEG 4 | LFA-1 Ligand Reagent 1 | AH A-1 | Duplex-23 | Nu547 | RD-04713 | | | 634 | 14 |
| LFA-1 Ligand 4-PEG 12 | LFA-1 Ligand Reagent 6 | AH A-1 | Duplex-6 | No | RD-04809 | 12 | | 192 | |
| LFA-1 Ligand 4-PEG 4 | LFA-1 Ligand Reagent 5 | AH A-1 | Duplex-7 | No | RD-04810 | 5 | | 141 | |
| LFA-1 Ligand 4-PEG 8 | LFA-1 Ligand Reagent 4 | AH A-1 | Duplex-10 | No | RD-04811 | 25 | | 80 | |
| LFA-1 Ligand 4-PEG 12 | LFA-1 Ligand Reagent 6 | AH A-1 | Duplex-28 | Nu547 | RD-04819 | 13 | | 204 | |

Fig. 1G

| Targeting Element | Configuration | | | siRNA derivative | Jurkat Cells/VCAM-1 Adhesion Assay (nM) | αVβ3 Adhesion Assay (nM) | LFA1 Adhesion Assay (nM) | AH A1 % KD |
|---|---|---|---|---|---|---|---|---|
| | Small molecule Ligand Reagent | siRNA | Fluoro-chrome | | | | | |
| LFA-1 Ligand 4-PEG 4 | LFA-1 Ligand Reagent 5 | AH A-1 | Duplex-29 | Nu547 | RD-04820 | 18 | | 117 | |
| LFA-1 Ligand 4-PEG 8 | LFA-1 Ligand Reagent 4 | AH A-1 | Duplex-31 | Nu547 | RD-04821 | 1 | | 133 | |
| LFA-1 Ligand 2-PEG 8 | LFA-1 Ligand Reagent 8 | AH A-1 | Duplex-19 | No | RD-05382 | | | 575 | |
| LFA-1 Ligand 2-PEG 8 | LFA-1 Ligand Reagent 9 | AH A-1 | Duplex-20 | No | RD-05383 | | | 391 | |
| LFA-1 Ligand 3-PEG 4 | LFA-1 Ligand Reagent 10 | AH A-1 | Duplex-21 | No | RD-05384 | | | 373 | |
| LFA-1 Ligand 3-PEG 8 | LFA-1 Ligand Reagent 8 | AH A-1 | Duplex-35 | Nu547 | RD-05425 | | | 532 | |

Fig. 1H

| Targeting Element | Configuration | | | | siRNA derivative | Jurkat Cells/VCAM-1 Adhesion Assay (nM) | αVβ3 Adhesion Assay (nM) | LFA1 Adhesion Assay (nM) | AH A1 % KD |
|---|---|---|---|---|---|---|---|---|---|
| | Small molecule Ligand Reagent | siRNA | | Fluorochrome | | | | | |
| LFA-1 Ligand 3-PEG 8 | LFA-1 Ligand Reagent 9 | AH A-1 | Duplex-36 | Nu547 | RD-05426 | | | 256 | |
| LFA-1 Ligand 3-PEG 4 | LFA-1 Ligand Reagent 10 | AH A-1 | Duplex-37 | Nu547 | RD-05427 | | | 324 | |
| LFA-1 small molecule | | | 142 | | | | | 37 | |
| LFA-1 small molecule | | | 143 | | | | | 11 | |
| Negative assay reference | | | FITC-22 | | | >200 | | | |

Fig. 11

| Targeting Element | Configuration | | | | Jurkat Cells/VCAM-1 Adhesion Assay (nM) | αVβ3 Adhesion Assay (nM) | LFA1 Adhesion Assay (nM) | AH A1 % KD |
|---|---|---|---|---|---|---|---|---|
| | Small molecule Ligand Reagent | siRNA | FITC-23 | Fluoro-chrome | siRNA derivative | | | |
| Negative assay reference | | | FITC-23 | | > 200 | | | |

Fig. 15

Table 5: Identity, characterization and binding potencies of FITC isomer labeled reagents

| Example | Targeting Element | Synthesis method: one pot or with | Jurkat Cells/VC AM-1 Adhesion | αVβ3 Assay | LFA1 Adhesion Assay | Calc. Mass | Observed Mass |
|---|---|---|---|---|---|---|---|
| | | | | | | | |

| | | corresponding targeting example | n Assay (IC50 nM) | (IC 50 nM) | (IC50 nM) | | |
|---|---|---|---|---|---|---|---|
| FITC-1 | LFA-1 Ligand 1-PEG12 | Method B (one pot) | | | 502 | 1138.27 | 1138.5761 (M+H)+ |
| FITC-2 | LFA-1 Ligand 1-1-PEG4 | Method B (one pot) | | | 134 | 786.3669 | 786.3665 [M+H]1+ |
| FITC-3 | LFA-1 Ligand 1-PEG4-FITC | Method B (one pot) | 500 | | 500 | 795.87 | 796.3357 [M+2H]2+ |
| FITC-4 | LFA-1 Ligand 1-PEG8-FITC | Method B (one pot) | 160 | | 160 | 1397.51 | 1397.5496 [M+H]+ |

Fig. 1L

| FITC-5 | LFA-1 Ligand 1-PEG4-FITC | Method B (one pot) | 340 | | | 1221.3 | 1221.4445 [M+H]+ |
|---|---|---|---|---|---|---|---|
| FITC-6 | LFA-1 Ligand 2-PEG8-opened maleimide-FITC | Method B (one pot) | | 790 | | 796.365 | 796.8230 [M+2H]2+ |
| FITC-7 | LFA-1 Ligand 3-PEG4-maleimide-FITC | Method B (one pot) | | 430 | | 707.25 | 707.7625 [M+2H]2+ |
| FITC-8 | LFA-1 Ligand 3-PEG8-opened maleimide-FITC | Method B (one pot) | | 380 | | 804.365 | 804.8212 [M+2H]2+ |
| FITC-9 | LFA-1 Ligand 4-PEG12-FITC | Method B (one pot) | 15 | | | 1900.28 | 861.7457 [M+2H]2+ |
| FITC-10 | LFA-1 Ligand 4-PEG4- | Method | 16 | | 113 | 782.9 | 782.6987 |

Fig. 1M

| | | | | |
|---|---|---|---|---|
| FITC-11 | FITC LFA-1 Ligand 4-PEG8-FITC | B (one pot) Method B (one pot) | 9 | 4 862.0 35 | [M+2H]2+ 861.7459 [M+2H]2+ |
| FITC-22 | untargeted benzyl-PEG4-FITC | Method B (one pot) | 9,400 | 43 941.0 19 | 941.3269 (M+H)+ |
| FITC-23 | untargeted benzyl-PEG8-FITC | Method B (one pot) | >200 | >10,000 1117. 23 | 1117.4317 [M+H]+ |
| 142 | positive control | | | 74 | |
| 140 | positive control | | 4 | | |
| 141 | positive control | | | 2 | |

Fig. 1N

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA targeting AHA1

<400> SEQUENCE: 1
ggaugaagug gagauuagut t                       21

<210> SEQ ID NO 2
<211> LENGTH: 21
<212> TYPE: DNA
<213> ORGANISM: Artificial Sequence
<220> FEATURE:
<223> OTHER INFORMATION: siRNA targeting AHA1

<400> SEQUENCE: 2
acuaaucucc acuucaucct t                       21

INTEGRIN ANTAGONIST CONJUGATES FOR TARGETED DELIVERY TO CELLS EXPRESSING LFA-1

This application is a National Stage Application of PCT/EP2013/051273 filed Jan. 24, 2013, which claims priority from Provisional Application No. 61/591,297 filed on Jan. 27, 2012 and Provisional Application No. 61/678,673 filed Aug. 2, 2012. Each of these applications is hereby incorporated by reference herein in its entirety.

The present invention relates to the synthesis and reaction of potent and selective small molecule integrin antagonists containing appropriate linkers and functional groups for chemical reaction with other molecules which contain reactive nucleophiles such as thiols such that a covalent linkage is formed between a moiety to be conjugated and the targeting entity. The small molecule targeting antagonists bind to cognate receptor systems as LFA-1 antagonists and/or dual LFA-1/MAC-1 antagonists to the ICAM-1 receptor. The covalently linked moiety includes small molecule therapeutics, polymers, peptides, and oligonucleotides. Included are 5'-thio-containing oligonucleotides for formation of 5'-thio-siRNA derivatives as a means to enable targeted delivery of said siRNAs. Such derivatized siRNAs in conjunction with appropriate transfection agents aid in the selective delivery of siRNAs to cells which express such integrin receptors, thereby preventing the expression of target genes through RNA interference (RNAi).

The lymphocyte function-associated antigen 1, also known as LFA-1 is an integrin which is found on all T-cells and also on B-cells, macrophages and neutrophils and is involved in recruitment to the site of infection. It binds to ICAM-1 on antigen-presenting cells and functions as an adhesion molecule. ICAM-1 (Inter-Cellular Adhesion Molecule 1) also known as CD54 (Cluster of Differentiation 54) is a cell surface glycoprotein. Aberrant levels of LFA-1/ICAM-1 interactions are thought to be operative in inflammatory diseases and disorders and therefore, the antagonism of such systems is thought to be a means of therapy. Therefore, the targeting of high affinity small molecules to these systems may provide a means to selectively deliver therapeutics such as siRNA to cellular systems that express the ICAM-1 receptor.

RNA interference is a well-known process in which the translation of messenger RNA (mRNA) into protein is interfered with by the association or binding of complementary or partially complementary oligonucleotides such as small interfering RNA (siRNA), short hairpin RNA (shRNA), micro RNA (miRNA), or antisense oligonucleotides. siRNAs are double-stranded RNA molecules, usually ranging from 19-25 nucleotides in length that associate with a set of proteins in the cytoplasm known as RISC (RNA-induced silencing complex). RISC ultimately separates the double stranded siRNA allowing one strand to bind or associate with a complementary or partially complementary portion of an mRNA molecule after which the mRNA is destroyed by RISC or otherwise prevented from being translated—consequently suppressing the expression of the encoded protein or gene product.

One of the problems in using nucleic acids such as siRNA in therapeutic applications (especially for systemic administration in humans) has been in delivering the nucleic acids to: (1) particular target tissues or cell types and (2) to the cytoplasm of those cells (i.e., where the mRNA is present and translated into protein). Part of the delivery problem is based on the fact that nucleic acids are negatively charged and easily degraded (especially if unmodified), efficiently filtered by the kidney, and cannot be easily transported to the cytoplasm of the cells by themselves. Thus, a significant amount of research has focused on solving the delivery problem with various carriers and formulations including liposomes, micelles, peptides, polymers, conjugates and aptamers. See Ling et al, *Advances in Systemic siRNA Delivery*, Drugs Future 34(9): 721 (September 2009). Some of the more promising delivery vehicles have involved the use of lipidic systems including lipid nanoparticles. See Wu et al., *Lipidic Systems for In Vivo siRNA Delivery*, AAPS J. 11(4): 639-652 (December 2009); International Patent Application Publication No. WO 2010/042877 by Hope et al ("*Improved Amino Lipids And Methods For the Delivery of Nucleic Acids*"). However, a need remains for further improved targeting of siRNA, as well as other substances such as small molecules, peptides, other nucleic acids, fluorescent moieties, and polymers to particular target cells and to the cytoplasm of such cells.

The invention relates to compounds of formula I:

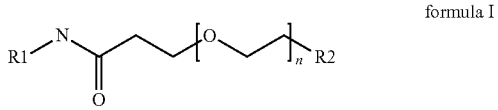

formula I wherein R1, R2, and n are defined in the detailed description and claims. In particular, the present invention relates to the compounds of formula I for the improved delivery of conjugated moieties such as small molecules, peptides, nucleic acids, fluorescent moieties, and polymers to target cells expressing the integrin α4β1 (Very Late Antigen-4) dimer, the αVβ3 dimer, or the lymphocyte function-associated antigen 1 (LFA-1) for various therapeutic and other applications. The present invention also relates to methods of manufacturing and using such compounds.

BRIEF DESCRIPTION OF THE DRAWINGS

FIGS. 1A-1B: Table 1 shows the composition of particular 5'-derivatized siRNA single and double strands.

FIG. 1C: Table 2 shows analytical data for small molecule siRNA conjugates.

FIGS. 1D-1E: Table 3 shows the siRNA sequences wherein the 5'-antisense strand has been derivatized with Nu547.

FIGS. 1F-1J: Table 4 shows small molecule-siRNA conjugate potencies in integrin antagonists assays and siRNA KD data.

FIGS. 1K-1N: Table 5 shows the identity, characterization and binding potencies of FITC isomer labeled reagents.

FIG. 1O: shows a histogram ("B": Duplex-27 500 nM and Example 140 10 μM; "A": Duplex-27).

Figure 1K:
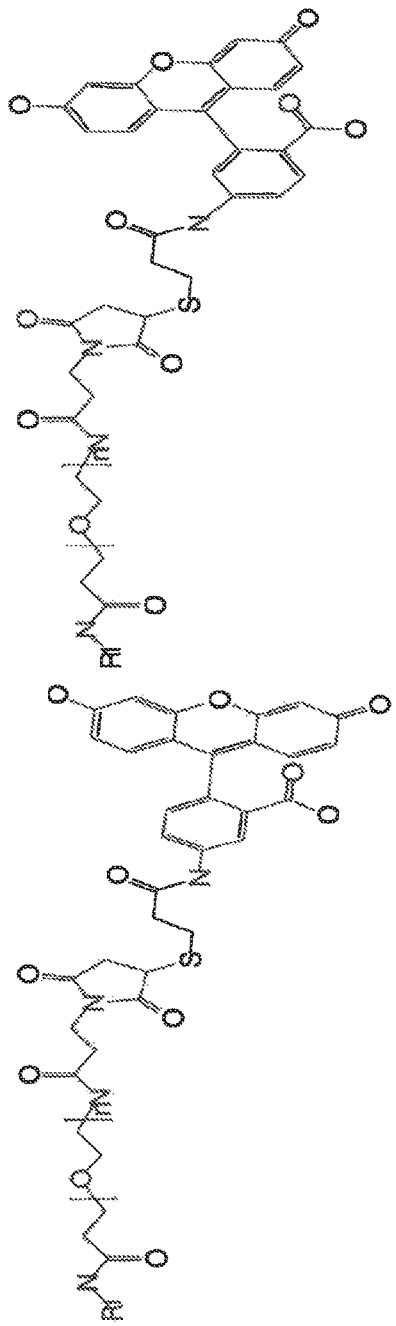
Figure 10:
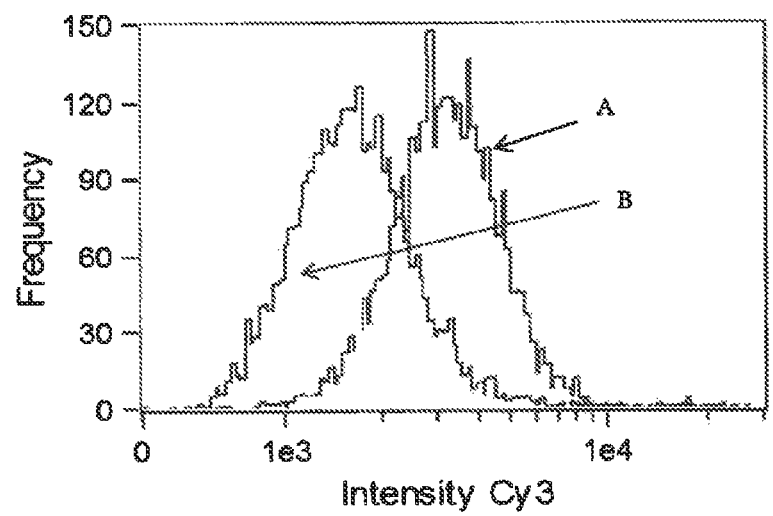
Figure 2:
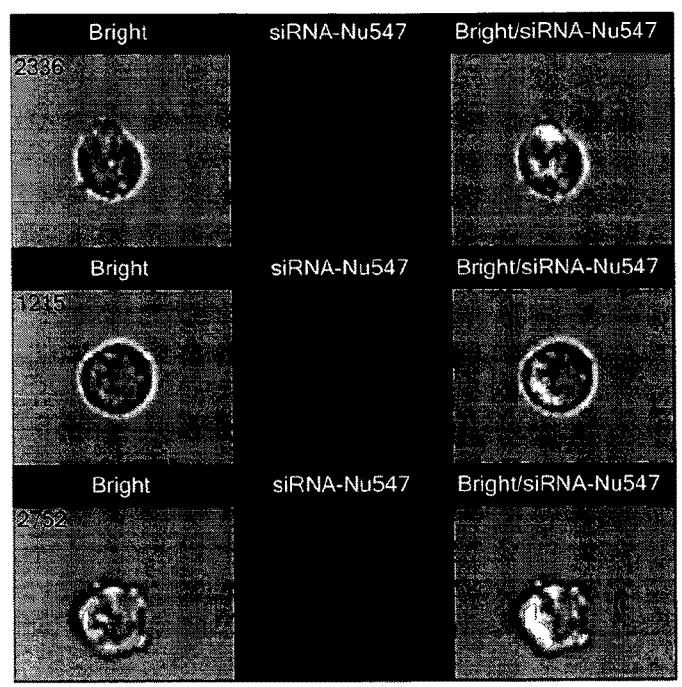
FIG. 2 shows representative siRNA uptake image (Duplex-27 (500 nM).
Figure 3:
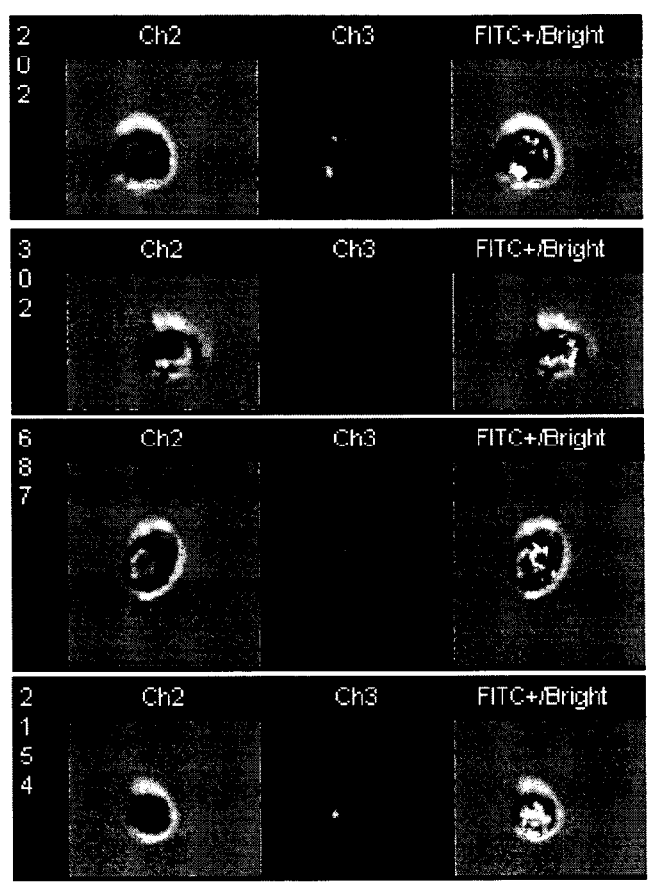
FIG. 3 shows images of Jurkat cells with FITC conjugated with Example FITC-5 (LFA-1 antagonist-labeled FITC) at 10 μM.
Figure 4:
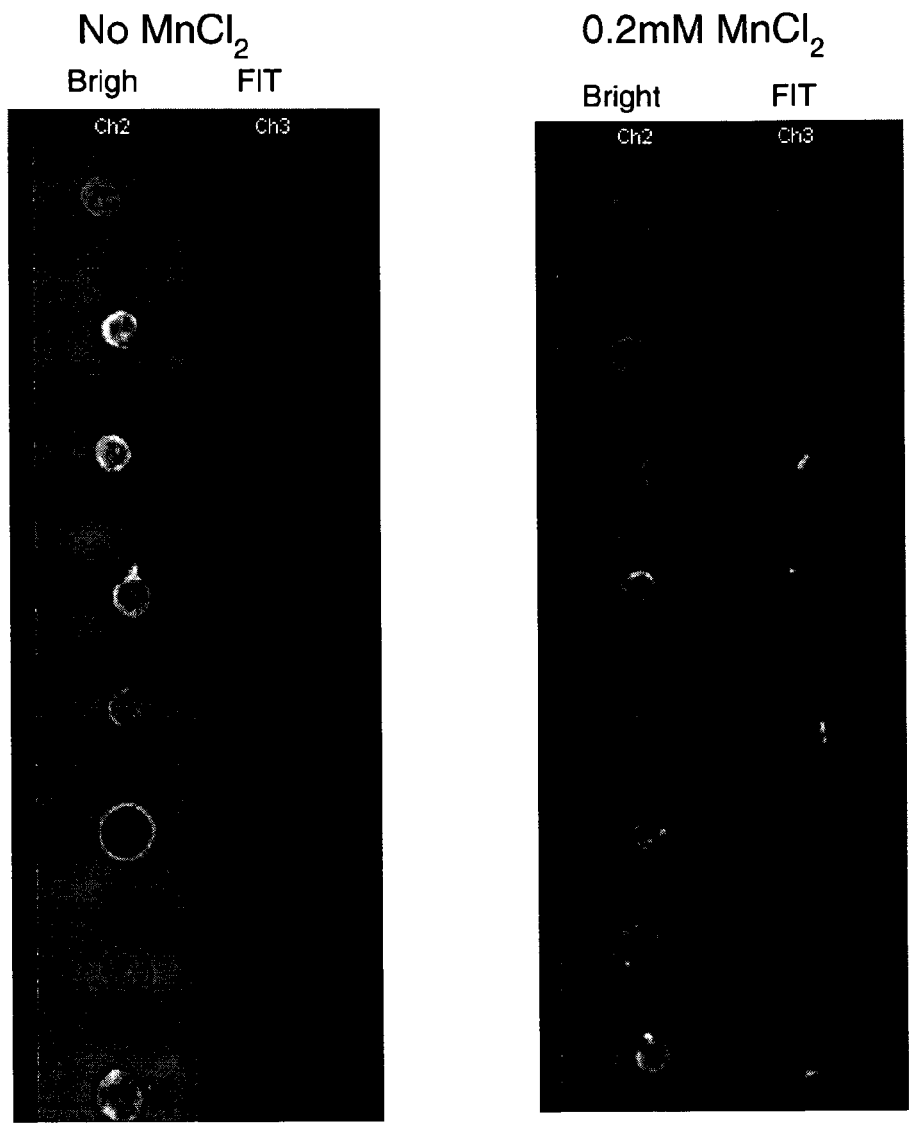
FIG. 4 shows images of Jurkat cells with FITC conjugated with Example FITC-14 (VLA-4 antagonist-labeled FITC) at 10 μM. The histograph indicates a shift in presence of the siRNA duplex with a VLA-4 targeting element. In the presence of VLA-4 antagonist example 140, this shift is oblated.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1 and R2 of formula I refer to moieties that are attached to the structure shown in formula I by a covalent bond where indicated.

The term "conjugated moiety" refers to moiety which is a therapeutic or useful compound, peptide, polymer, small molecule, fluorescent moiety, oligonucleotide or nucleic acid. Examples include drugs, therapeutic peptides, antisense oligonucleotides, siRNA, and fluorescein isothiocyanate (FITC).

Unless otherwise indicated, the term "hydrogen" or "hydro" refers to the moiety of a hydrogen atom (—H) and not $H_2$.

The term "halogen" refers to a moiety of fluoro, chloro, bromo or iodo.

The term "alkyl" refers to an aliphatic straight-chain or branched-chain saturated hydrocarbon moiety having 1 to 25 carbon atoms.

The term "TFA" refers to trifluoroacetic acid.

Unless otherwise indicated, the term "a compound of the formula" or "a compound of formula" or "compounds of the formula" or "compounds of formula" means any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Depending on the substitution patterns, the compounds of the present invention may also exist as zwitterions.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" means an amount of a compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

In detail, the present invention relates to the compounds of formula I:

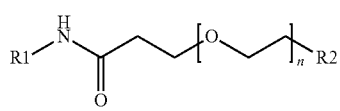
Formula I
or pharmaceutically acceptable salts or esters thereof;
wherein n is 1-24 and wherein:
R1 is selected from the group consisting of:
 (1) a compound of the formula:
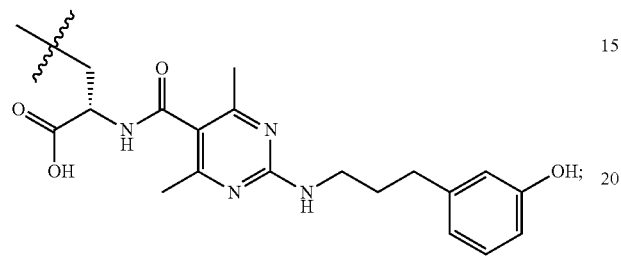
 (2) a compound of the formula:
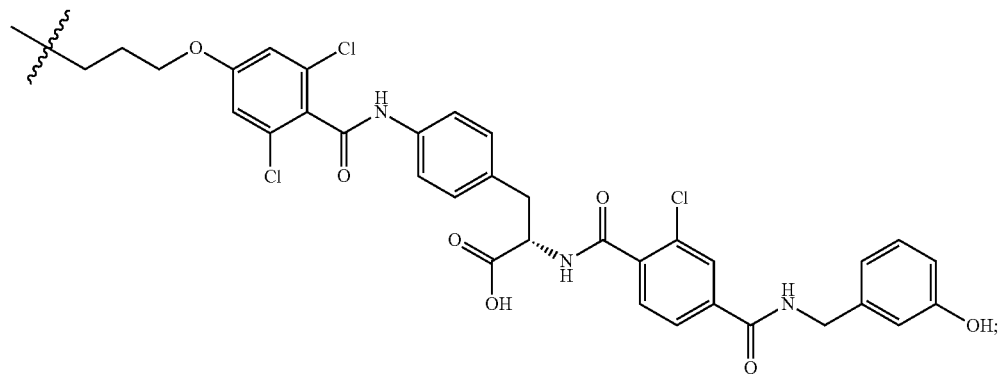 [SMILES: *CCCOc1cc(Cl)c(C(=O)Nc2ccc(C[C@H](NC(=O)c3ccc(C(=O)NCc4cccc(O)c4)cc3Cl)C(=O)O)cc2)c(Cl)c1]
and
 (3) a compound of the formula:
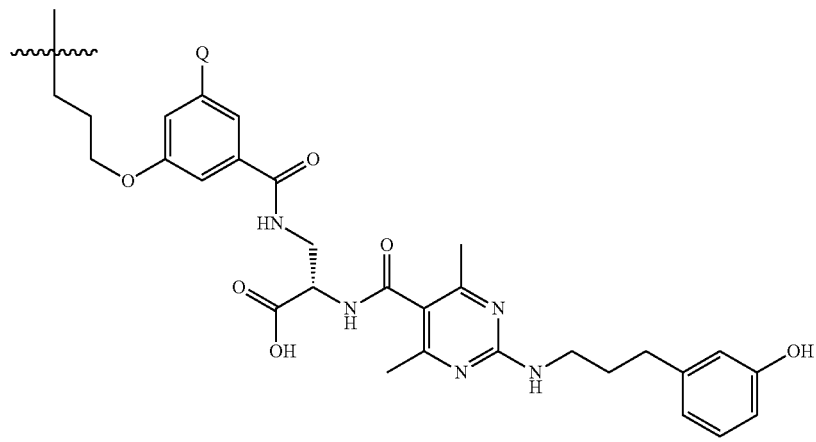
wherein Q is H or OH;
R2 is selected from the group consisting of:
 (1) a compound of the formula:
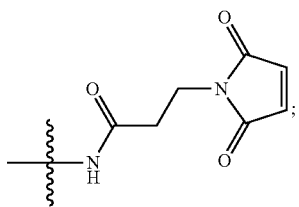 [SMILES: *NC(=O)CCN1C(=O)C=CC1=O]
 (2) a compound of the formula:
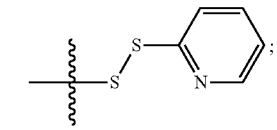

(3) a compound of the formula:

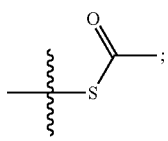 [SMILES: *SC(C)=O]

and (4) a compound of the formula:

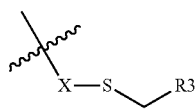

wherein R3 is a conjugated moiety and X represents either sulfur or a compound of the formula:

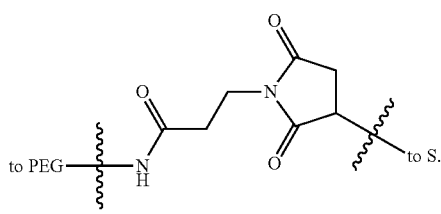

As used in the above structures, the symbol ⸙ is used to indicate where the structure or moiety is attached to the base molecule by a covalent bond. In addition, the phrase "to PEG" or "to S" or similar language used in combination with the above symbol, indicates where or how the structure or moiety is attached to the base molecule if there a multiple attachment points. For example, if R2 is a compound of the formula:

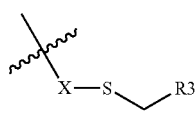

wherein X is a compound of the formula:

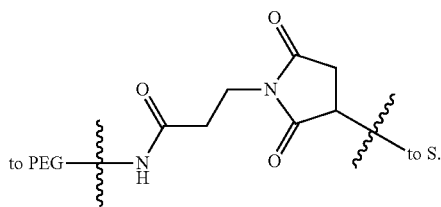

then the structure based upon formula I would be:

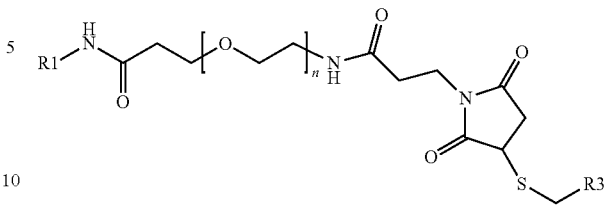

wherein R1, R3, and n are as defined in formula I.

The present invention also relates to methods of manufacturing and using the compounds of formula I as well as pharmaceutical compositions containing such compounds. The compounds of formula I are useful in improving the delivery of small molecules, proteins, nucleic acids, polymers, fluorescent markers, and other substances to target cells expressing ICAM-1 receptors. In particular embodiments, the present invention relates to compositions and formulations containing the compounds of formula I which are useful in delivering siRNA to the cytoplasm of target cells expressing ICAM-1 receptors to inhibit the expression of certain target proteins through RNA interference.

In more particular embodiments, the invention relates to the use of the compounds of formula I for formulation to facilitate the delivery of nucleic acids such as siRNA to tumor cells and other cell types expressing ICAM-1 receptors. Furthermore, the use of the compounds of formula I to synthesize delivery formulations to treat inflammation and proliferative disorders, like cancers, is part of the invention.

R1 represents small molecule integrin antagonists which target the compounds of formula I to LFA-1 integrins, thereby facilitating their delivery to cells that express such receptors.

In particular embodiments, the small molecule integrin antagonist targeting moieties of R1 are attached at a position such that the affinity of binding of the small molecule to the integrin is not substantially reduced relative to the free small molecule integrin antagonist. The R1 moieties of formula I target the ICAM-1 receptor (via the LFA-1 or dual LFA-1/MAC-1 antagonists to the ICAM-1 receptor).

In particular embodiments, R1 is an LFA-1 and/or dual LFA-1/MAC-1 antagonists or ICAM-1 receptor targeting moiety of the formula:

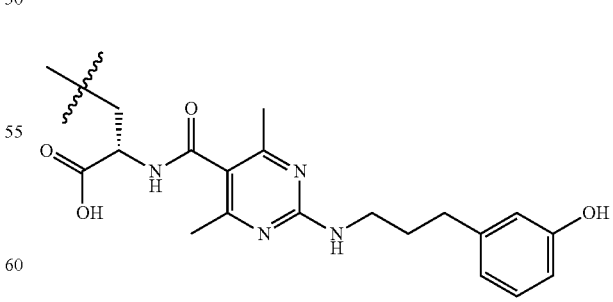

or a pharmaceutically acceptable salt or ester thereof.

In other embodiments, R1 is an LFA-1 and/or dual LFA-1/MAC-1 antagonists or ICAM-1 receptor targeting moiety of the formula:

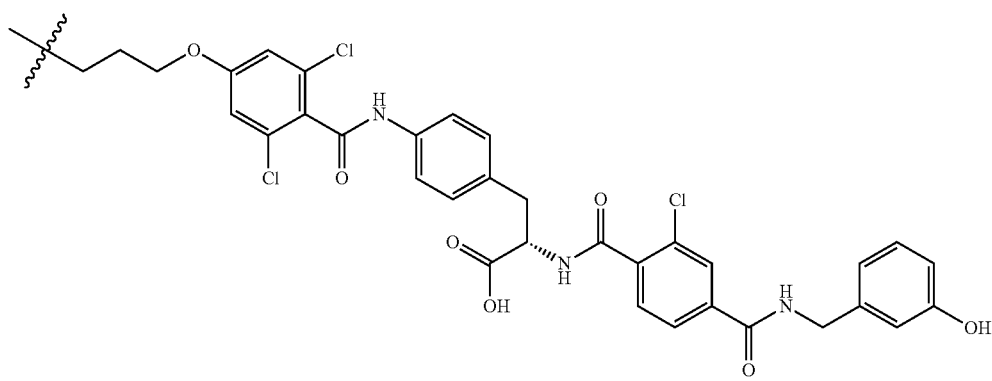 [SMILES: *CCCOc1cc(Cl)c(C(=O)Nc2ccc(C[C@H](NC(=O)c3ccc(C(=O)NCc4cccc(O)c4)cc3Cl)C(=O)O)cc2)c(Cl)c1]

or a pharmaceutically acceptable salt or ester thereof.

In other embodiments, R1 is an LFA-1 and/or dual LFA-1/MAC-1 antagonists or ICAM-1 receptor targeting moiety of the formula:

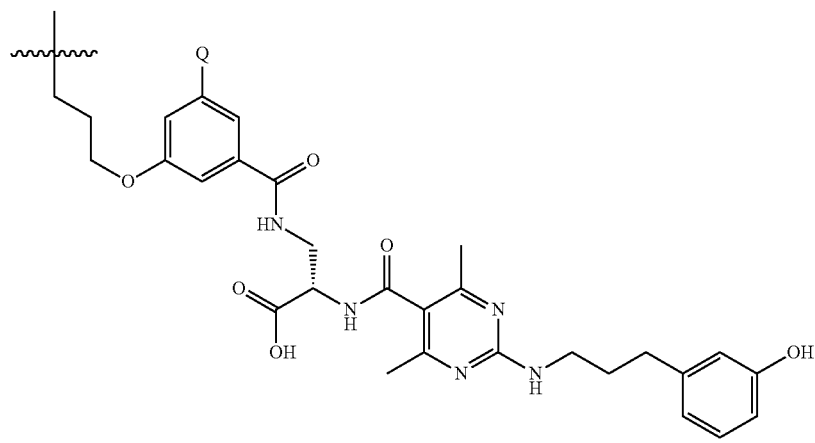

or a pharmaceutically acceptable salt or ester thereof, wherein Q is H or OH.

R2 may represent reactive moieties which can form covalent linkages with therapeutic or other useful compounds or conjugated moieties having strong nucleophiles such as thiol-containing molecules. Examples of such reactive moieties include moieties selected from the group consisting of:

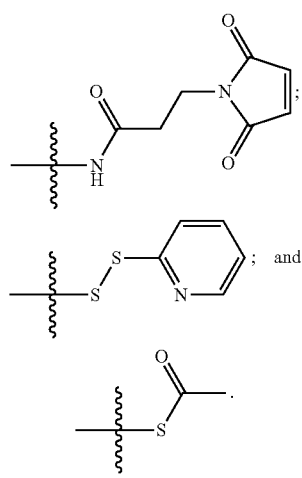

Alternatively, R2 may represent a moiety which is already attached to a conjugated moiety such as a therapeutic or other useful compound, protein, or oligonucleotide (R3). More specifically, R2 may represent a moiety of the formula:

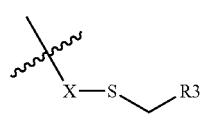

wherein R3 is a conjugated moiety and X represents either sulfur or a compound of the formula:

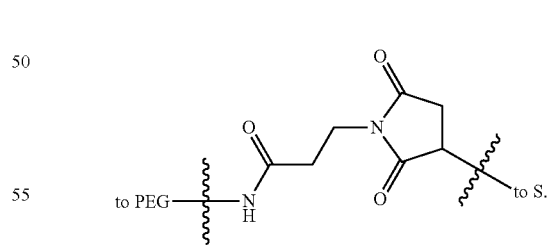

In particular embodiments, R3 represents an oligonucleotide. In more specific embodiments, R3 represents the 5'-end of the sense strand of an RNA molecule which may exist as a single strand or in a duplex such as a siRNA molecule. Such siRNA molecules, also known as RNAi agents, inhibit the expression of a target gene in a cell. In specific embodiments, R3 is a siRNA molecule that consists essentially of an oligoribonucleotide strand of between 15 and 30 nucleotides in length, wherein the 5' terminus of the sense oligoribonucleotide strand is coupled to R2 as shown in the above structures and is complementary to at least one portion of an mRNA corresponding to the target gene. In other embodiments, R3 is an oligonucleotide of DNA attached at its 5'-end. Such derivatized DNA may exist as a single strand or as one strand hybridized with a complementary strand of another oligonucleotide. The oligonucleotide strands can be either unmodified or modified for metabolic stability. Such modifications include, but are not limited to, substitutions at specific positions on the phosphate (e.g., phosphorothioate) and 2'-hydroxy (e.g., 2'-O-methyl and 2'-fluoro).

In particular embodiments, R2 of formula I represents —X—S—CH$_2$—R3 wherein R3 includes a sense strand of RNA as shown below in formula 5 (based on formula I):

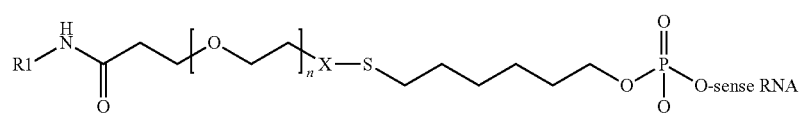

5 wherein R1, n, and X are as defined in formula I.

In other particular embodiments, the sense strand may be bound to an antisense strand.

In other specific embodiments, R2 represents —X—S—CH$_2$—R3 wherein R3 represents a small molecule or protein, thereby forming a covalently linked, specifically targeted entity of formula I.

In more specific embodiments, R2 represents —X—S—CH$_2$—R3 wherein R3 represents a therapeutic small molecule or protein.

In other specific embodiments, R2 represents —X—S—CH$_2$—R3 wherein R3 represents a fluorescent moiety useful for the visualization of these integrin receptor bindings using cellular microscopy techniques.

In other specific embodiments, R2 represents —X—S—CH$_2$—R3 wherein R3 represents a polymer having primary, reactive sulfides. More specifically, R3 may represent a cationic polymer useful for the complexation and delivery of siRNA to cell surfaces and the cytoplastic domains of cells.

In more particular embodiments, the present invention is directed to compounds of formula I wherein R3 is one of the structural isomers of fluorescein isothiocyanate (FITC) shown below:

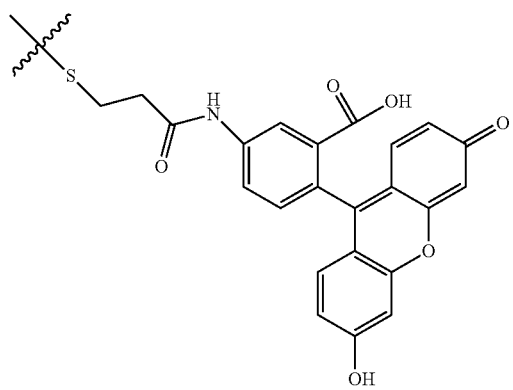

-continued

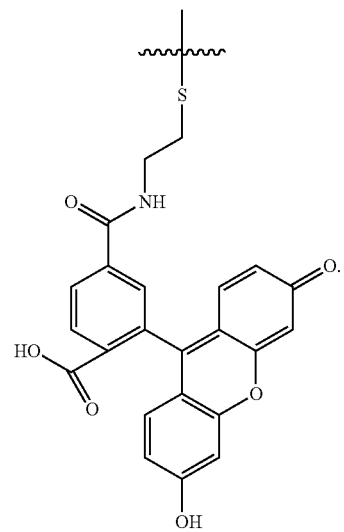

In other more particular embodiments, the present invention is directed to compounds of formula I wherein R3 is one of the structural isomers of FITC-14 shown below:

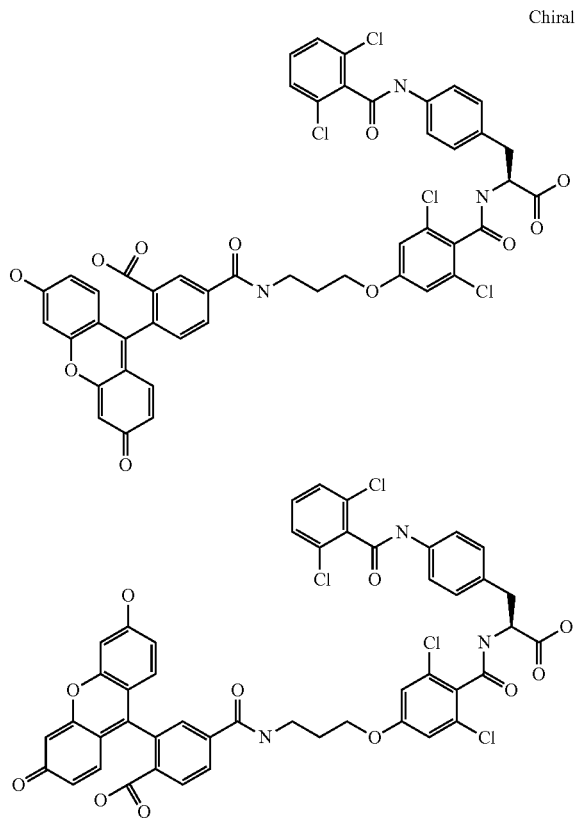

In other embodiments, the present invention is directed to a compound of formula I wherein n is 9-13, preferably 12.

In more specific embodiments, the present invention is directed to a compound of formula I selected from the group consisting of one of the following compounds (or a pharmaceutically acceptable salt or ester thereof):

LFA-1 Ligand Reagent 1
(S)-3-{3-{2-[2-(2-{2-[3-(2,5-Dioxo-2,5-dihydro-pyrrol-1-yl)-propionylamino]-ethoxy]-ethoxy}-ethoxy)-ethoxy]-propionylamino}-2-({2-[3-(3-hydroxy-phenyl)-propylamino]-4,6-dimethyl-pyrimidine-5-carbonyl}amino) propionic acid;

LFA-1 Ligand Reagent 2
(S)-3-{3-(2-{2-[2-(2-{2-[2-(2-{2-[3-(2,5-Dioxo-2,5-dihydro-pyrrol-1-yl)-propionylamino]-ethoxy)-ethoxy]-ethoxy}-ethoxy)-ethoxy]-ethoxy}-ethoxy)-ethoxy]-propionylamino}-2-({2-[3-(3-hydroxy-phenyl)-propylamino]-4,6-dimethyl-pyrimidine-5-carbonyl}amino)propionic acid;

LFA-1 Ligand Reagent 3
(S)-3-{3-[2-(2-{2-[2-(2-{2-[2-(2-{2-[2-(2-{2-[3-(2,5-Dioxo-2,5-dihydro-pyrrol-1-yl)- propionylamino]-ethoxy}-ethoxy)-ethoxy]-ethoxy}-ethoxy)-ethoxy]-ethoxy}-ethoxy)-ethoxy]-ethoxy}-ethoxy)-ethoxy]-propionylamino}-2-({2-[3-(3-hydroxy-phenyl)-propylamino]-4,6-dimethyl-pyrimidine-5-carbonyl}amino)propionic acid;

LFA-1 Ligand Reagent 4
(S)-3-{4-[4-(3-(2-{2-[2-(2-{2-[2-(2-{2-ethoxy)-ethoxy]-ethoxy}-ethoxy)-ethoxy]-ethoxy}-ethoxy)-ethoxy]-amino-propoxy)-2,6-dichloro-benzoylamino]-phenyl}-2-[2-chloro-4-(3-hydroxy-benzylcarbamoyl)-benzoylamino]-propionic acid-PEGS;

LFA-1 Ligand Reagent 5
S)-2-[2-Chloro-4-(3-hydroxy-benzylcarbamoyl)-benzoylamino]-3-(4-{2,6-dichloro-4-[3-(3-{2-[2-(2-{2-[3-(2,5-dioxo-2,5-dihydro-pyrrol-1-yl)-propionylamino]-ethoxy)-ethoxy]-ethoxy}-propionylamino)-propoxy]-benzoylamino}-phenyl)-propionic acid;

LFA-1 Ligand Reagent 6
S)-2-[2-Chloro-4-(3-hydroxy-benzylcarbamoyl)-benzoylamino]-3-(4-{2,6-dichloro-4-[3-(3-{2-[2-(2-{2-2-[2-(2-{2-2-[2-(2-{2-[3-(2,5-dioxo-2,5-dihydro-pyrrol-1-yl)-propionylamino]-ethoxy}-ethoxy)-ethoxy]-ethoxy}-ethoxy)-ethoxy]-ethoxy}-propionylamino)-propoxy]-benzoylamino}-phenyl)-propionic acid;

LFA-1 Ligand Reagent 7
S)-2-[2-Chloro-4-(3-hydroxy-benzylcarbamoyl)-benzoylamino]-3-(4-{2,6-dichloro-4-[3-(3-{2-[2-(2-{2-2-[2-(2-{2-[3-(2,5-dioxo-2,5-dihydro-pyrrol-1-yl)-propionylamino]-ethoxy}-ethoxy)-ethoxy]-ethoxy]-ethoxy}-ethoxy)-ethoxy]-ethoxy}-propionylamino)-propoxy]-benzoylamino}-phenyl)-propionic acid;

LFA-1 Ligand Reagent 8
(S)-3-{[(3-{3-[3-(2-{2-[2-(2-{2-[2-(2-{2-[3-(2,5-Dioxo-2,5-dihydro-pyrrol-1-yl)-propionylamino]-ethoxy}-ethoxy)-ethoxy]-ethoxy}-ethoxy)-ethoxy]-ethoxy}-ethoxy)-propionylamino]-propyl-oxy}-phenyl)-carbonyl]-amino}-2-({2-[3-(3-hydroxy-phenyl)-propylamino]-4,6-dimethyl-pyrimidine-5-carbonyl}-amino)-propionic acid;

LFA-1 Ligand Reagent 9
(S)-3-{[(3-{3-[3-(2-{2-[2-(2-{2-[2-(2-{2-[3-(2,5-Dioxo-2,5-dihydro-pyrrol-1-yl)-propionylamino]-ethoxy}-ethoxy)-ethoxy]-ethoxy}-ethoxy)-ethoxy]-ethoxy}-ethoxy)-propionylamino]-propyl-oxy}-5-hydroxy-phenyl)-carbonyl]-amino}-2-({2-[3-(3-hydroxy-phenyl)-propylamino]-4,6-dimethyl-pyrimidine-5-carbonyl}-amino)-propionic acid;

LFA-1 Ligand Reagent 10
(S)-3-[({3-[3-(3-{2-[2-(2-{2-[3-(2,5-Dioxo-2,5-dihydro-pyrrol-1-yl)-propionylamino]-ethoxy}-ethoxy)-ethoxy]-ethoxy}-propionylamino)-propyl-oxy]-5-hydroxy-phenyl}-carbonyl)-amino]-2-({2-[3-(3-hydroxy-phenyl)-propylamino]-4,6-dimethyl-pyrimidine-5-carbonyl}-amino)-propionic acid.

In addition, the present invention relates to novel compositions and formulations containing compounds of formula I for the creation of nanoparticles upon combination with siRNA, resulting in the improved delivery of nucleic acids such as siRNA to the cytoplasm of target cells expressing LFA-1/ICAM-1 complexes. In particular embodiments, the present invention is directed to a siRNA formulation comprising: (1) a compound of formula I wherein R2 includes a 5'-siRNA oligonucleotide; and (2) a polycationic transfection agent.

The present invention also relates to methods of manufacturing and using such compounds and compositions. The compounds of formula I are useful as components of compositions or formulations which improve the delivery of drugs, nucleic acids, or other therapeutic compounds to tissues or cells expressing LFA-1/ICAM-1 complexes. In particular embodiments, the present invention relates to formulations containing the compounds of formula I which are useful in delivering siRNA to the cytoplasm of target cells LFA-1/ICAM-1 complexes to inhibit the expression of certain proteins through RNA interference. In more particular embodiments, the present invention relates to the compounds of formula I and compositions containing such compounds that can effectively deliver siRNA to tumor cells and other cell types expressing ICAM-1 receptors for the treatment of cancer or inflammatory diseases. Such compounds and compositions are more efficacious and demonstrate improved knockdown capability compared to similar formulations lacking the compounds of formula I.

In one embodiment of the invention there is provided a compound of formula I:

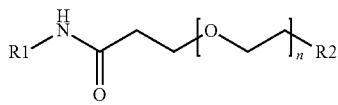

formula I or a pharmaceutically acceptable salt or ester thereof; wherein n is 1-24 and wherein:

R1 is selected from the group consisting of:

(1) a compound of the formula:

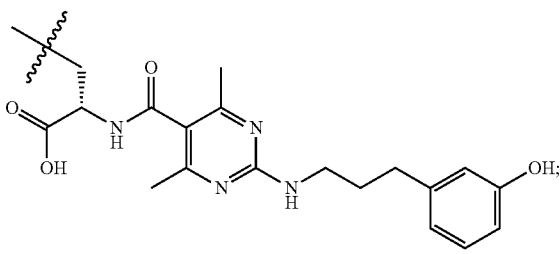 [SMILES: *C[C@H](NC(=O)c1c(C)nc(NCCCc2cccc(O)c2)nc1C)C(=O)O]

(2) a compound of the formula:

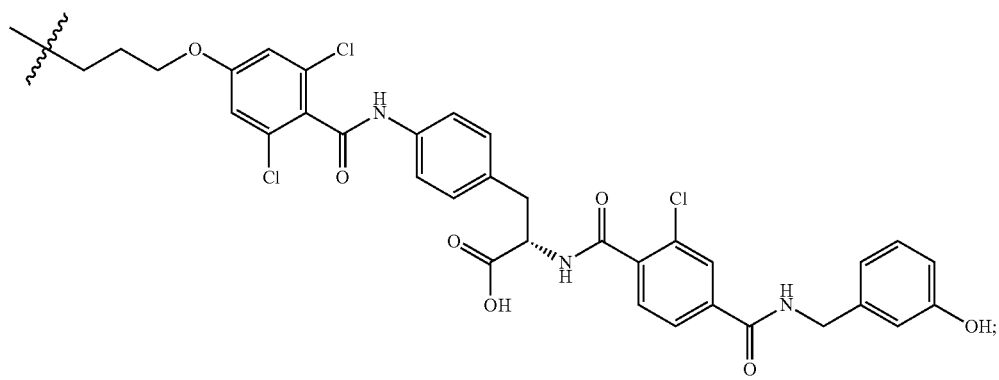 [SMILES: *CCCOc1cc(Cl)c(C(=O)Nc2ccc(C[C@H](NC(=O)c3ccc(C(=O)NCc4cccc(O)c4)cc3Cl)C(=O)O)cc2)c(Cl)c1]

and
(3) a compound of the formula:

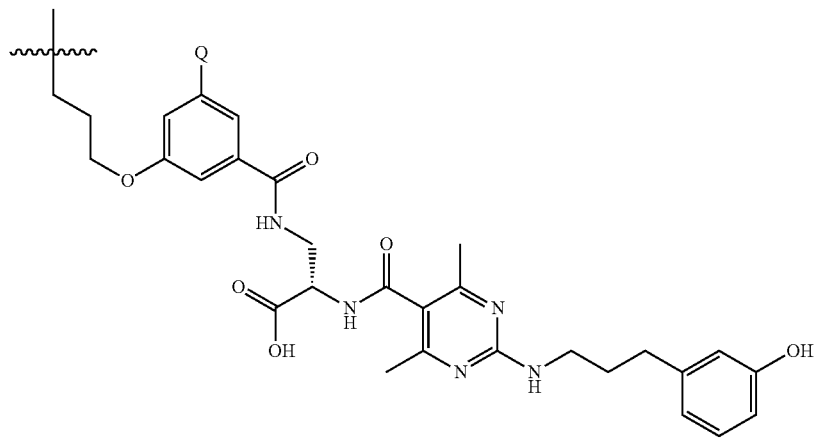

wherein Q is H or OH;

R2 is selected from the group consisting of:

(1) a compound of the formula:

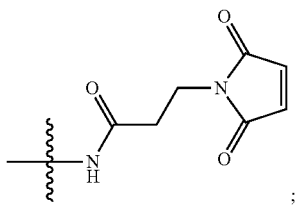 [SMILES: *NC(=O)CCN1C(=O)C=CC1=O ; ";"]
;

(2) a compound of the formula:

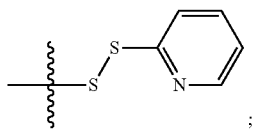
;

(3) a compound of the formula:

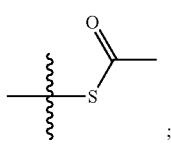 [SMILES: *SC(C)=O ; ";"]
;

and (4) a compound of the formula:

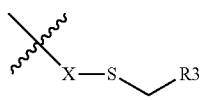

wherein R3 is a conjugated moiety and X represents either sulfur or a compound of the formula:

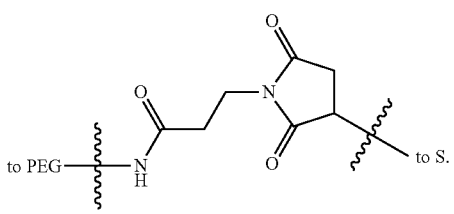

In one embodiment of the invention there is provided a compound of formula I, wherein R1 is a compound of the formula:

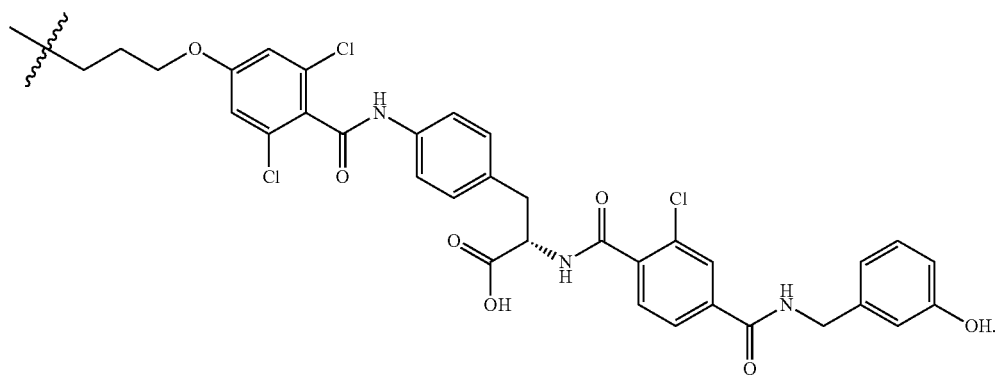 [SMILES: *CCCOc1cc(Cl)c(C(=O)Nc2ccc(C[C@H](NC(=O)c3ccc(C(=O)NCc4cccc(O)c4)cc3Cl)C(=O)O)cc2)c(Cl)c1]

In one embodiment of the invention there is provided a compound of formula I, wherein R1 is a compound of the formula:

In one embodiment of the invention there is provided a compound of formula I, wherein R1 is a compound of the formula:

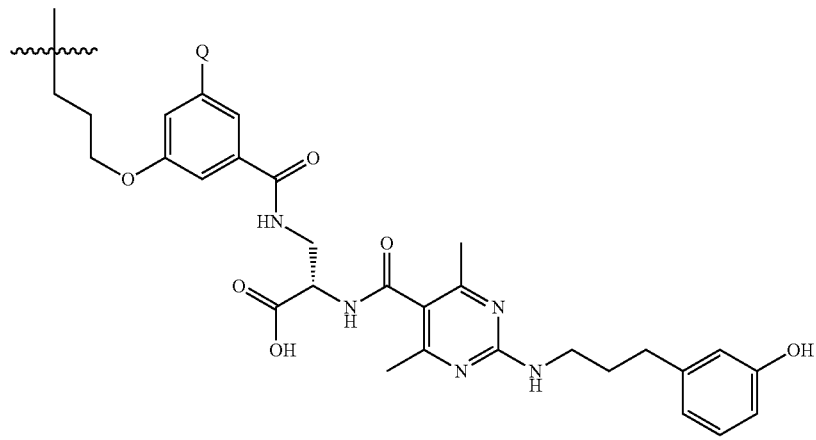

wherein Q is H or OH.

In one embodiment of the invention there is provided a compound of formula I, wherein R1 is a compound of the formula:

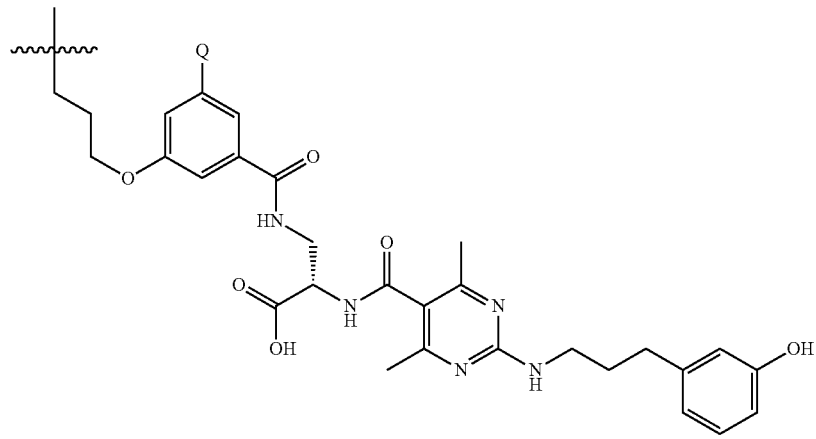

wherein Q is H.

In one embodiment of the invention there is provided a compound of formula I, wherein R1 is a compound of the formula:

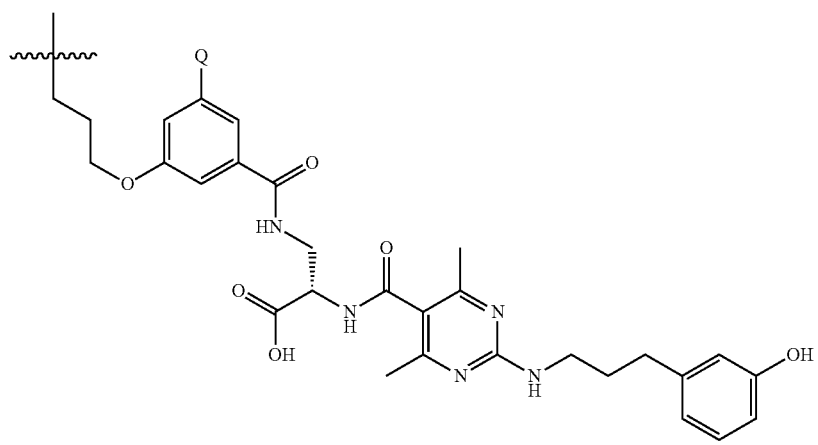

wherein Q is OH.

In one embodiment of the invention there is provided a compound of formula I, wherein R2 is a compound of the formula:

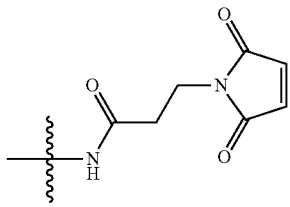

In one embodiment of the invention there is provided a compound of formula I, wherein R2 is a compound of the formula:

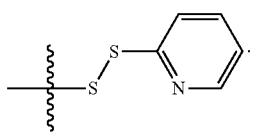

In one embodiment of the invention there is provided a compound of formula I, wherein R2 is a compound of the formula:

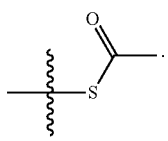 [SMILES: *SC(C)=O]

In one embodiment of the invention there is provided a compound of formula I, wherein R2 is a compound of the formula:

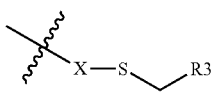

wherein R3 is a single or double stranded oligonucleotide and X represents either sulfur or a compound of the formula:

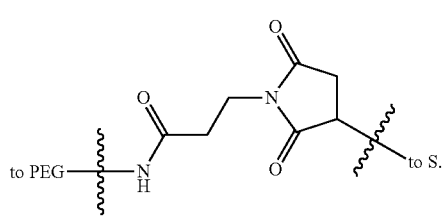

In one embodiment of the invention there is provided a compound of formula I, wherein R2 is a compound of the formula:

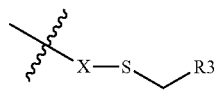

wherein R3 is a single or double stranded oligonucleotide and X represents sulfur.

In one embodiment of the invention there is provided a compound of formula I, wherein R2 is a compound of the formula:

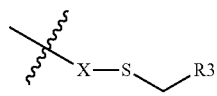

wherein R3 is a siRNA molecule and X represents either sulfur or a compound of the formula:

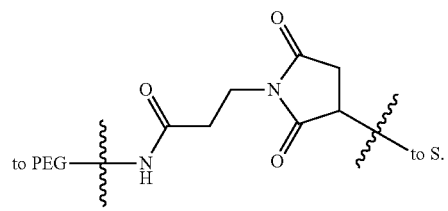

In one embodiment of the invention there is provided a compound of formula I, wherein R1 a compound of the formula:

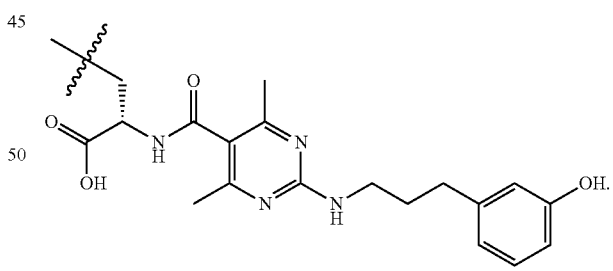

wherein R2 is a compound of the formula:

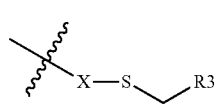

wherein R3 is a siRNA molecule and X represents either sulfur or a compound of the formula:

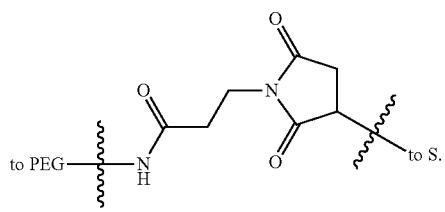
In one embodiment of the invention there is provided a compound of formula I, wherein R1 a compound of the formula:
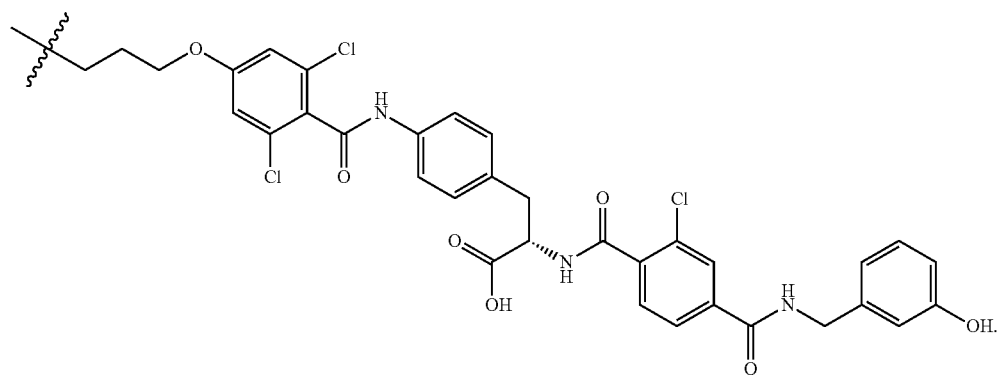
wherein R2 is a compound of the formula:
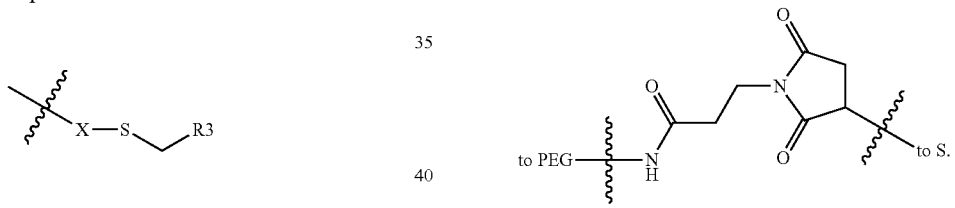
wherein R3 is a siRNA molecule and X represents either sulfur or a compound of the formula:
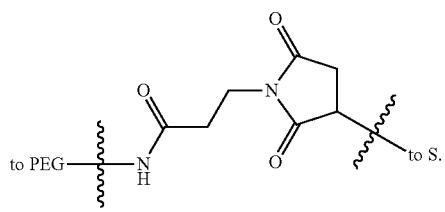
In one embodiment of the invention there is provided a compound of formula I, wherein R1 a compound of the formula:
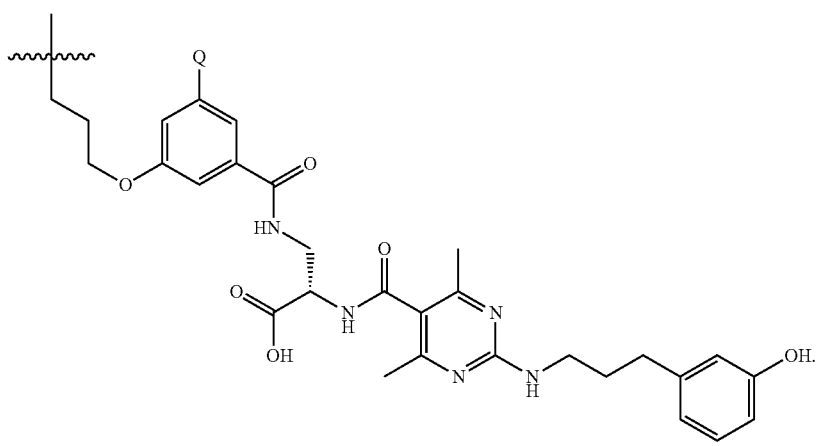

wherein Q is H or OH.
wherein R2 is a compound of the formula:

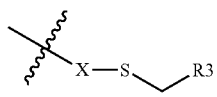

wherein R3 is a siRNA molecule and X represents either sulfur or a compound of the formula:

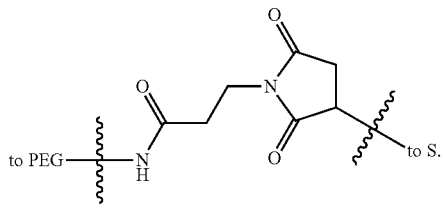

In one embodiment of the invention there is provided a compound of formula I, selected from the group consisting of:
(S)-3-{3-{2-[2-(2-{2-[3-(2,5-Dioxo-2,5-dihydro-pyrrol-1-yl)-propionylamino]-ethoxy}-ethoxy)-ethoxy]-propionylamino}-2-({2-[3-(3-hydroxy-phenyl)-propylamino]-4,6-dimethyl-pyrimidine-5-carbonyl}amino) propionic acid; and
(S)-3-{3-(2-{2-[2-(2-{2-[3-(2-{2-[3-(2,5-Dioxo-2,5-dihydro-pyrrol-1-yl)-propionylamino]-ethoxy)-ethoxy]-ethoxy}-ethoxy)-ethoxy]-ethoxy}-ethoxy)-ethoxy]-propionylamino}-2-({2-[3-(3-hydroxy-phenyl)-propylamino]-4,6-dimethyl-pyrimidine-5-carbonyl}amino)propionic acid.

In one embodiment of the invention there is provided a compound of formula I, selected from the group consisting of:
(S)-3-{3-[2-(2-{2-[2-(2-{2-[2-(2-{2-[2-(2-{2-[3-(2,5-Dioxo-2,5-dihydro-pyrrol-1-yl)- propionylamino]-ethoxy}-ethoxy)-ethoxy]-ethoxy}-ethoxy)-ethoxy]-ethoxy}-ethoxy)-ethoxy]-ethoxy}-ethoxy)-ethoxy]-propionylamino}-2-({2-[3-(3-hydroxy-phenyl)-propylamino]-4,6-dimethyl-pyrimidine-5-carbonyl}amino)propionic acid; and
(S)-3-{4-[4-(3-(2-{2-[2-(2-{2-[2-(2-{2-ethoxy)-ethoxy]-ethoxy}-ethoxy)-ethoxy]-ethoxy}-ethoxy)-ethoxy]-amino-propoxy)-2,6-dichloro-benzoylamino]-phenyl}-2-[2-chloro-4-(3-hydroxy-benzylcarbamoyl)-benzoylamino]-propionic acid-PEGS.

In one embodiment of the invention there is provided a compound of formula I, selected from the group consisting of:
S)-2-[2-Chloro-4-(3-hydroxy-benzylcarbamoyl)-benzoylamino]-3-(4-{2,6-dichloro-4-[3-(3-{2-[2-(2-{2-[3-(2,5-dioxo-2,5-dihydro-pyrrol-1-yl)-propionylamino]-ethoxy}-ethoxy)-ethoxy]-ethoxy}-propionylamino)-propoxy]-benzoylamino}-phenyl)-propionic acid; and
S)-2-[2-Chloro-4-(3-hydroxy-benzylcarbamoyl)-benzoylamino]-3-(4-{2,6-dichloro-4-[3-(3-{2-[2-(2-{2-2-[2-(2-{2-2-[2-(2-{2-[3-(2,5-dioxo-2,5-dihydro-pyrrol-1-yl)-propionylamino]-ethoxy}-ethoxy)-ethoxy]-ethoxy}-ethoxy)-ethoxy]-ethoxy}-propionylamino)-propoxy]-benzoylamino}-phenyl)-propionic acid.

In one embodiment of the invention there is provided a compound of formula I, selected from the group consisting of:
S)-2-[2-Chloro-4-(3-hydroxy-benzylcarbamoyl)-benzoylamino]-3-(4-{2,6-dichloro-4-[3-(3-{2-[2-(2-{2-2-[2-(2-{2-[3-(2,5-dioxo-2,5-dihydro-pyrrol-1-yl)-propionylamino]-ethoxy}-ethoxy)-ethoxy]-ethoxy]-ethoxy}-ethoxy)-ethoxy]-ethoxy}-propionylamino)-propoxy]-benzoylamino}-phenyl)-propionic acid; and
(S)-3-{[(3-{3-[3-(2-{2-[2-(2-{2-[2-(2-{2-[3-(2,5-Dioxo-2,5-dihydro-pyrrol-1-yl)-propionylamino]-ethoxy}-ethoxy)-ethoxy]-ethoxy}-ethoxy)-ethoxy]-ethoxy}-propionylamino]-propyl-oxy}-phenyl)-carbonyl]-amino}-2-({2-[3-(3-hydroxy-phenyl)-propylamino]-4,6-dimethyl-pyrimidine-5-carbonyl}-amino)-propionic acid.

In one embodiment of the invention there is provided a compound of formula I, selected from the group consisting of:
(S)-3-{[(3-{3-[3-(2-{2-[2-(2-{2-[2-(2-{2-[3-(2,5-Dioxo-2,5-dihydro-pyrrol-1-yl)-propionylamino]-ethoxy}-ethoxy)-ethoxy]-ethoxy}-ethoxy)-ethoxy]-ethoxy}-ethoxy)-propionylamino]-propyl-oxy}-5-hydroxy-phenyl)-carbonyl]-amino}-2-({2-[3-(3-hydroxy-phenyl)-propylamino]-4,6-dimethyl-pyrimidine-5-carbonyl}-amino)-propionic acid; and
(S)-3-[({3-[3-(3-{2-[2-(2-{2-[3-(2,5-Dioxo-2,5-dihydro-pyrrol-1-yl)-propionylamino]-ethoxy}-ethoxy)-ethoxy]-ethoxy}-propionylamino)-propyl-oxy]-5-hydroxy-phenyl}-carbonyl)-amino]-2-({2-[3-(3-hydroxy-phenyl)-propylamino]-4,6-dimethyl-pyrimidine-5-carbonyl}-amino)-propionic acid.

In another embodiment of the invention there is provided a pharmaceutical composition comprising a compound of formula I and a pharmaceutically acceptable carrier.

General Synthesis of the Compounds of the Invention

Suitable processes for synthesizing compounds of formula I are provided in the examples. Generally, compounds of formula I can be prepared according to the schemes illustrated below. Unless otherwise indicated, the variables n and R1 and R2 in the schemes below are defined in the same manner as defined previously for the genus of formula I.

General Synthesis of Maleimide-(PEG)n-Integrin Antagonists Conjugating Agents

Compounds such as 26 in scheme 1 of various lengths of PEG are commercially available (e.g., from Pierce BioScience). Such compounds can also be made as by acylating the amino termini of PEG amino acids with 3-(2,5-dioxo-2,5-dihydro-pyrrol-1-yl)-propionic acid under amide bond forming conditions, followed by formation of reactive N-hydroxysuccinic esters by reaction of N-hydroxy succinic acid under ester forming conditions. As shown in scheme 1, reacting the compounds of 26 with compounds containing primary or secondary amines such as 27 are conducted in aprotic or protic solvents in the presence of basic amines such as DIEA (diisopropylethylamine) at room temperature generating the PEGylated intermediates of 28.

Scheme 1

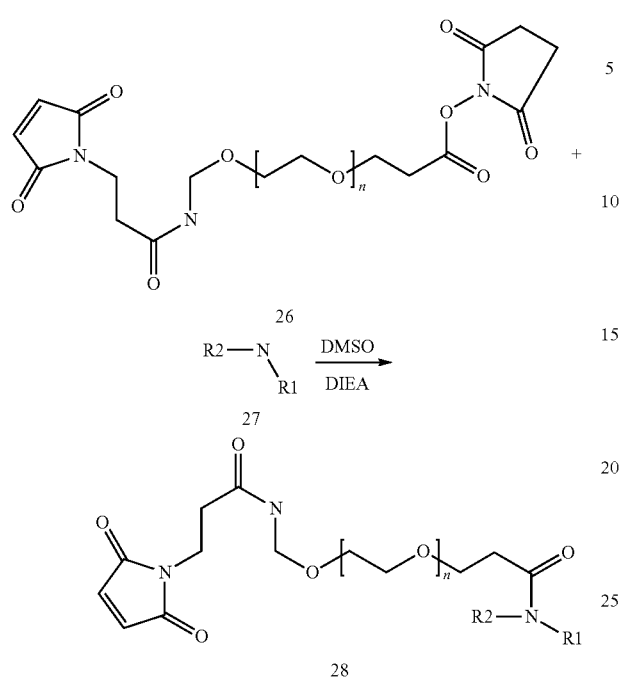

protic solvents in the presence of basic amines such as DIEA (diisopropylethylamine) at room temperature generating the PEGylated intermediates of 30.

Scheme 2

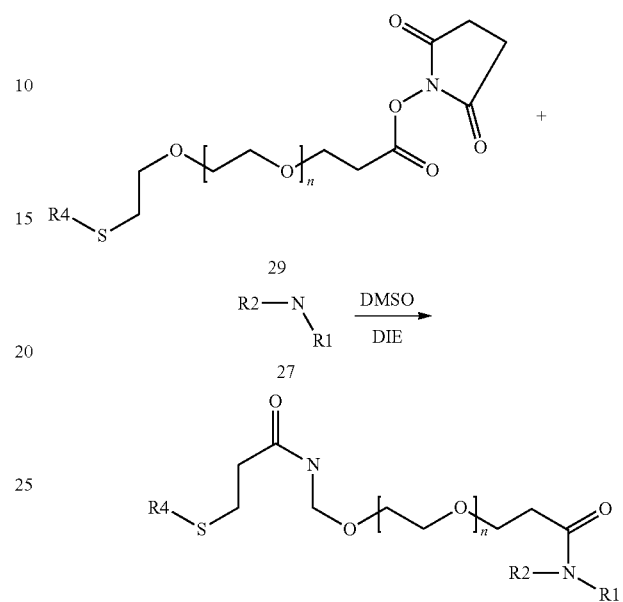

Compounds such as 29 in scheme 2 for which R4 is thioacetyl or 2-dithiopyridyl and having PEG moieties of various lengths are also commercially available (e.g., from Pierce BioScience). Reaction of compounds having the structure of 29 with compounds containing primary or secondary amines such as 27 are conducted in aprotic or As a specific not limiting example for this invention, intermediate 26 is reacted with 31 to produce the maleimide intermediate of 32 as shown in Scheme 3:

Scheme 3

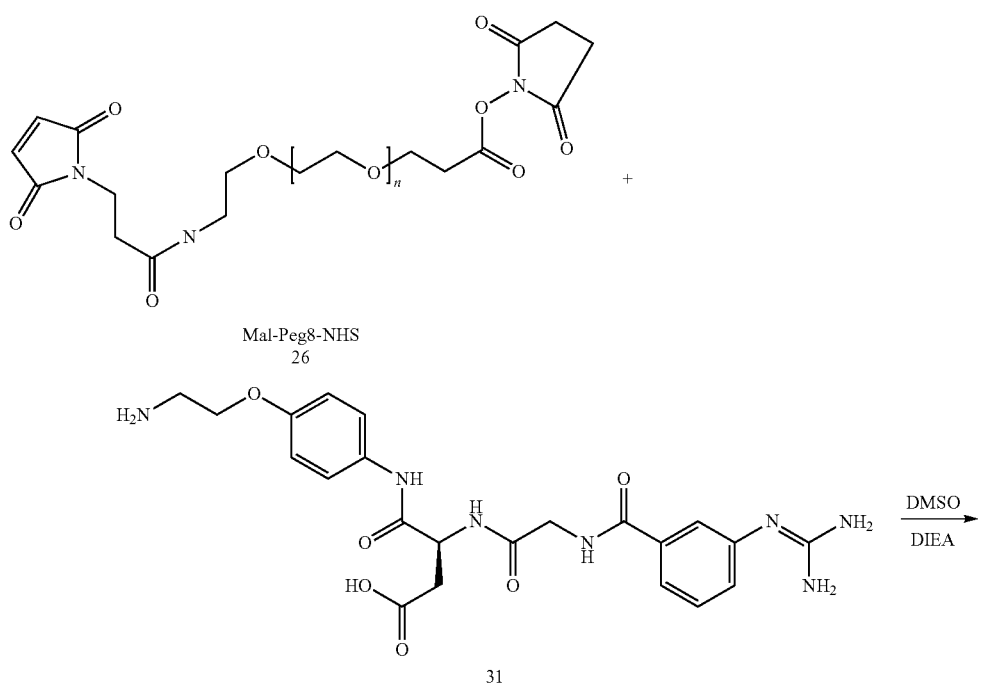

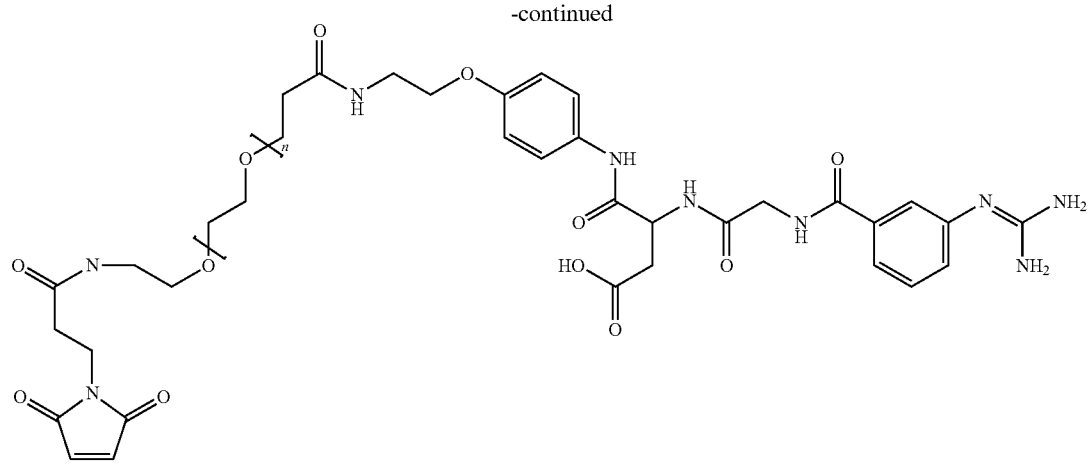
32
In a similar manner, intermediate 26 can be reacted with 33 to produce the maleimide intermediate of 34 as shown in Scheme 4:
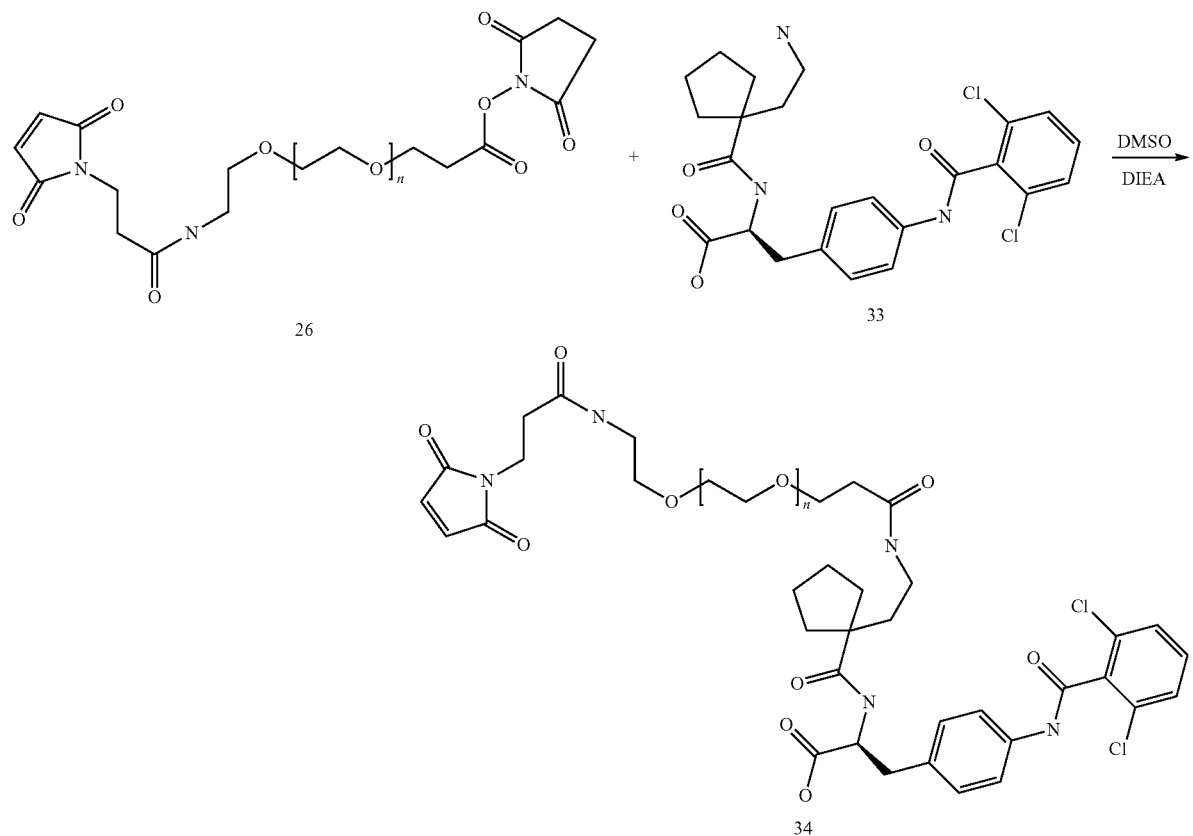
In a similar manner, intermediate 29 can be reacted with 35 to produce the intermediate of 36 as shown in Scheme 5 in which R4 represents either thioacetyl or 2-dithiopyridyl:

Scheme 5
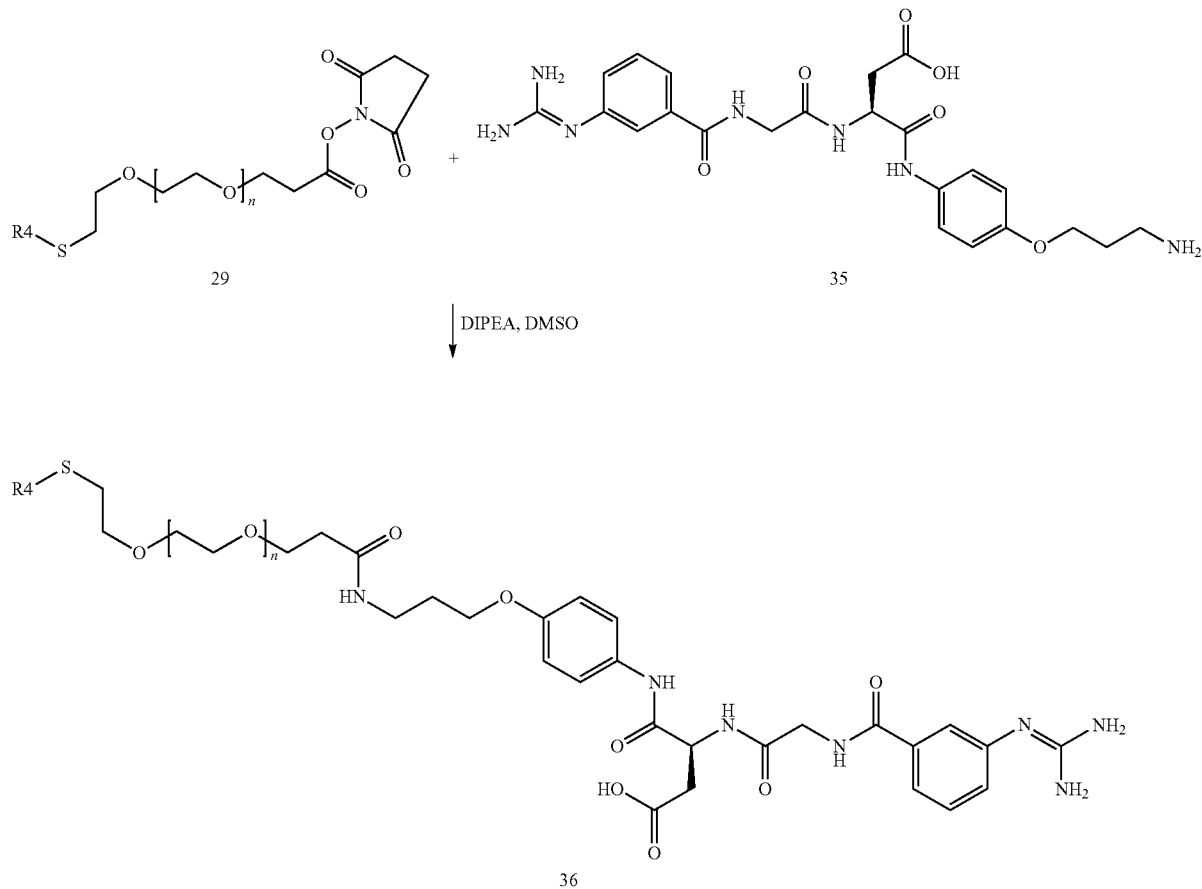
In a similar manner, intermediate 29 can be reacted with 37 to produce intermediate of 38 as shown in Scheme 6 in which R4 represents either thioacetyl or 2-dithiopyridyl:
Scheme 6
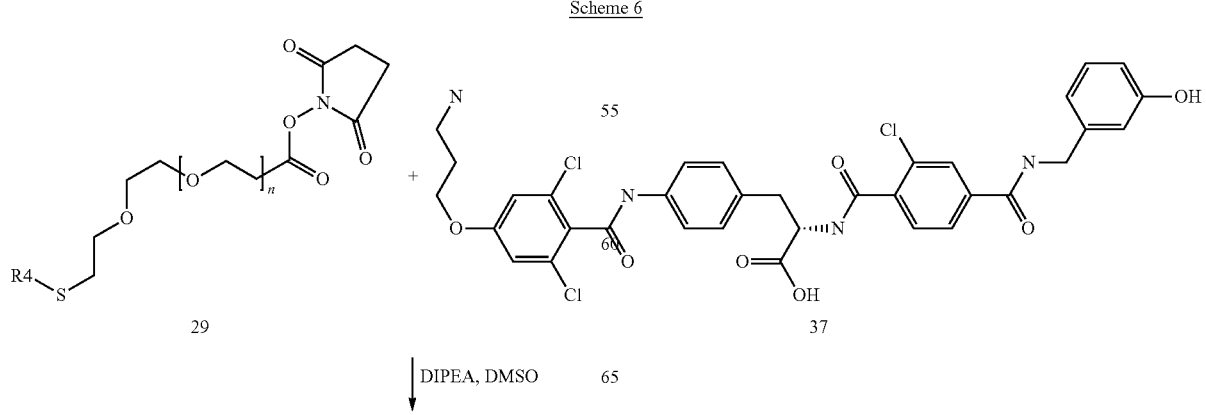

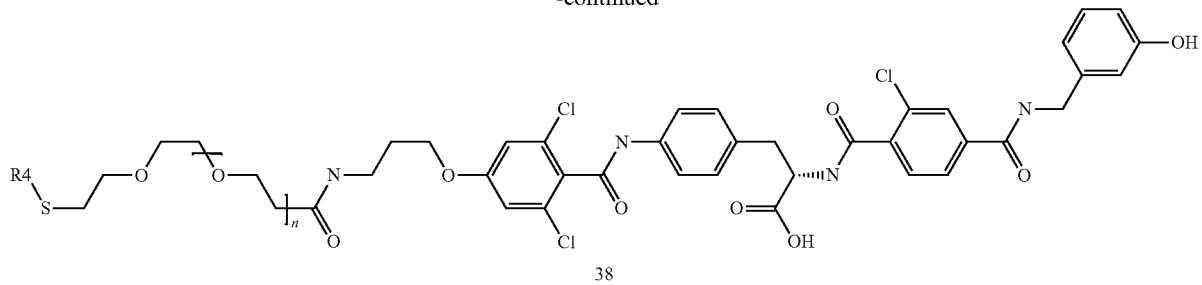

38

For compounds of general structure 26 or 29, different PEG lengths are available or easily made by those skilled in the art; preferably n=8-24. This topic has been thoroughly reported and reviewed (e.g., Chemistry for peptide and protein PEGylation, Advanced Drug Delivery Reviews Volume 54, Issue 4, 17 Jun. 2002, Pages 459-476).

Intermediate 31 can be synthesized in a manner similar to that which has been reported (e.g., Sidduri, A. et al. *Bioorganic & Medicinal Chemistry Letters*, 2002, 12, 2475-2478) as shown in Scheme 7:

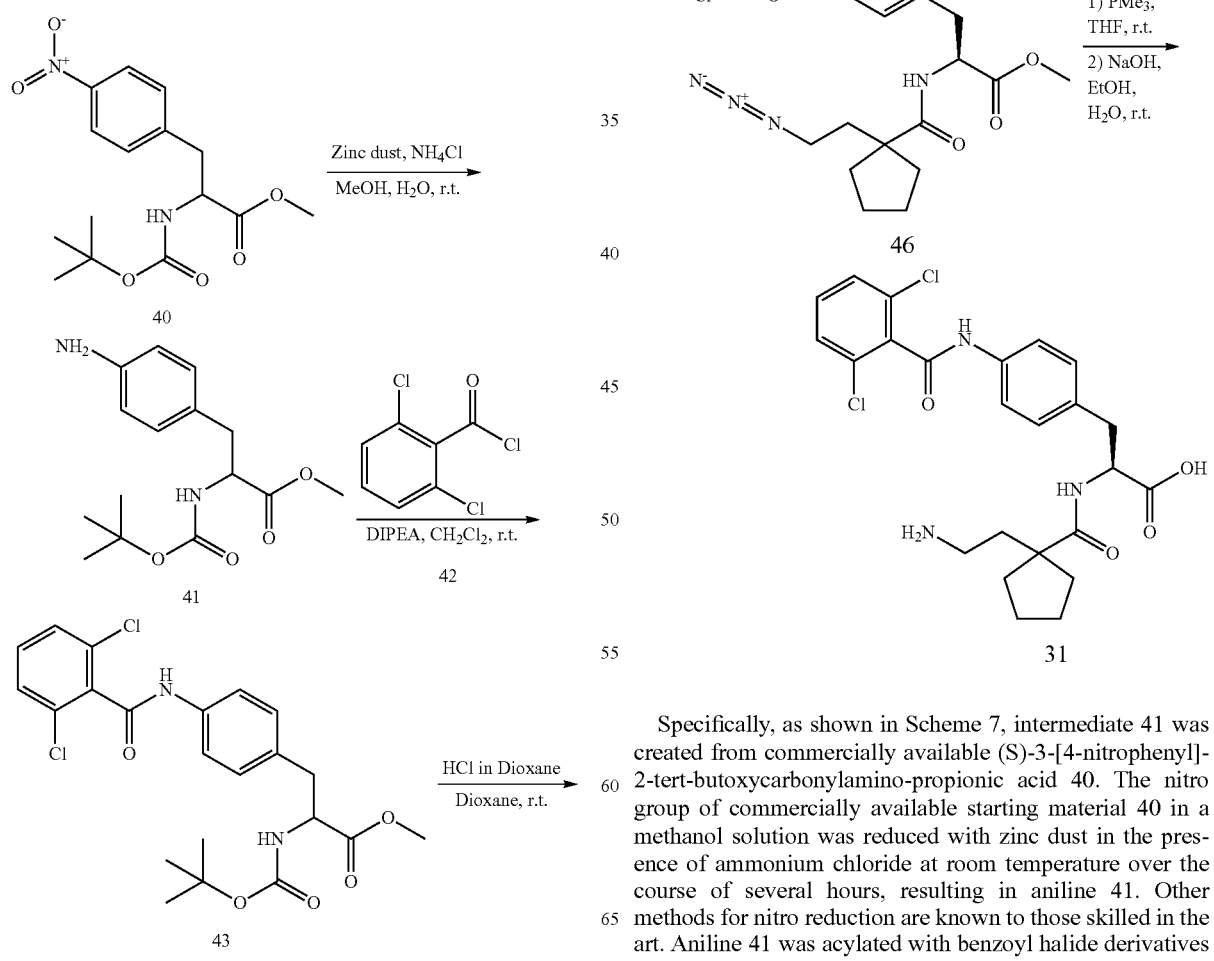

Specifically, as shown in Scheme 7, intermediate 41 was created from commercially available (S)-3-[4-nitrophenyl]-2-tert-butoxycarbonylamino-propionic acid 40. The nitro group of commercially available starting material 40 in a methanol solution was reduced with zinc dust in the presence of ammonium chloride at room temperature over the course of several hours, resulting in aniline 41. Other methods for nitro reduction are known to those skilled in the art. Aniline 41 was acylated with benzoyl halide derivatives such as 2,6-dichlorobenzoyl chloride 42 in aprotic solvent such as dichloromethane in the presence of a base such as di-isopropyl-ethyl amine at room temperature. In this manner, amide 43 was formed. The t-butylcarbonyl (Boc) amine protecting group was removed according to standard methods known to those skilled in the art, such as by treatment with an HCl solution in dioxane at room temperature; this resulted in hydrochloride 44. Hydrochloride 44 was treated with amide bond forming conditions (also well known to those skilled in the art) in the presence of known 1-(2-azido-ethyl)-cyclopentanecarboxylic acid 45 resulting in the production of di-amide 46. The azide group of intermediate 46 was reduced by treatment with tri-alkyl phosphine in an aprotic solvent such as tetrahydrofuran at room temperature. Further, the methyl ester was saponified by treatment with sodium hydroxide in a solvent mixture such as ethanol and tetrahydrofuran at an elevated temperature such as 50° C. and for 15 hours. This process resulted in the formation of intermediate 31 which may also be presented as a zwitterion.

Attachment of the PEG moiety is also possible with intermediate 39, which is synthesized as shown in Scheme 8. Specifically, 3,5-dichlorophenol 47 is protected with tri-isopropylsilylchloride in the presence of a base such as imidazole in a polar aprotic solvent such as DMF before reaction with a strong base such as butyl lithium in anhydrous tetrahydrofuran at low temperatures such as −78 degrees C. The resulting lithium complex is quenched with carbon dioxide added in the form of dry ice resulting in intermediate 48, a benzoic acid derivative.

Intermediate 48 is then chlorinated to form the acyl chloride by treatment in an aprotic solvent such as toluene with sulfonyl chloride (SOCl$_2$). At this time, the acyl chloride is then reacted with amine hydrochloride 49 in the presence of base such as di-isopropylethyl amine (DIPEA) in aprotic solvent such as dichloromethane (DCM), thereby forming intermediate 50. The silyl protecting group of intermediate 50 is removed by treatment with tetrabutyl ammonium fluoride (TBAF) in a protic solvent such as tetrahydrofuran at room temperature. This phenol intermediate is reacted in the presence of a base such as potassium carbonate (K$_2$CO$_3$) in an aprotic solvent such as dimethylformamide (DMF) with 3-N-t-butyl-carbomate-1-bromopropane. In this manner intermediate 52 is formed which upon deprotection with trifluoroacetic acid (TFA) and subsequent hydrolysis with a base such as sodium hydroxide in protic solvent such as ethanol forms intermediate 39:

Scheme 8

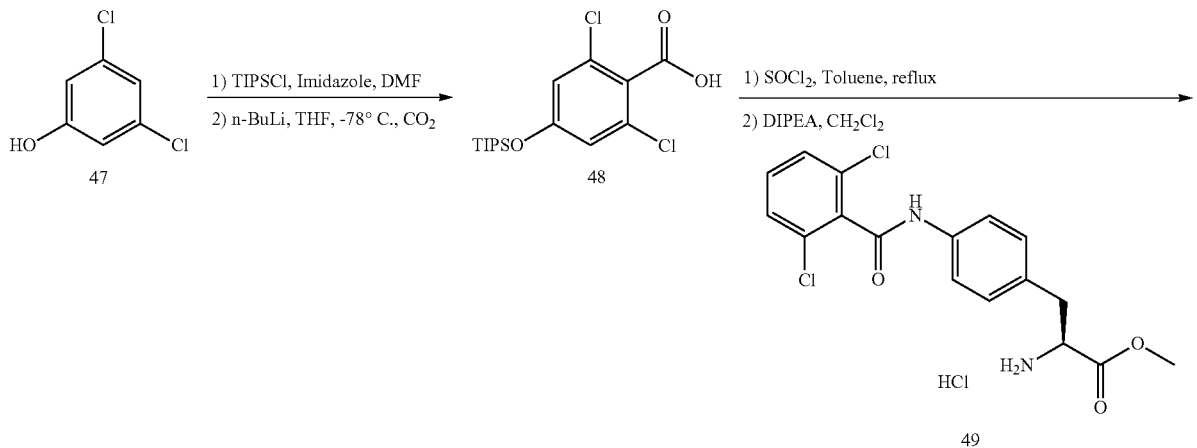

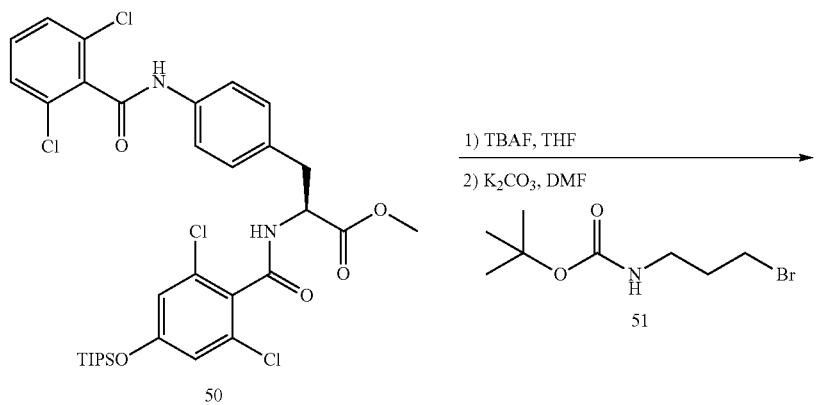

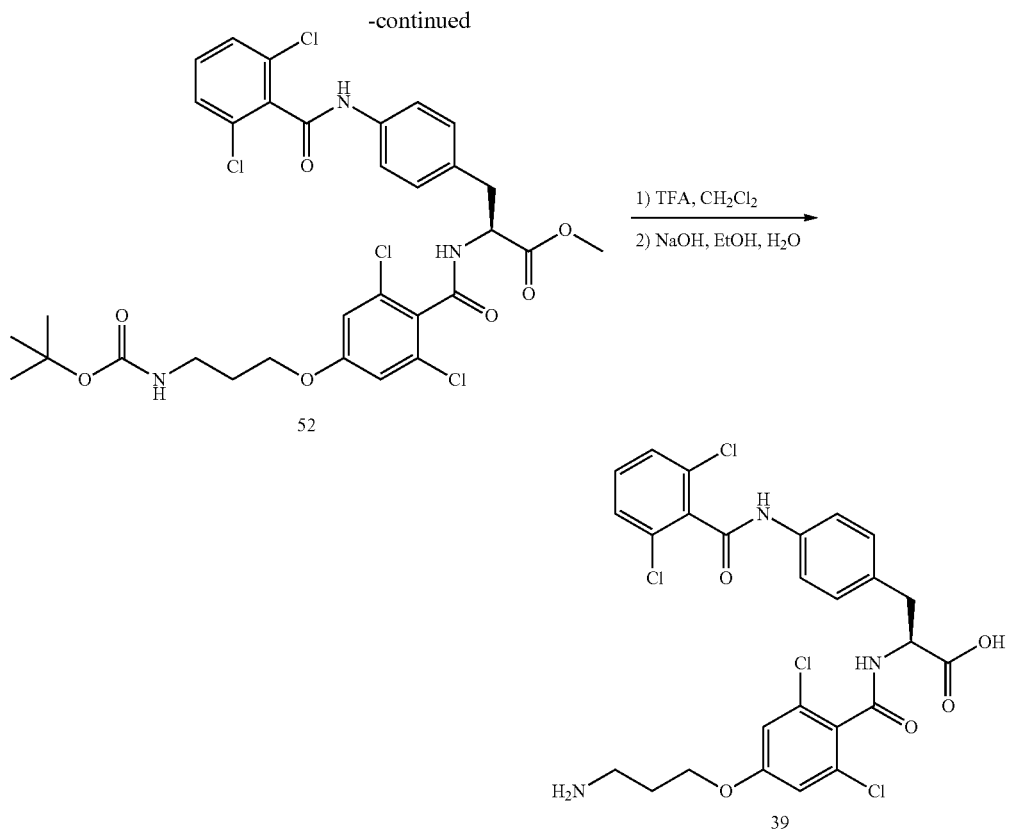

Synthesis of LFA-1 Antagonists Derivatizing Agents

Small molecules which target the LFA-1/ICAM interaction, thereby providing a means of targeting cells which express the ICAM system is shown below in Schemes 11, 12, 13, and 14. As shown in Scheme 11, the primary amide of 3-(3-methoxy)-propanoic acid ester 70 is formed and reduced under standard conditions known to those skilled in the art. Separately, dihydropyrimidine is formed using a Bignelli reaction with urea, acetaldehyde, and 3-oxo-butanoic acid ethyl ester. The pyrimidine of this product is formed by treatment of dihydropyrimidine with 50% nitric acid, resulting in 4,6-dimethyl-2-hydroxy-pyrimidine-5-carboxylic acid ethyl ester.

The chloride of this substance is formed by reaction with $POCl_3$ (phosphorus oxychloride) forming 72. Amine 71 is reacted with chloride 72, forming secondary amine ester 73. At this point, the methoxy group is removed by treatment with a Lewis acid such as boron tribromide in an aprotic solvent to form phenol 74. This phenol 74 is saponified in the presence of an aqueous base followed by application of amide coupling conditions in the presence of S-3-N-t-butyl-carbamate-2-carboxy-diaminopropane hydro chloride (H-DAP(Boc)OMe hydrochloride) thereby forming Intermediate 77. The Boc protecting group is removed under standard conditions followed by saponification of the methyl ester to form the ICAM-1 targeting small molecule 21.

Reaction Scheme 11 for the Following Examples:
LFA-1 Ligand Reagent 1: LFA-1 Ligand Reagent 2, LFA-1 Ligand Reagent 3:

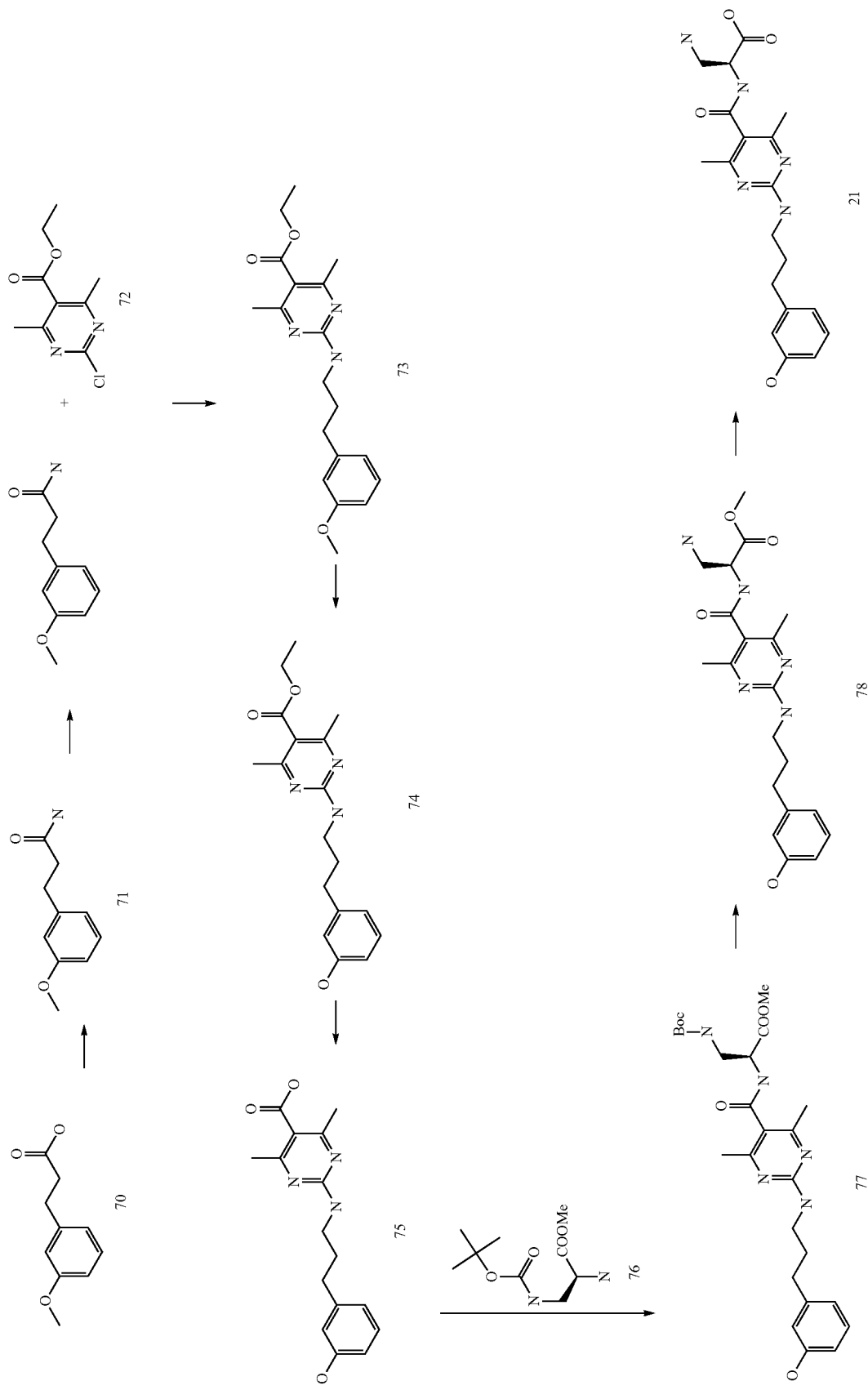
Scheme 11

Other small molecules which target the LFA-1/ICAM interaction, thereby providing a means of targeting cells which express the ICAM system is shown below in Scheme 12. Specifically, 2,6-dichloro-4-triisopropylsilanyloxy-benzoic acid 79 in a aprotic solvent such as toluene is treated with chlorinating reagent thionyl chloride under reflux conditions. Upon work-up, the acyl chloride is then treated with a base such as di-isopropylethylamine and with (S)-3-(4-amino-phenyl)-2-tert-butoxycarbonylamino-propionic acid methyl ester 80 thereby creating amide 81. The Boc amino protecting group is removed under standard conditions and the resulting primary amine 83 is coupled under standard amide bond forming reaction conditions. The methyl ester of 84 has been reported in WO 01/58853; silyl protection of methyl ester 84 was performed by standard conditions well known to those skilled in the art. After coupling and deprotection, amide 88 was then treated with (3-bromo-propyl)-carbamic acid tert-butyl ester. The Boc protecting group is removed under standard conditions followed by saponification of the methyl ester to form the ICAM-1 targeting small molecule 22.

Reaction Scheme 12 for the Following Examples:

LFA-1 Ligand Reagent 4, LFA-1 Ligand Reagent 5, LFA-1 Ligand Reagent 6, LFA-1 Ligand Reagent 7

Scheme 12
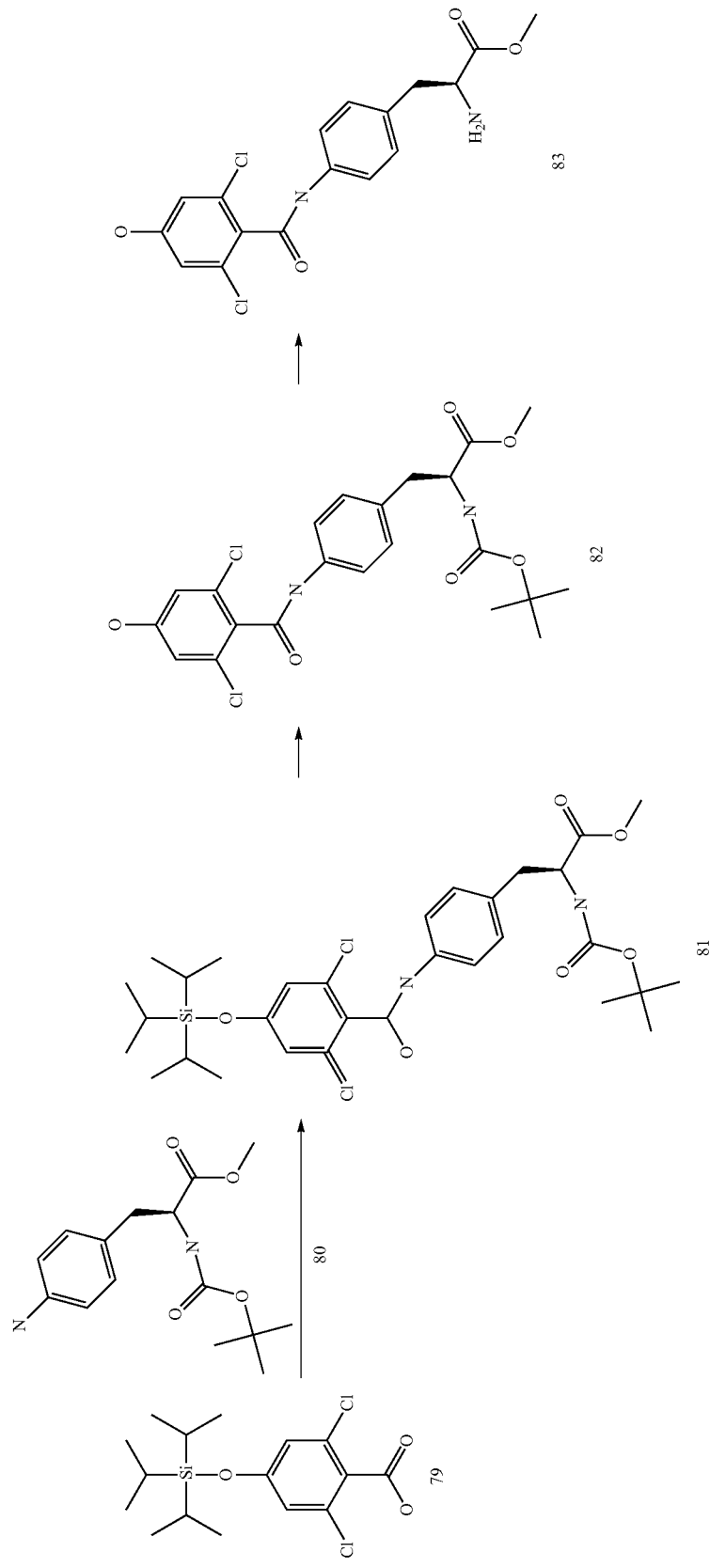

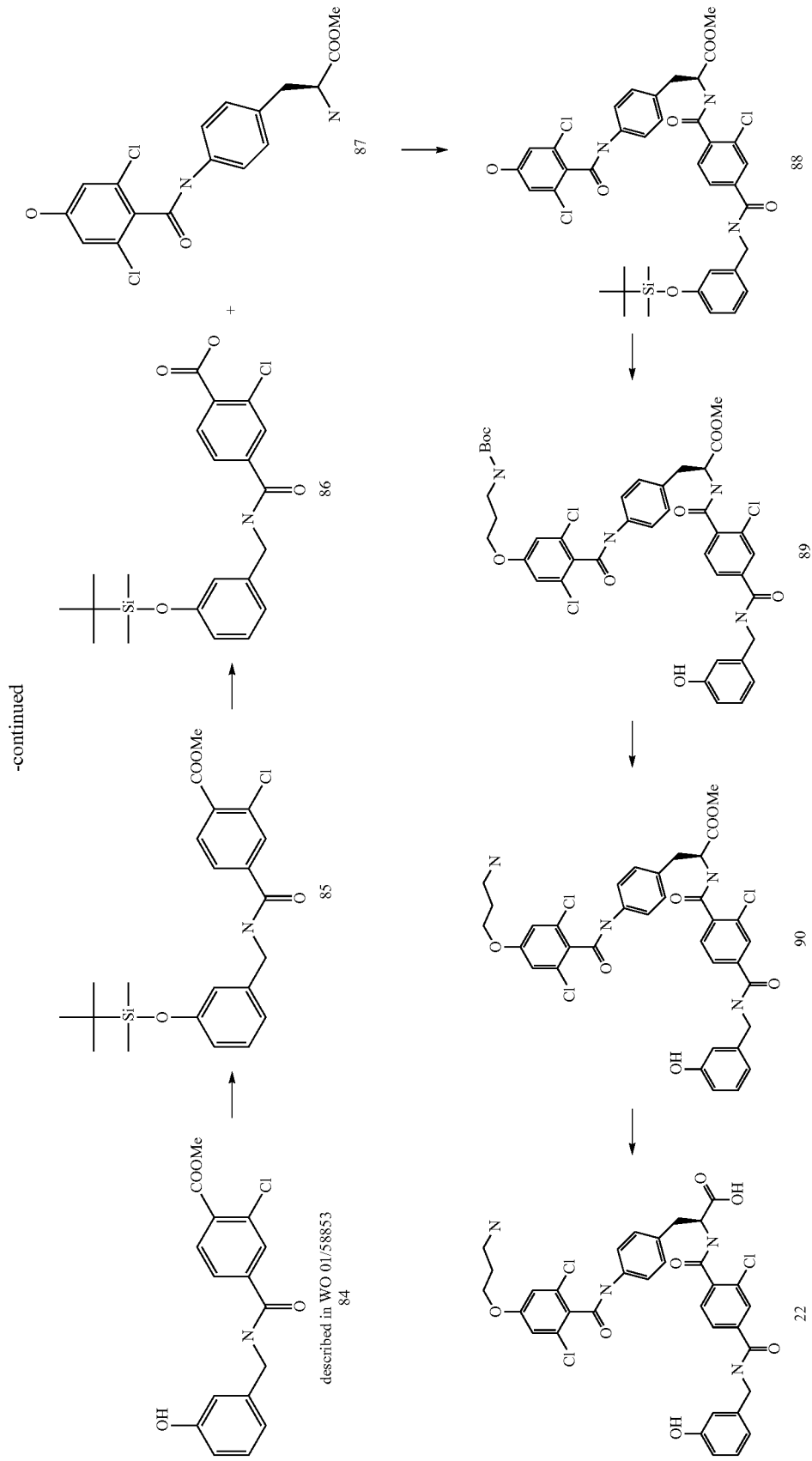

In a similar manner, the production of other small molecules which target the LFA-1/ICAM interaction, thereby providing a means of targeting cells which express the ICAM system is shown below in Scheme 13. Specifically, 3-hydroxymethylbenzoate is alkylated with (3-bromo-propyl)-carbamic acid tert-butyl ester under basic conditions such as in the presence of potassium carbonate solvent mixtures such as acetone and DMF thereby creating intermediate 91. The methyl ester of 91 is saponified and the resulting free acid 92 is coupled under standard amide bond forming conditions with intermediate 93 (Scheme 11) to provide intermediate 94. The Boc protecting group is removed under standard conditions followed by saponification of the methyl ester to form the ICAM-1 targeting small molecule 96.

Reaction Scheme 13 for the Following Example:
LFA-1 Ligand Reagent 8

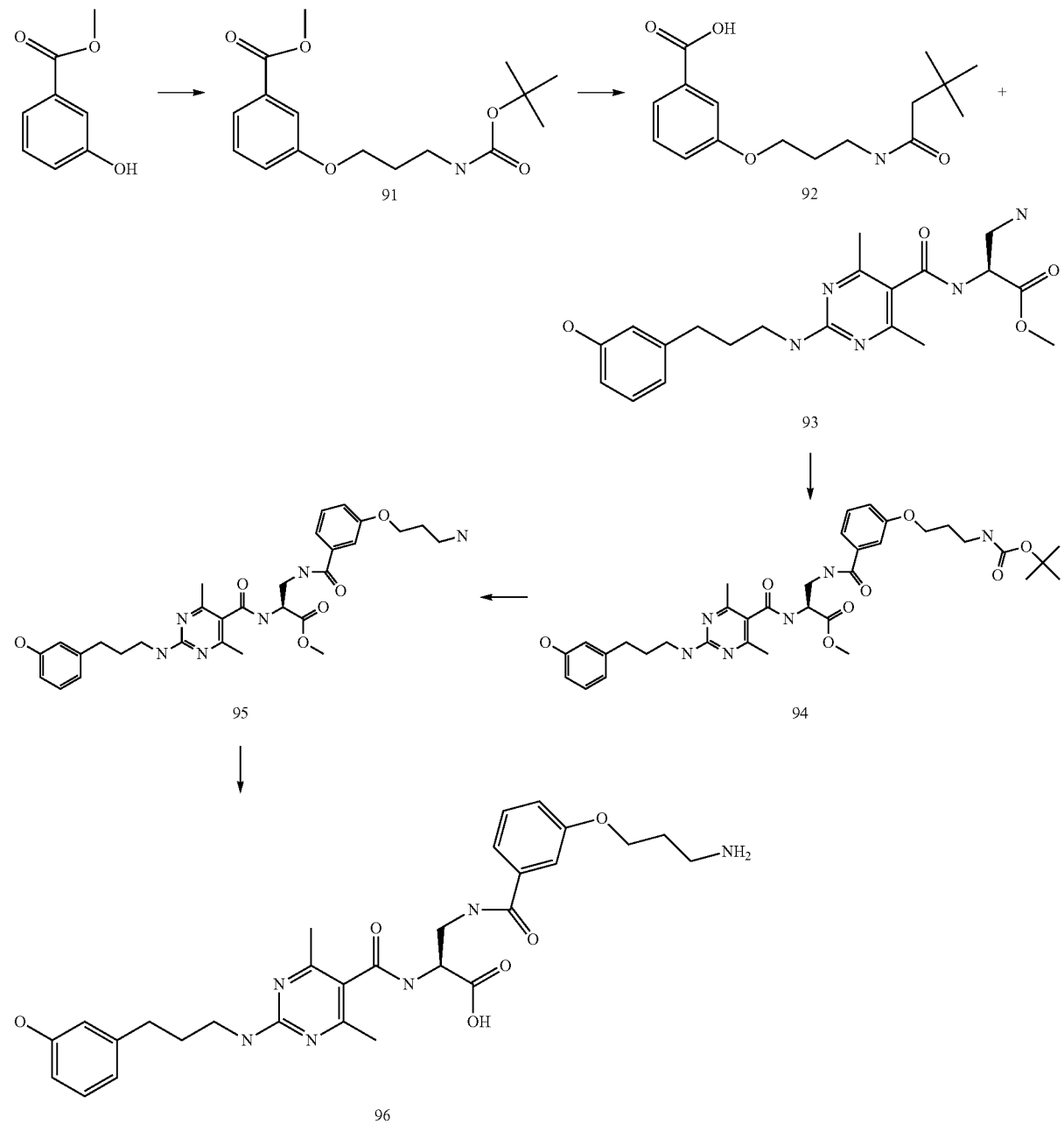

A similar sequence of reactions is used to create compound 102 shown below in Scheme 14 which targets the LFA-1/ICAM interaction, thereby providing a means of targeting cells which express the ICAM system. Instead of starting with 3-hydroxymethylbenzoate, the starting material of 3,5-dihydroxymethylbenzoate 97 is used in a similar sequence to create intermediate 103 also shown in Scheme 14.
Reaction Scheme 14 for the Following Examples:
LFA-1 Ligand Reagent 9, LFA-1 Ligand Reagent 10
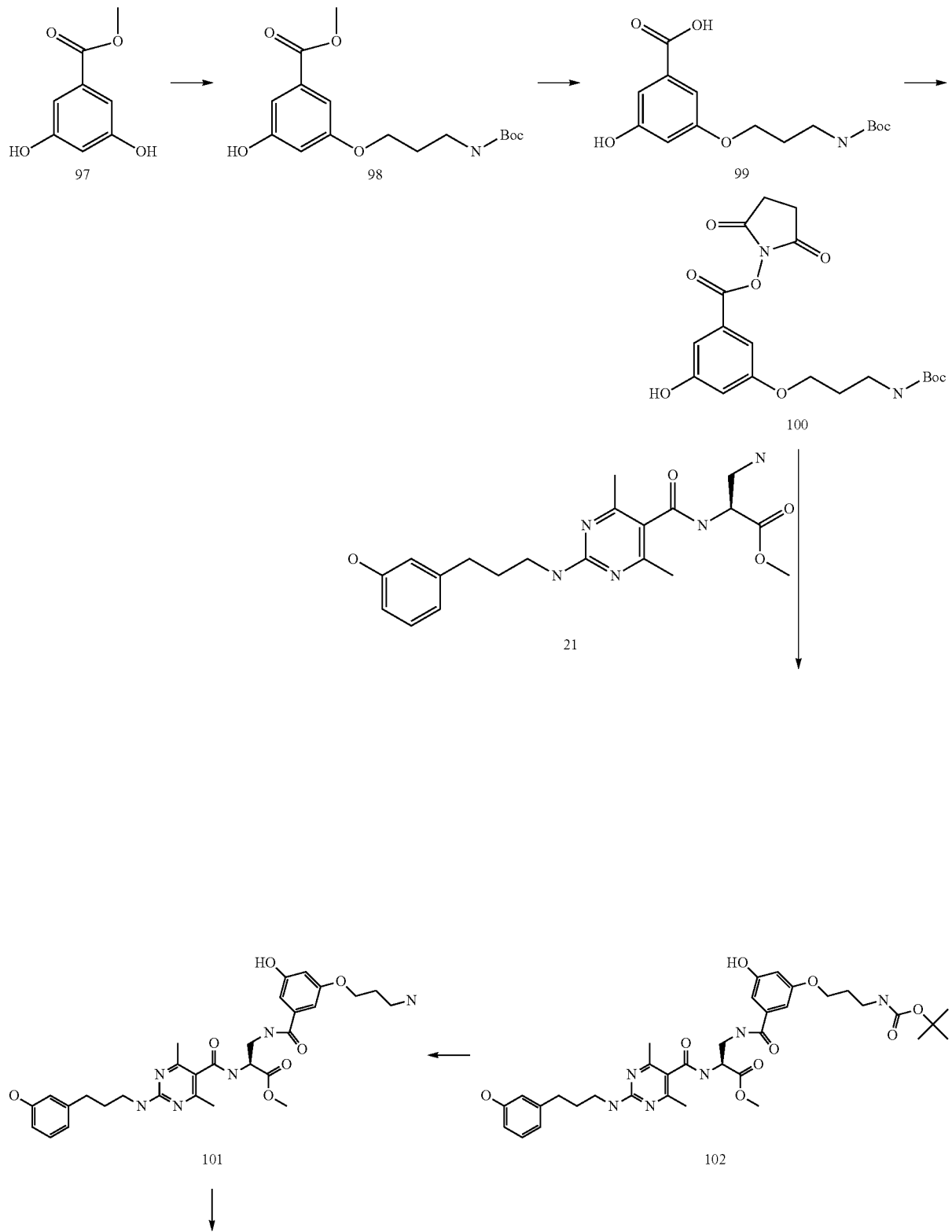

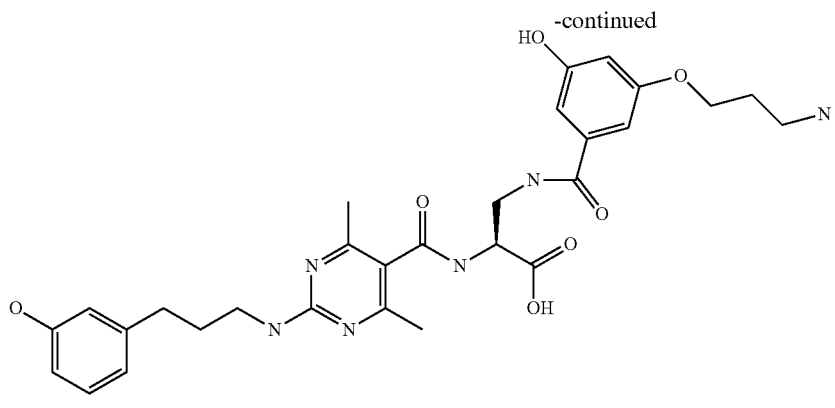

103

Utility

The compounds of formula I are useful in delivering conjugated moieties such as therapeutics, small molecules, peptides, nucleic acids, fluorescent moieties, and polymers to target cells expressing LFA-1 integrin receptor complexes for various therapeutic and other applications. Accordingly, the compounds of formula I may be used for treating various diseases and conditions that are associated with the expression or overexpression of LFA-1. Such diseases and conditions may include inflammation, cancer, and metabolic related diseases.

In particular embodiments, the present invention comprises a method of treating or preventing cancer in a mammal (preferably a human) in need of such treatment, wherein the method comprises administering a therapeutically effective amount of a compound of formula I. In a further embodiment there is provided the use of a compound of formula I for the treatment or prophylaxis of inflammation, cancer, or a metabolic disease or condition. In a further embodiment there is provided the use of a compound of formula I for the the preparation of a medicament for the treatment or prophylaxis of inflammation, cancer, or a metabolic disease or condition.

Such compositions can be administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations as the minimum amount necessary to treat or prevent the disease or condition (e.g. inhibit the expression of a target protein) and avoid unacceptable toxicity. For example, such amount may be below the amount that is toxic to normal cells, or the mammal as a whole. The compositions containing a compound of formula I of the invention may be administered by parenteral, intraperitoneal, and intrapulmonary administration. Parenteral infusions include intramuscular, intravenous, intraarterial, intraperitoneal, or subcutaneous administration.

EXAMPLES

The invention will be more fully understood by reference to the following examples. They should not, however, be construed as limiting the scope of the invention.

Reagents were purchased from Aldrich, Sigma, and Pierce BioScience or other suppliers as indicated below and used without further purification. The purification of multi-milligram to multi-gram scale was conducted by methods known to those skilled in the art such as elution of silica gel flash column. Preparative flash column purifications were also effected in some cases by use of disposable pre-packed multigram silica gel columns (RediSep) eluted with a CombiFlash system. Biotage™ and ISCO™ are also flash column instruments that may be used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7T FT-Mass Spectrometer. Final compounds were also characterized by high resolution mass spectrometry using a LTQ CL Orbitrap sold by Thermo Electron.

Abbreviations used herein are as follows:
AIBN 2,2'-azobisisobutyronitrile
Bu butyl
DCE 1,2-dichloroethane
DCM dichloromethane
DBU 1,8-diazabicyclo[5.4.0]undec-7-ene
DIAD diisopropyl azodicarboxylate DIEA diethylamine
DIPEA diisopropylethylamine
DMF N,N-dimethylformamide
DMSO dimethylsulfoxide
EDC-HCl 1-ethyl-3-(3-dimethyllaminopropyl)carbodiimide hydrochloride
EtOAc ethyl acetate
EtOH ethyl alcohol
FCC flash column chromatography
h hour
HBTU O-(benzotriazol-1-yl)-N,N,N',N'-tetramethyluroniumhexafluorophosphate
HOBt hydroxybenzotriazole
HPLC high pressure liquid chromatography
HRMS high resolution mass spectra
LRMS low resolution mass spectra
LC liquid chromatography
L-Pro L-proline
MCPBA meta-chloroperoxybenzoic acid
MeOH methyl alcohol
MW microwave
NIS N-iodosuccinimide
NBS N-bromosuccinimide
NMP 1-methyl-2-pyrrolidinone
PdCl$_2$(dppf) [1,1'-Bis(diphenylphosphino)ferrocene]dichloropalladium(II)
PEGn Polyethylene glycol repeating n times (e.g., PEG2=—OCH2CH2OCH2CH2-)
PG protecting group
PyBroP bromo-tris-pyrrolidino-phosphonium hexafluorophosphate
rt room temperature
TBAF tetrabutylammonium fluoride
TBDMS tert-butyl-dimethylsilyl
TBTU 2-(1H-benzotriazole-1-yl)-1,1,3,3-tetramethyluronium tetrafluoroborate
TMS trimethylsilyl
TEA triethylamine
TFA trifluoroacetic acid
THF tetrahydrofuran
TLC thin layer chromatography
TPP triphenylphosphine Synthesis of Small Molecule LFA-1 Antagonists and/or Dual LFA-1/MAC-1 Antagonists to the ICAM-1 Receptor for Use as Targeting Agents Part 1: Preferred Intermediates Preparation of 3-(3-methoxy-phenyl)-propionamide

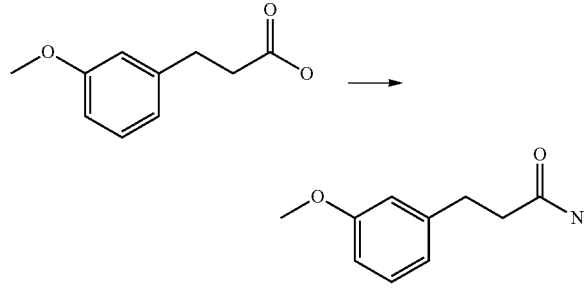

A solution of 3-(3-methoxy-phenyl)-propionic acid (15 g, 83.2 mmol) and 4-methyl-morpholine (10.1 ml, 91.56 mmol) in THF (150 ml) was cooled to 0° C. (ice-water bath), and iso-propyl chloroformate (1M in toluene, 91.6 ml, 91.56 mmol) was added over 20 minutes. The mixture was stirred for another 30 minutes at 0° C., followed by dropwise addition of 7N NH$_3$/MeOH (24 ml, 168 mmol). The mixture was allowed to warm up to room temperature and stirred for 2 h. It was quenched with 10% aq K$_2$CO$_3$ and extracted with EtOAc. The organic extracts were combined, washed with water and brine, dried over sodium sulfate, filtered and evaporated to give the desired amide (11.15 g, 75% yield). MS m/e 179.9 (M+H$^+$).

Preparation of 3-(3-methoxy-phenyl)-propylamine

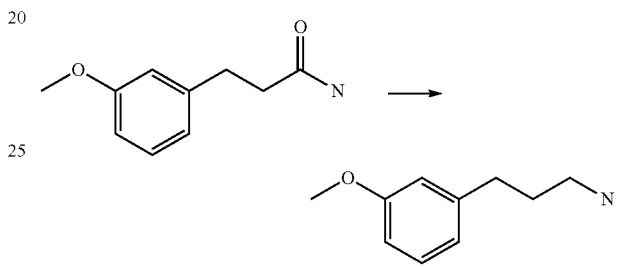

BH$_3$ in THF (2.2 g, 188 mmol) was added at room temperature to a solution of 3-(3-methoxy-phenyl)-propionamide (11.15 g, 62.26 mmol) in THF (100 ml). The solution was heated to reflux for 4 h, cooled to room temperature and quenched with MeOH (50 ml). The solution was heated to reflux for 30 min, concentrated, treated with water, and extracted with EtOAc. The extract was washed with 10% aqK$_2$CO$_3$, water and brine, dried over Na$_2$SO$_4$, filtered and evaporated to give title compound (9.26 g, 90% yield). MS m/e 165.9 (M+H$^+$).

Preparation of 4,6-Dimethyl-2-hydroxy-1,6-dihydropyrimidine-5-carboxylic acid ethyl ester

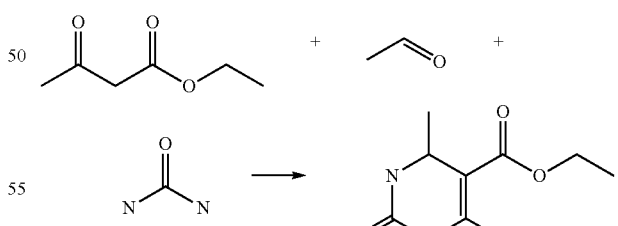

A mixture of 3-oxo-butanoic acid ethyl ester (16.27 g, 125 mmol), acetaldehyde (5.51 g, 125 mmol), urea (7.51 g, 125 mmol), and glacial acetic acid (20 drops) in ethanol (35 ml) was heated to 90° C. overnight in a 350 ml pressure flask. The mixture was diluted with water. The precipitate was collected by filtration, washed with water and air-dried to afford the desired product (17.68 g, 71% yield). MS m/e 198.8 (M+H$^+$).

Preparation of 4,6-dimethyl-2-hydroxy-pyrimidine-5-carboxylic acid ethyl ester

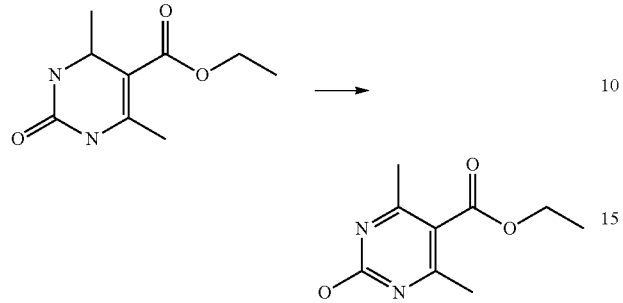

4,6-Dimethyl-2-hydroxy-1,6-dihydro-pyrimidine-5-carboxylic acid ethyl ester (34.63 g, 174.7 mmol) was added in portions to an ice-cooled solution of 50% nitric acid (120 ml) over 5 minutes. The solution was stirred at 0° C. for 10 minutes, poured into ice water (500 ml), neutralized with solid $K_2CO_3$ and extracted with chloroform. The combined organic layers were washed with water and brine, dried over $Na_2SO_4$, filtered, and concentrated to afford title compound (21.9 g, 71% yield). MS m/e 197.1 (M+H$^+$).

Preparation of 2-Chloro-4,6-dimethyl-pyrimidine-5-carboxylic acid ethyl ester

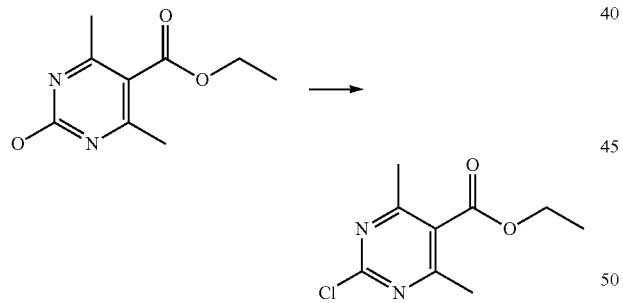

To a solution of POCl$_3$ (106 ml) and DIEA (65 ml) was added 4,6-dimethyl-2-hydroxy-pyrimidine-5-carboxylic acid ethyl ester (21.9 mg, 111.6 mmol). The mixture was heated to 110° C. for 2 h. Excess POCl$_3$ and DIEA were removed by evaporation under reduced pressure. The residue was dissolved in EtOAc (1.21) and treated with decolorizing carbon. After filtration, the solution was washed with 1N NaOH, water and brine. The organic layer was dried over Na$_2$SO$_4$. filtered and concentrated. The crude residue was purified by flash chromatography with a 0-30% EtOAc in hexane gradient to afford the desired product (9.33 g, 39% yield).

Preparation of 2-[3-(3-methoxy-phenyl)-propylamino]-4,6-dimethyl-pyrimidine-5-carboxylic acid ethyl ester

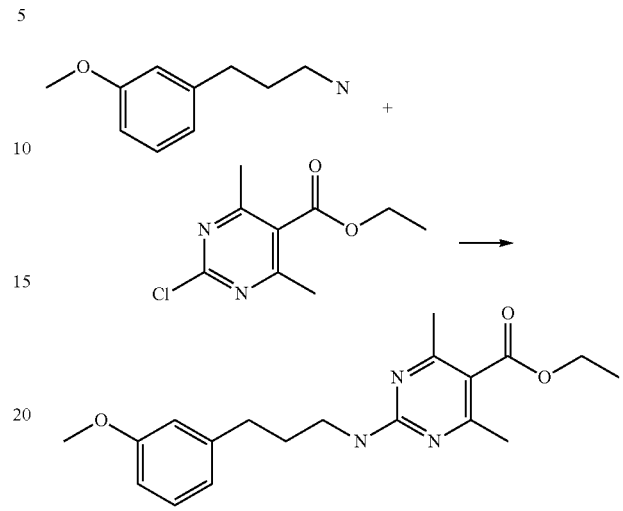

A mixture of 3-(3-methoxy-phenyl)-propylamine (2.31 g, 13.98 mmol), 2-chloro-4,6-dimethyl-pyrimidine-5-carboxylic acid ethyl ester (2 g, 9.32 mmol) in EtOH (12 ml) was microwaved at 160° C. for 1.5 h. The reaction mixture was cooled to room temperature, quenched with 10% $K_2CO_3$ and extracted with EtOAc. The organic layer was washed with brine, dried over Na$_2$SO$_4$, filtered and concentrated. The residue was purified by flash chromatography with 30% EtOAC in hexane to afford the desired product (2.42 g, 76% yield). MS m/e 344.1 (M+H$^+$).

Preparation of 2-[3-(3-hydroxy-phenyl)-propylamino)-4,-dimethyl-pyrimidine-5-carboxylic acid ethyl ester

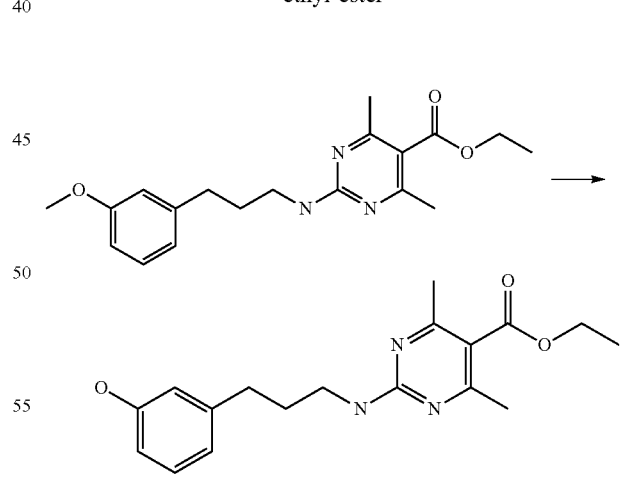

A solution of 2-[3-(3-methoxy-phenyl)-propylamino]-4,6-dimethyl-pyrimidine-5-carboxylic acid ethyl ester (2.42 g, 7.05 mmol) DCM (50 ml) was cooled in an ice-water bath and BBr$_3$/DCM (1M, 14.1 ml, 14.1 mmol) was added dropwise. The resulting solution was allowed to warm up to room temperature and stirred at room temperature for 2 h. The solution was quenched with ice water and extracted with DCM. The organic layers were combined, washed with water and brine, dried over MgSO₄, filtered, and concentrated to afford the desired product (2 g, 86% yield). MS m/e 330.1 (M+H⁺).

Preparation of (S)-3-tert-butoxycarbonylamino-2-({2-[3-(3-hydroxy-phenyl)-propylamino]-4,6-dimethyl-pyrimidine-5-carbonyl}-amino)-propionic acid methyl ester

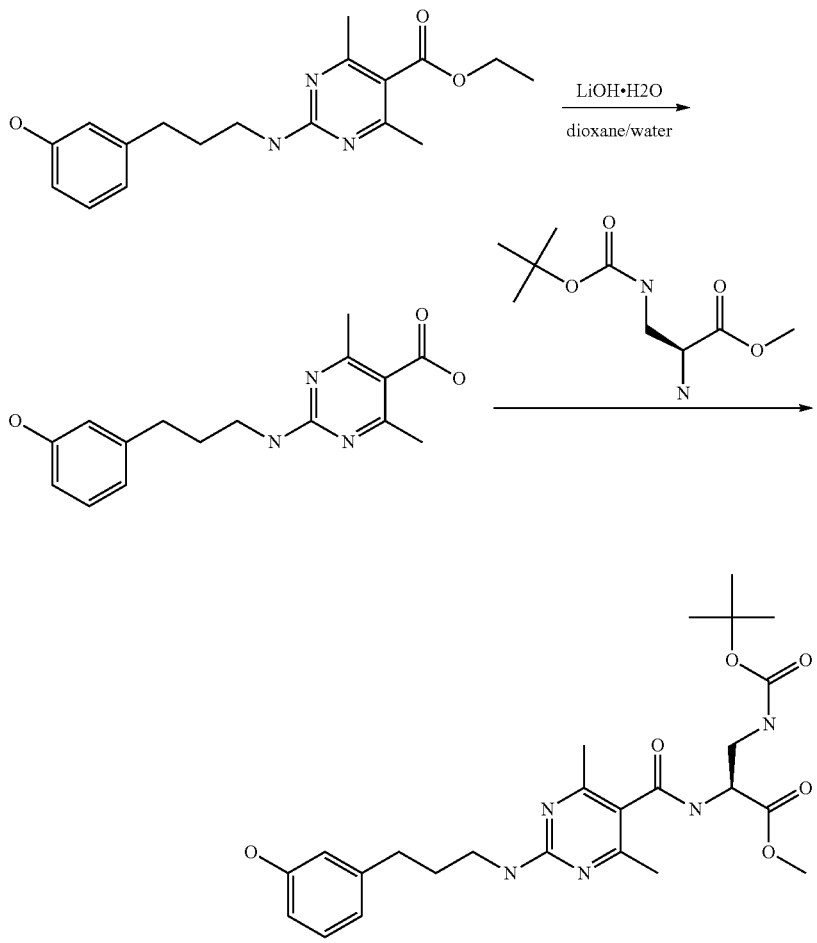

A solution of 2-[3-(3-hydroxy-phenyl)-propylamino]-4,5-dimethyl-pyrimidine-5-carboxylic acid ethyl ester (2.0 g, 6.0 mmol) in dioxane (30 ml) was treated with a solution of lithium hydroxide monohydrate (6.3 g, 150 mmol) in water (30 ml). The mixture was stirred at 90° C. for 12 h, then cooled to room temperature and quenched with aqueous potassium hydrogen sulfate to adjust the pH to ~2-4. The resulting solution was extracted with EtOAc. The organic extracts were combined, washed with brine, dried over sodium sulfate, filtered and concentrated to give the acid (1.76 g) which was not purified but directly submitted to the next step. To a solution of 2-[3-(3-hydroxy-phenyl)-propylamino]-4,6-dimethyl-pyrimidine-5-carboxylic acid (1.76 g, 5.84 mmol) in anhydrous DMF (60 ml) was added Et₃N (2.5 ml, 7.0 mmol), HBTU (2.66 g, 7.01 mmol), HOBT (0.95 g, 7.01 mmol), and H-DAP(Boc)OMe hydrochloride (1.79 g, 7.01 mmol). The mixture was stirred at room temperature for 3 h, diluted with brine (200 ml) and extracted with ethyl acetate. The combined organic layers were washed with 1:1 saturated sodium bicarbonate/brine and brine, then dried over Na₂SO₄, filtered, and concentrated under reduced pressure. The crude residue was purified by flash chromatography with a 40-100% EtOAc in hexane gradient to give the title compound (2.66 g, 91% yield). MS m/e 501.9 (M+H⁺).

Preparation of (S)-3-Amino-2-({2-[3-(3-hydroxy-phenyl)-propylamino]-4,6-dimethyl-pyrimidine-5-carbonyl}-amino)-propionic acid methyl ester hydrochloride

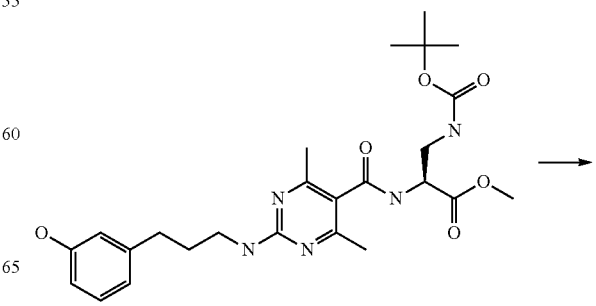

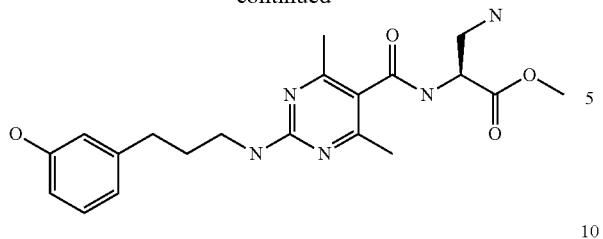

To a solution of (S)-3-tert-Butoxycarbonylamino-2-({2-[3-(3-hydroxy-phenyl)-propylamino]-4,6-dimethyl-pyrimidine-5-carbonyl}-amino)-propionic acid methyl ester (2.66 g, 5.30 mmol) in MeOH (10 ml) was added 4.0 M HCl in dioxane (20 mL). After one hour the mixture was concentrated and azeotroped with MeOH. The product was triturated with ether, filtered, and washed with ether to afford the title compound (2.16 g, 93% yield). MS m/e 401.9 (M+H$^+$).

Preparation of (S)-3-amino-2-({2-[3-(3-hydroxy-phenyl)-propylamino]-4,6-dimethyl-pyrimidine-5-carbonyl}-amino)-propionic acid hydrochloride; LFA-1 Ligand 1

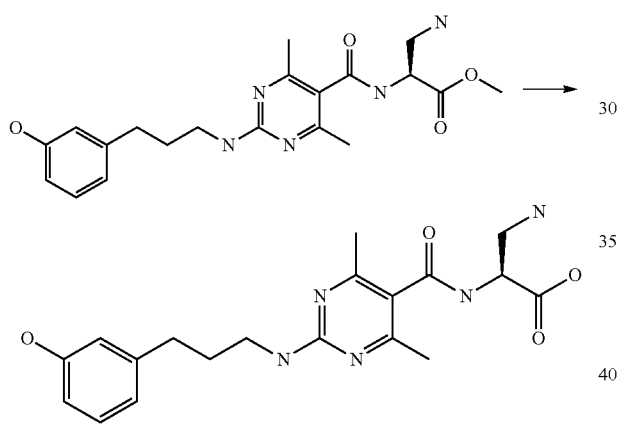

S)-3-Amino-2-({2-[3-(3-hydroxy-phenyl)-propylamino]-4,6-dimethyl-pyrimidine-5-carbonyl}-amino)-propionic acid methyl ester hydrochloride (50 mg, 0.114 mmol) was added to aqueous solution of LiOH (13 mg, 0.57 mmol in 2 mL of water) and the resulting suspension was stirred at room temperature overnight. Then the reaction mixture was neutralized with 1N hydrochloric acid and lyophilized. This material was used with any additional purification for the next step.

Preparation of 3-(3-tert-butoxycarbonylamino-propoxy)-benzoic acid methyl ester

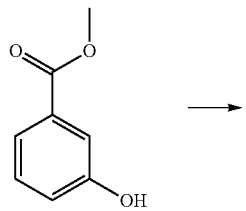

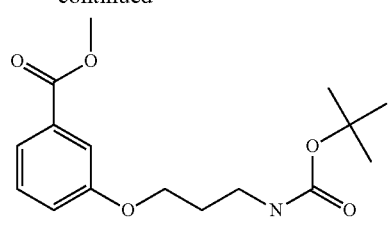

3-Hydroxymethylbenzoate (500 mg, 3.29 mmol), (3-bromo-propyl)-carbamic acid tert-butyl ester (861 mg, 1.1 eq.) and potassium carbonate (2.3 g, 5 eq.) were combined in a mixture of acetone (10 mL) and DMF (10 mL). The reaction mixture was stirred at 75° C. overnight. The insoluble material was filtered and discarded and the filtrate was concentrated under reduced pressure, diluted with ethyl acetate and washed with water and brine, followed by drying over anhydrous sodium sulfate. Flash chromatography on silica gel using ethyl acetate and hexanes afforded 900 mg of the title compound. HRMS m/e 332.1466 (M+Na)$^+$ Preparation of 3-(3-tert-butoxycarbonylamino-propoxy)-benzoic acid

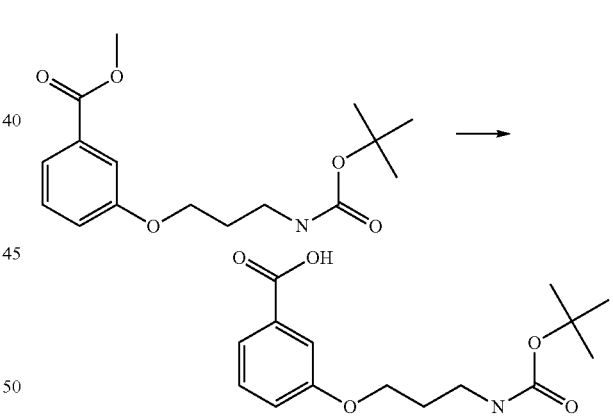

To a solution of 3-(3-tert-butoxycarbonylamino-propoxy)-benzoic acid methyl ester (900 mg) in methanol (3 mL) was added a solution of LiOH (334 mg, 5 eq.) in water (3 mL) and the resulting reaction mixture was stirred at 45° C. overnight. Then the reaction mixture was acidified with 1 N HCl to pH 3 and immediately extracted with ethyl acetate. The organic phase was washed with brine and dried over anhydrous sodium sulfate. It was then concentrated under reduced pressure and crystallized from ethyl acetate to afford 600 mg of the title compound. HRMS m/e 318.1311 (M+Na)$^+$ Preparation of (S)-3-[3-(3-tert-butoxycarbonylamino-propoxy)-benzoylamino]-2-({2-[3-(3-hydroxy-phenyl)-propylamino]-4,6-dimethyl-pyrimidine-5-carbonyl}-amino)-propionic acid methyl ester

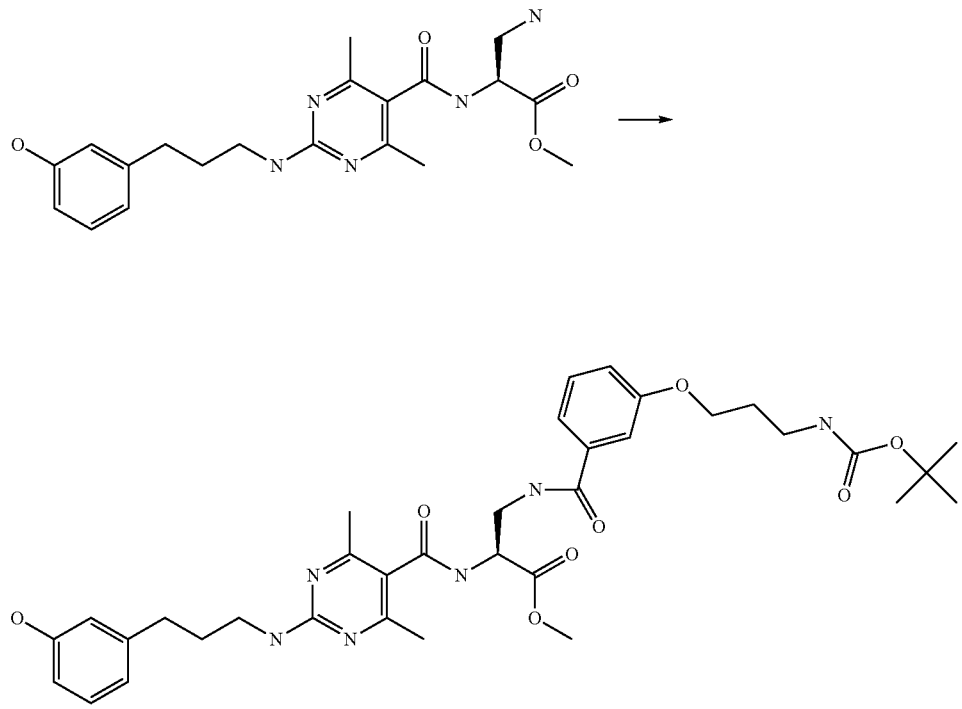

To a solution of 3-(3-tert-butoxycarbonylamino-propoxy)-benzoic acid (57 mg, 0.193 mmol) in DMF (1 mL) were added HBTU (78 mg, 1.05 eq.), DIEA (172 µL, 5 eq.) and (S)-3-amino-2-({2-[3-(3-hydroxy-phenyl)-propylamino]-4,6-dimethyl-pyrimidine-5-carbonyl}-amino)-propionic acid methyl ester hydrochloride (100 mg, 0.194 mmol). The resulting reaction mixture was stirred at room temperature for 4 h. It was then diluted with ethyl acetate, washed with water and brine and dried over anhydrous sodium sulfate. Flash chromatography on silica gel using methanol/methylene chloride afforded 97 mg of the title compound.

HRMS m/e 679.3447 (M+H)$^+$

Preparation of (S)-3-[3-(3-amino-propoxy)-benzoylamino]-2-({2-[3-(3-hydroxy-phenyl)-propylamino]-4,6-dimethyl-pyrimidine-5-carbonyl}-amino)-propionic acid methyl ester hydrochloride

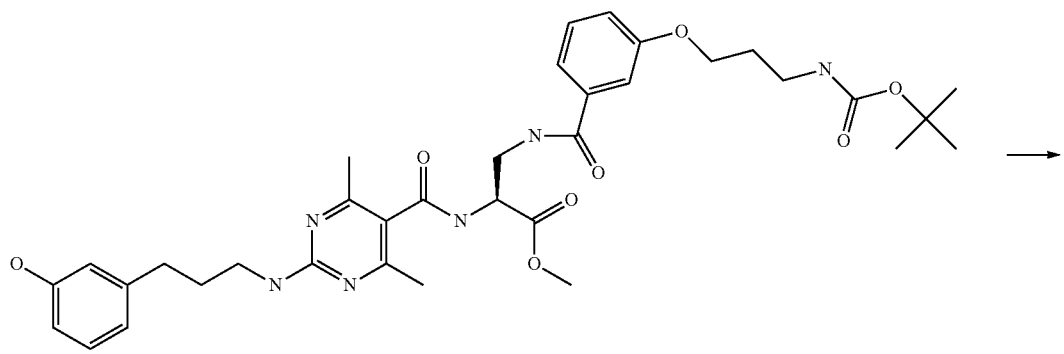

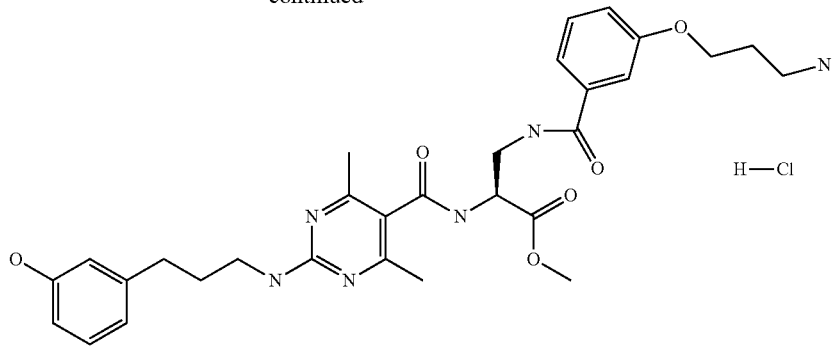

Trimethylsilyl chloride (177 μL) was added to methanol (2 mL) and the resulting mixture was stirred at room temperature for 5 min. Then it was added to (S)-3-[3-(3-tert-butoxycarbonylamino-propoxy)-benzoylamino]-2-({2-[3-(3-hydroxy-phenyl)-propylamino]-4,6-dimethyl-pyrimidine-5-carbonyl}-amino)-propionic acid methyl ester (94.6 mg, 0.139 mmol) and the resulting reaction mixture was stirred at room temperature over the weekend. Then it was concentrated under reduced pressure and triturated with diethyl ether to afford 84.8 mg of the title compound. HRMS m/e 579.2925 (M+H)⁺

Preparation of (S)-3-[3-(3-amino-propoxy)-benzoylamino]-2-({2-[3-(3-hydroxy-phenyl)-propylamino]-4,6-dimethyl-pyrimidine-5-carbonyl}-amino)-propionic acid LAF-1 Ligand 2

(S)-3-[3-(3-Amino-propoxy)-benzoylamino]-2-({2-[3-(3-hydroxy-phenyl)-propylamino]-4,6-dimethyl-pyrimidine-5-carbonyl}-amino)-propionic acid methyl ester hydrochloride (82.6 mg, 0.134 mmol) was dissolved in methanol (1 mL) and 2 M NaOH (336 μL, 5 eq.) and the resulting reaction mixture was stirred at room temperature overnight. Then, it was neutralized with 1 N HCl, lyophilized and used for the next step without further purification. MS m/e 565.5 (M+H)⁺

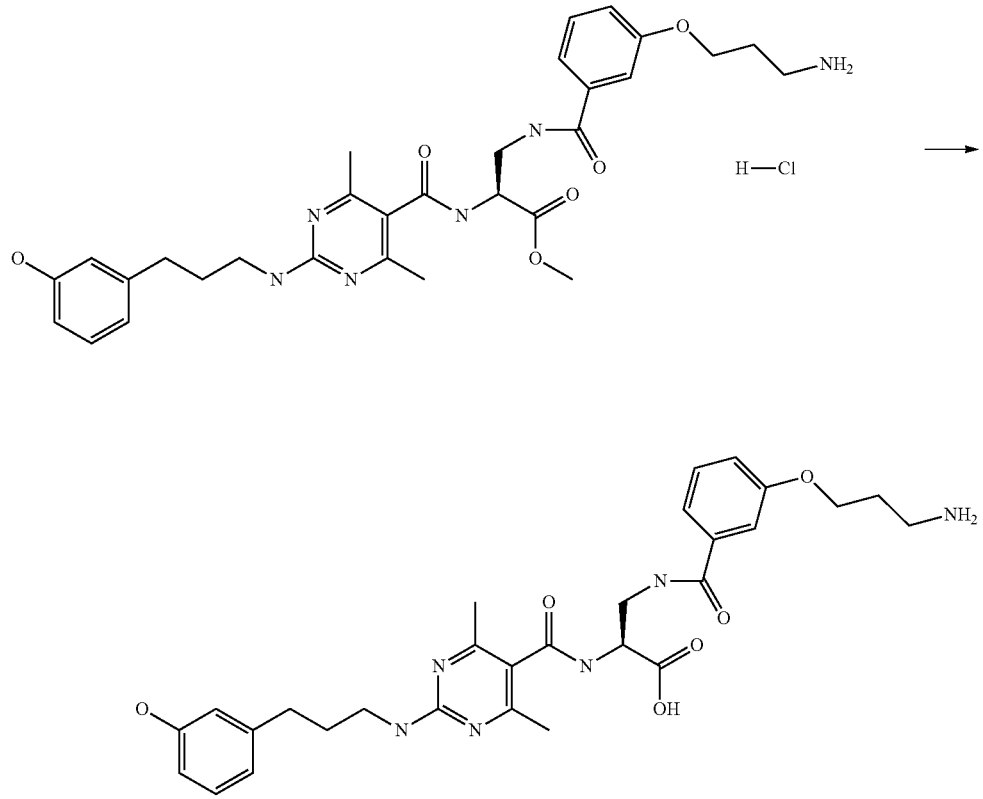 [SMILES: COC(=O)[C@H](CNC(=O)c1cccc(OCCCN)c1)NC(=O)c1c(C)nc(NCCCc2cccc(O)c2)nc1C ; Cl ; Cc1nc(NCCCc2cccc(O)c2)nc(C)c1C(=O)N[C@@H](CNC(=O)c1cccc(OCCCN)c1)C(=O)O]

Preparation of 3-(3-tert-butoxycarbonylamino-propoxy)-5-hydroxy-benzoic acid methyl ester

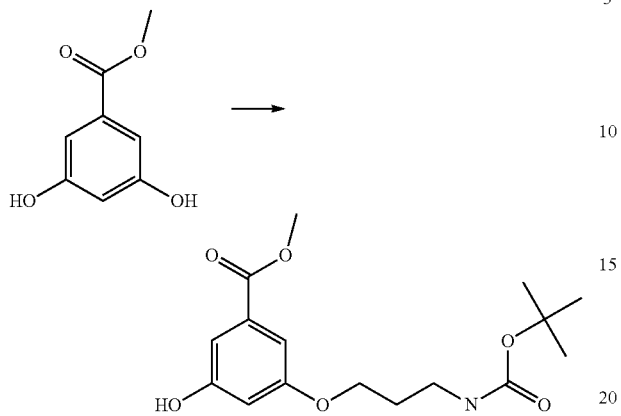

3,5-Dihydroxymethylbenzoate (1.8 g, 10.7 mmol), (3-bromo-propyl)-carbamic acid tert-butyl ester (1.3 g, 5.46 mmol) and potassium carbonate (1.5 g, 10.8 mmol) were combined in a mixture of acetone (50 mL) and DMF (50 mL). The reaction mixture was stirred at 75° C. overnight. The crude reaction mixture was concentrated under reduced pressure, diluted with ethyl acetate and washed with water and brine, followed by drying over anhydrous sodium sulfate. Flash chromatography on silica gel using ethyl acetate and hexanes afforded 462 mg of the title compound. HRMS m/e 348.1417 (M+Na)+

Preparation of 3-(3-tert-butoxycarbonylamino-propoxy)-5-hydroxy-benzoic acid

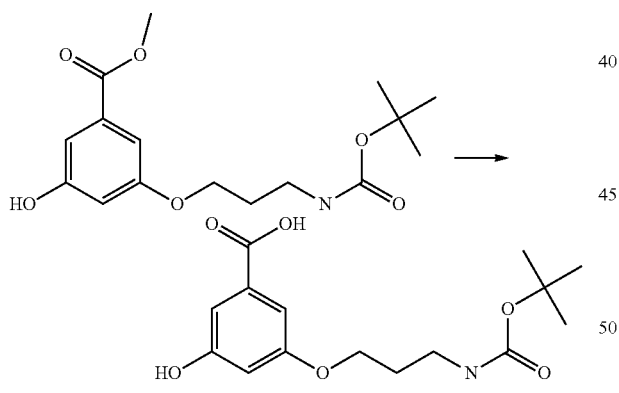

To a solution of 3-(3-tert-butoxycarbonylamino-propoxy)-5-hydroxy-benzoic acid methyl ester (1.2 g 3.69 mmol) in 2M NaOH (9.2 mL, 5 eq.) was added water (20 mL) and the resulting reaction mixture was stirred at room temperature overnight. Then the reaction mixture was neutralized with 1 N HCl and immediately extracted with ethyl acetate. The organic phase was washed with brine and dried over anhydrous sodium sulfate. It was then concentrated under reduced pressure to afford 1.0 g of the title compound. MS m/e 211.8 (M+H-Boc)+

Preparation of 3-(3-tert-butoxycarbonylamino-propoxy)-5-hydroxy-benzoic acid 2,5-dioxo-pyrrolidin-1-yl ester

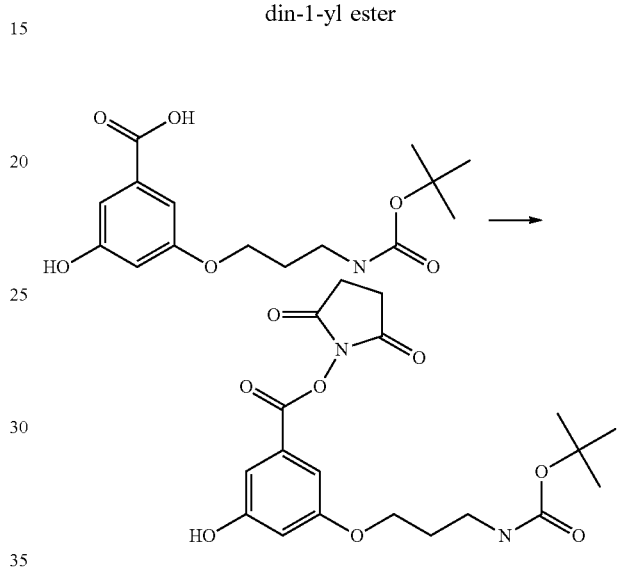

To a cooled solution of 3-(3-tert-butoxycarbonylamino-propoxy)-5-hydroxy-benzoic acid (500 mg, 1.606 mmol) and N-hydroxysuccinimide (185 mg, 1 eq.) in THF (20 mL) was added DCC (332 mg, 1 eq.). The cooling bath was removed after 1 h. The insoluble material was filtered and discarded. The filtrate was concentrated under reduced pressure and the crude material was purified by flash chromatography on silica gel using ethyl acetate and hexanes to afford 602 mg of the title compound. HRMS m/e 431.1426 (M+Na)+

Preparation of (S)-3-[3-(3-tert-butoxycarbonylamino-propoxy)-5-hydroxy-benzoylamino]-2-({2-[3-(3-hydroxy-phenyl)-propylamino]-4,6-dimethyl-pyrimidine-5-carbonyl}-amino)-propionic acid methyl ester

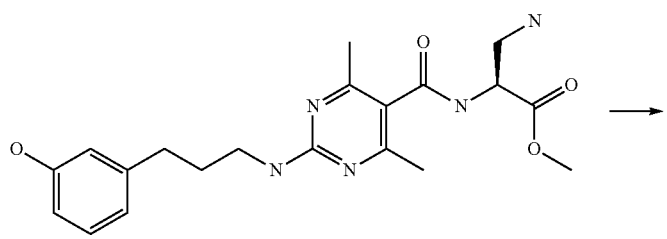

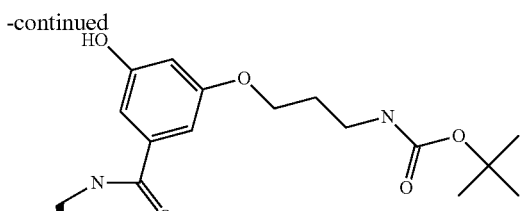
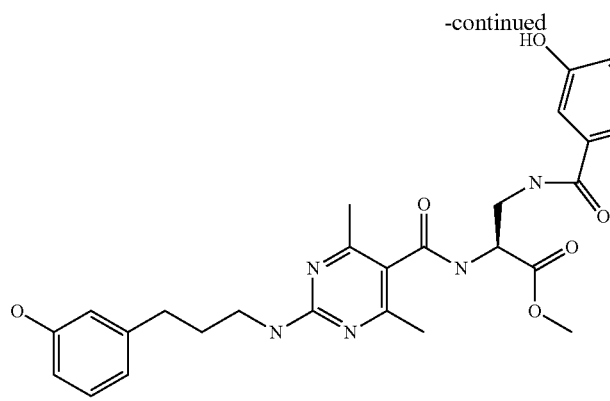

To a solution of (S)-3-amino-2-({2-[3-(3-hydroxy-phenyl)-propylamino]-4,6-dimethyl-pyrimidine-5-carbonyl}-amino)-propionic acid methyl ester hydrochloride (476.4 mg, 0.924 mmol) in DMF (5 mL) were added DIEA (321 μL, 3 eq.) and 3-(3-tert-butoxycarbonylamino-propoxy)-5-hydroxy-benzoic acid 2,5-dioxo-pyrrolidin-1-yl ester (377 mg, 1 eq.). The resulting reaction mixture was stirred at room temperature for 2 h. Then it was diluted with ethyl acetate and washed with water and brine and dried over anhydrous sodium sulfate. The crude material was purified by flash chromatography on silica gel using methanol/methylene chloride to afford 301 mg of the title compound.

HRMS m/e 695.3395 (M+H)+

Preparation of (S)-3-[3-(3-amino-propoxy)-5-hydroxy-benzoylamino]-2-({2-[3-(3-hydroxy-phenyl)-propylamino]-4,6-dimethyl-pyrimidine-5-carbonyl}-amino)-propionic acid methyl ester hydrochloride

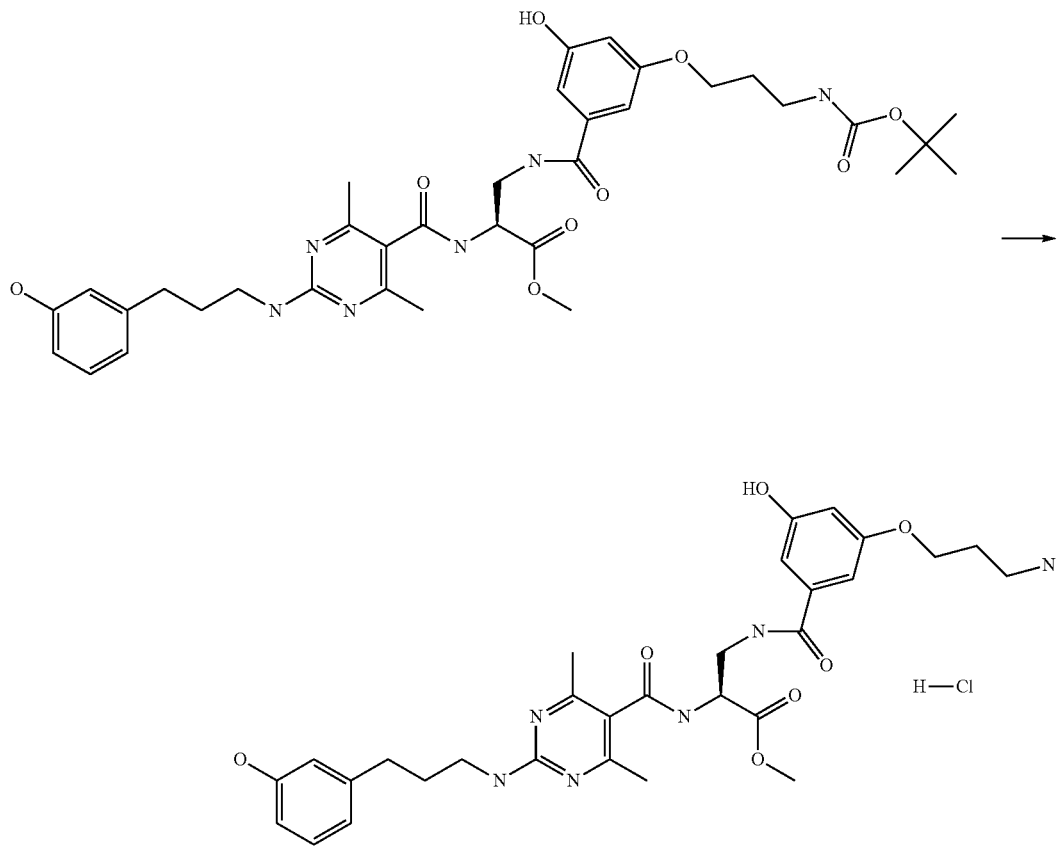

Trimethylsilyl chloride (548 μL) was added to methanol (5 mL) and the resulting solution was stirred at room temperature for 1 min. Then (S)-3-[3-(3-tert-butoxycarbonylamino-propoxy)-5-hydroxy-benzoylamino]-2-({2-[3-(3-hydroxy-phenyl)-propylamino]-4,6-dimethyl-pyrimidine-5-carbonyl}-amino)-propionic acid methyl ester (299.6 mg, 0.431 mmol) was added and stirring at room temperature was continued overnight. Methanol was removed under reduced pressure and the residue was triturated with diethyl ether to afford 272 mg of the title compound. HRMS m/e 595.2875 (M+H)+

Preparation of (S)-3-[3-(3-amino-propoxy)-5-hydroxy-benzoylamino]-2-({2-[3-(3-hydroxy-phenyl)-propylamino]-4,6-dimethyl-pyrimidine-5-carbonyl}-amino)-propionic acid; LFA-1 Ligand 3

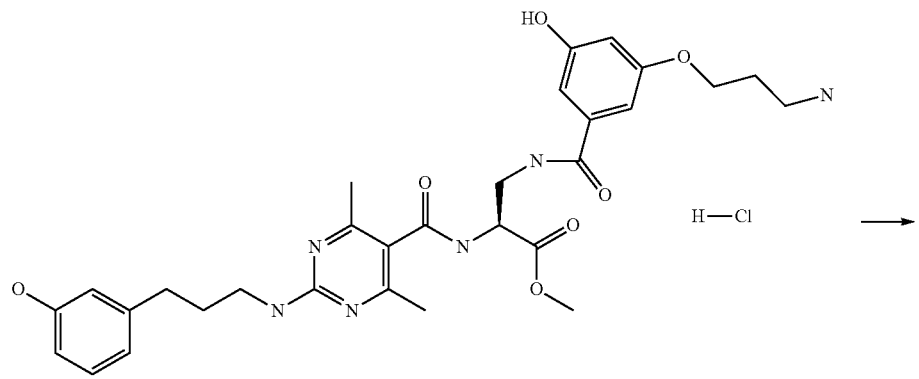

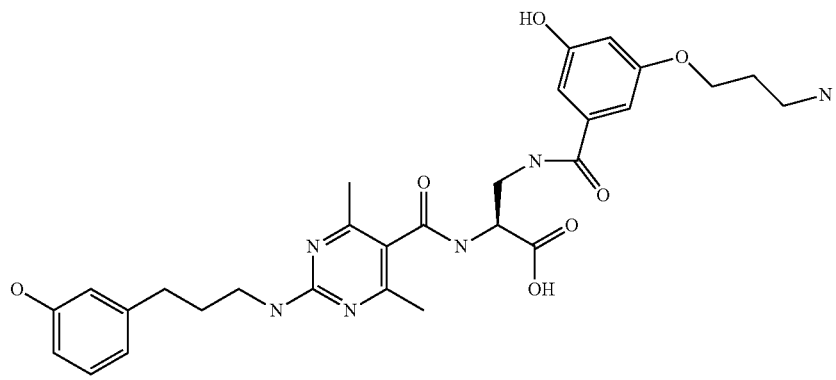

(S)-3-[3-(3-amino-propoxy)-5-hydroxy-benzoylamino]-2-({2-[3-(3-hydroxy-phenyl)-propylamino]-4,6-dimethyl-pyrimidine-5-carbonyl}-amino)-propionic acid methyl ester hydrochloride (100 mg, 0.158 mmol) was dissolved in a mixture of water (1 mL) and methanol (1 mL) and then 2 N NaOH was added (400 µL, 5 eq.). The reaction mixture was stirred at room temperature for 3 h. Then it was neutralized with 1 N HCl, lyophilized and used for the next step without further purification. MS m/e 581.1 (M+H)+

Preparation of (S)-2-tert-butoxycarbonylamino-3-[4-(2,6-dichloro-4-triisopropylsilanyloxy-benzoylamino)-phenyl]-propionic acid methyl ester

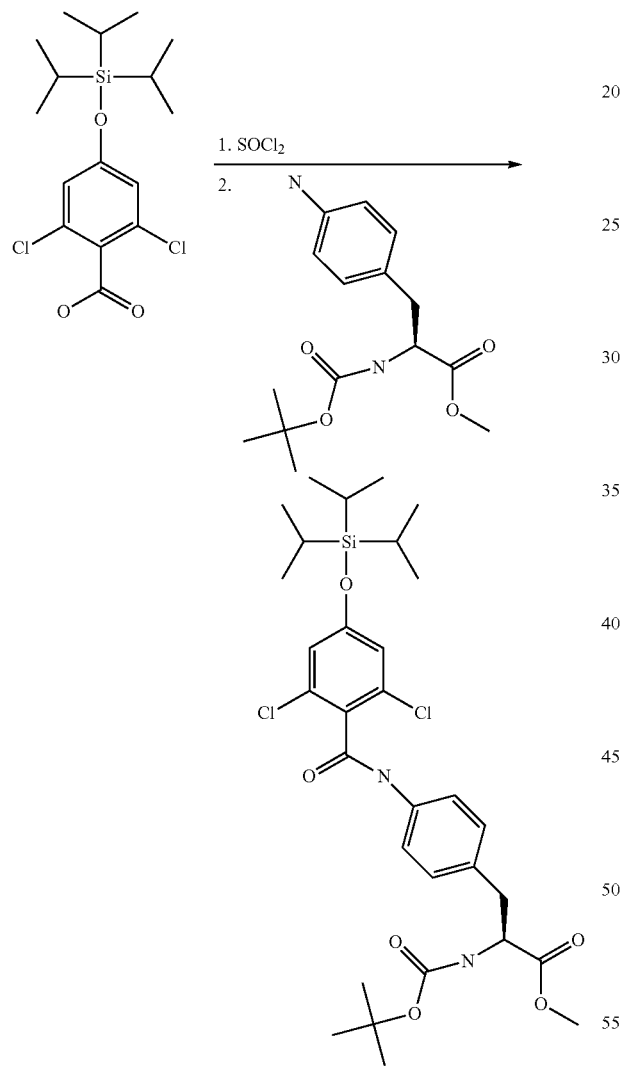

To a solution of 2,6-dichloro-4-triisopropylsilanyloxy-benzoic acid (50 mg, 0.138 mmol) in toluene (2 mL) was added thionyl chloride (50 µL, 0.69 mmol). The resulting solution was refluxed for 2 h. Then thionyl chloride and toluene were removed under reduced pressure. The oily residue was redissolved in methylene chloride (3 mL) and cooled to 0° C. Then DIEA (72 µL, 0.414 mmol) and (S)-3-(4-amino-phenyl)-2-tert-butoxycarbonylamino-propionic acid methyl ester (43 mg, 0.145 mmol) were added and the resulting reaction mixture was stirred at room temperature over the weekend. The crude material was purified by flash chromatography on silica gel using ethyl acetate and hexanes to afford 87 mg of title compound. HRMS m/e 661.2237 (M+Na)+

Preparation of (S)-2-tert-butoxycarbonylamino-3-[4-(2,6-dichloro-4-hydroxy-benzoylamino)-phenyl]-propionic acid methyl ester

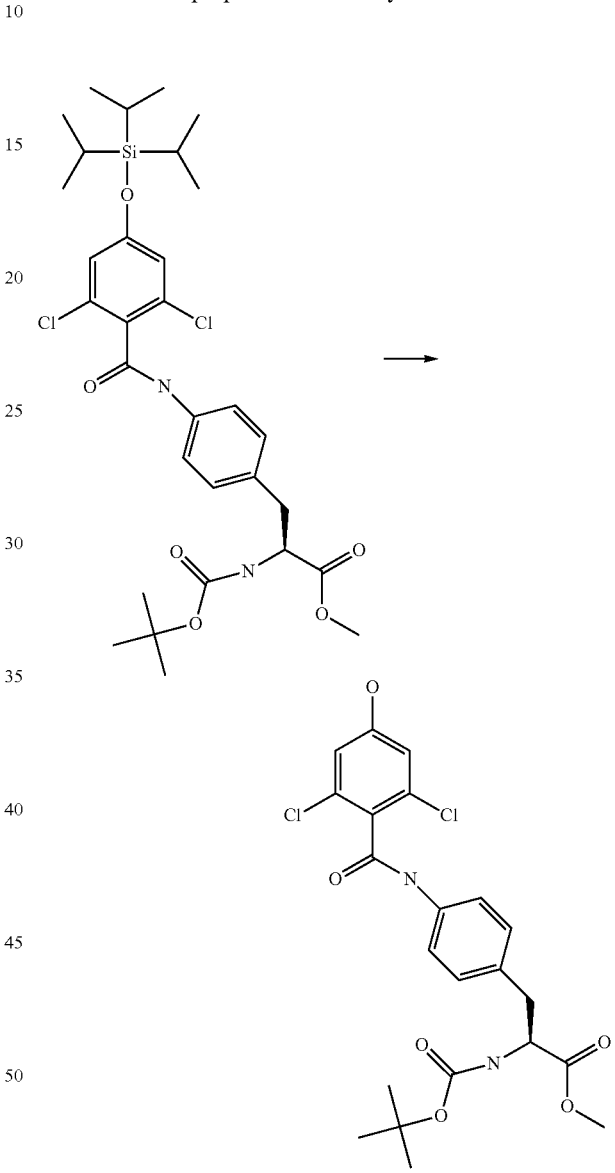

To a solution of (S)-2-tert-butoxycarbonylamino-3-[4-(2,6-dichloro-4-triisopropylsilanyloxy-benzoylamino)-phenyl]-propionic acid methyl ester (84.7 mg, 0.132 mmol) in THF (1 mL) was added TBAF (199 µL of 1 M solution in THF) and the resulting mixture was stirred at room temperature overnight. The solvent was removed under reduced pressure and the residue, after redissolving in ethyl acetate, was washed with water and brine and then dried over anhydrous sodium sulfate. The crude material was purified by flash chromatography on silica gel using ethyl acetate and hexanes to afford 50.3 mg of title compound. HRMS m/e 505.0903 (M+Na)+

Preparation of (S)-2-amino-3-[4-(2,6-dichloro-4-hydroxy-benzoylamino)-phenyl]propionic acid methyl ester hydrochloride

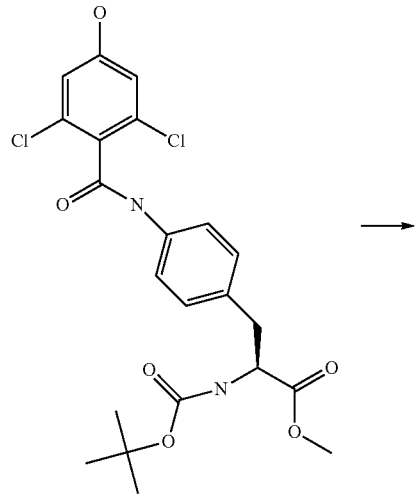

To a solution of TMSCl (1.4 mL, 11.3 mmol) in MeOH (15 mL) was added (S)-2-tert-butoxycarbonylamino-3-[4-(2,6-dichloro-4-hydroxy-benzoylamino)-phenyl]-propionic acid methyl ester (548 mg, 1.13 mmol) and the resulting mixture was stirred at room temperature overnight. The crude mixture was concentrated under reduced pressure and the residue was triturated with diethyl ether to afford 379 mg of the title compound. HRMS m/e 383.0561 (M+H)+

Preparation of N-[3-(tert-butyl-dimethyl-silanyloxy)-benzyl]-2-chloro-terephthalamic acid methyl ester

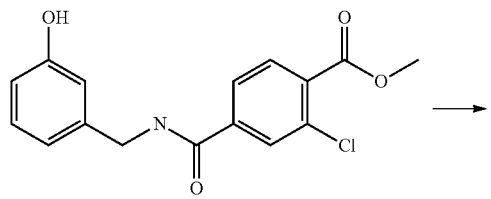

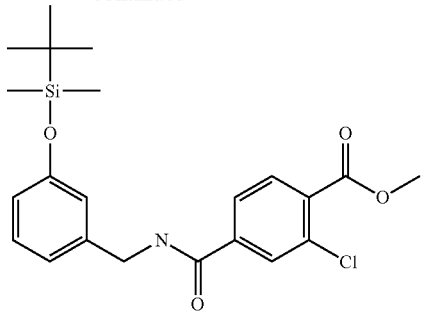

Preparation of 2-chloro-N-(3-hydroxy-benzyl)-terephthalamic acid methyl ester is described in patent WO 01/58853. 2-Chloro-N-(3-hydroxy-benzyl)-terephthalamic acid methyl ester (4.0 g, 12.54 mmol), TBDMSCl (2.3 g, 15.0 mmol) and imidazole (1.9 g, 27.6 mmol) were dissolved in DMF (80 mL) and stirred at room temperature overnight. Then the reaction mixture was diluted with ethyl acetate, washed with water and brine and then dried over anhydrous sodium sulfate. Crude material was purified by flash chromatography on silica gel using ethyl acetate and hexanes to afford 5.0 g of the title compound. MS m/e 433.9 (M+H)+

Preparation of N-[3-(tert-butyl-dimethyl-silanyloxy)-benzyl]-2-chloro-terephthalamic acid

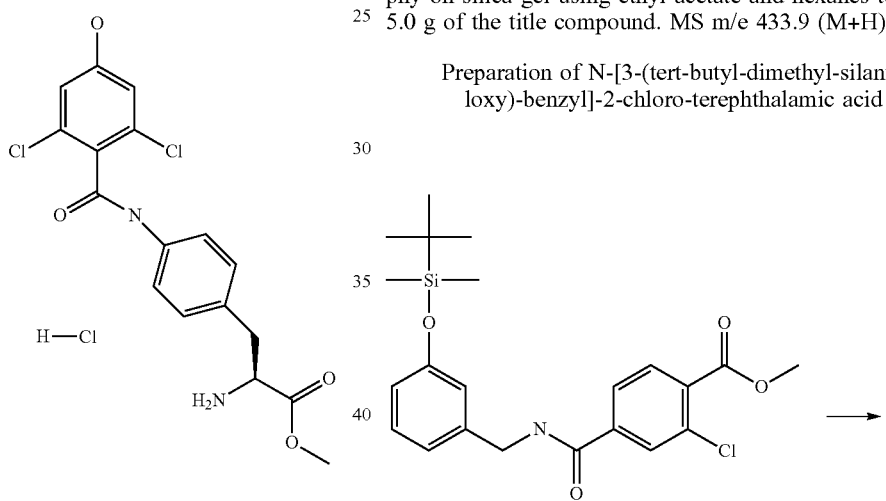

To a solution of N-[3-(tert-butyl-dimethyl-silanyloxy)-benzyl]-2-chloro-terephthalamic acid methyl ester (4.9 g, 11.29 mmol) in 1,2-dichloroethane (80 mL) was added trimethyltin hydroxide (20.4 g, 112.9 mmol) and the resulting reaction mixture was stirred at 80° C. for 8 h. The solvent was removed under reduced pressure and the residue was dissolved in ethyl acetate. It was then washed with an aqueous solution of KHSO4, dried over anhydrous sodium sulfate and filtered through the silica pad. The filtrate was concentrated under reduced pressure to afford 4.0 g of the title compound. HRMS m/e 420.1393 (M+H)+

Preparation of (S)-2-{4-[3-(tert-butyl-dimethyl-silanyloxy)-benzylcarbamoyl]-2-chloro-benzoylamino}-3-[4-(2,6-dichloro-4-hydroxy-benzoylamino)-phenyl]-propionic acid methyl ester

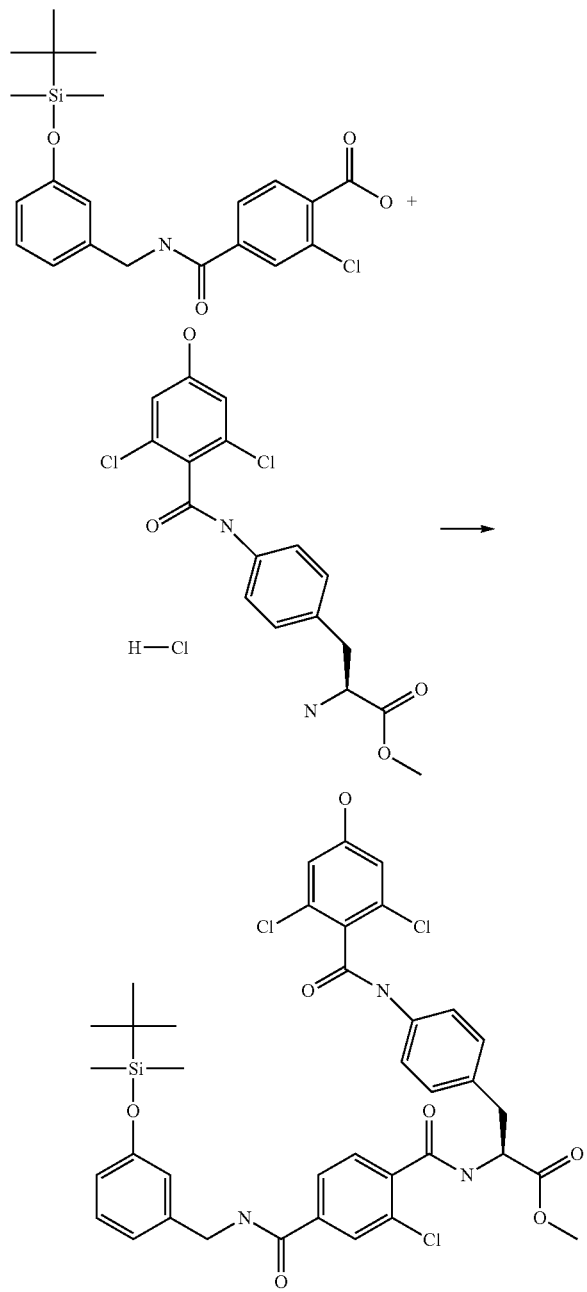

To a solution of N-[3-(tert-butyl-dimethyl-silanyloxy)-benzyl]-2-chloro-terephthalamic acid (103 mg, 0.246 mmol) in DMF (2 mL) were added HBTU (103 mg, 0.271 mmol), DIEA (128 µL, 0.738 mmol) and (S)-2-amino-3-[4-(2,6-dichloro-4-hydroxy-benzoylamino)-phenyl]propionic acid methyl ester hydrochloride salt (103 mg, 0.246 mmol). The resulting reaction mixture was stirred at room temperature over the weekend. Then it was diluted with ethyl acetate, washed with water and brine. Crude material was purified by flash chromatography on silica gel using methanol/methylene chloride to afford 100 mg of the title compound. HRMS m/e 784.1776 (M+H)⁺

Preparation of (S)-3-{4-[4-(3-tert-butoxycarbonylamino-propoxy)-2,6-dichlorobenzoylamino]-phenyl}-2-[2-chloro-4-(3-hydroxy-benzylcarbamoyl)-benzoylamino]-propionic acid methyl ester

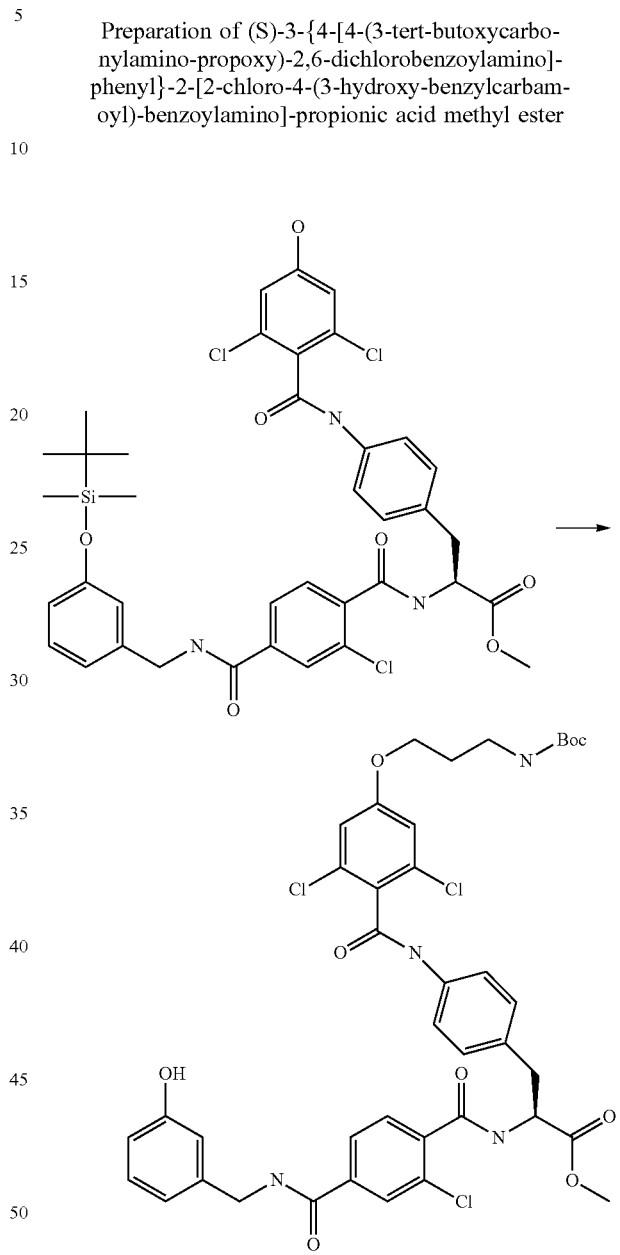

To a solution of (S)-2-{4-[3-(tert-butyl-dimethyl-silanyloxy)-benzylcarbamoyl]-2-chloro-benzoylamino]-3-[4-(2,6-dichloro-4-hydroxy-benzoylamino)-phenyl]-propionic acid methyl ester (91.5 mg, 0.116 mmol) in a mixture of acetone (1 mL) and DMF (1 mL) were added potassium carbonate (48 mg, 3 eq.) and (3-bromo-propyl)-carbamic acid tert-butyl ester (33 mg, 1.2 eq.). The resulting reaction mixture was stirred at 75° C. overnight. Then it was diluted with ethyl acetate and washed with water and brine and dried over anhydrous sodium sulfate. The crude material was purified by flash chromatography on silica gel using methanol/methylene chloride to afford 76.5 mg of the title compound. HRMS m/e 827.2016 (M+H)⁺

77

Preparation of (S)-3-{4-[4-(3-amino-propoxy)-2,6-dichloro-benzoylamino]-phenyl}-[2-chloro-4-(3-hydroxy-benzylcarbamoyl)-benzoylamino]-propionic acid methyl ester hydrochloride

78

Preparation of (S)-3-{4-[4-(3-Amino-propoxy)-2,6-dichloro-benzoylamino]-phenyl}-2-[2-chloro-4-(3-hydroxy-benzylcarbamoyl)-benzoylamino]-propionic acid; LFA-1 Ligand 4

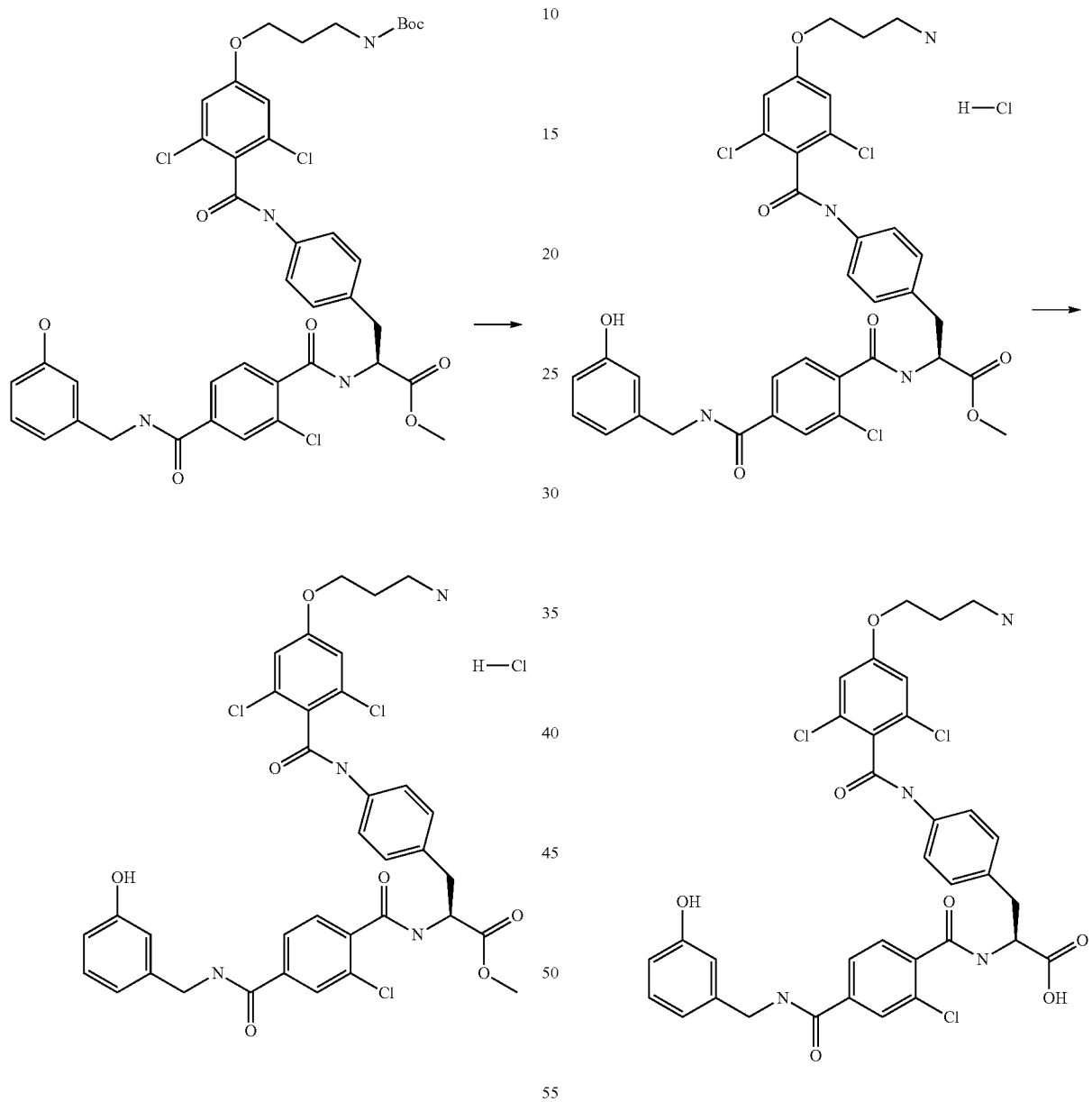

Trimethylsilyl chloride (100 μL, 10 eq.) was added to methanol (2 mL). After 5 min the resulting solution was added to (S)-3-{4-[4-(3-tert-butoxycarbonylamino-propoxy)-2,6-dichlorobenzoylamino]-phenyl}-2-[2-chloro-4-(3-hydroxy-benzylcarbamoyl)-benzoylamino]-propionic acid methyl ester (65.6 mg, 0.079 mmol) and stirred at temperature overnight. The crude reaction mixture was concentrated and triturated with diethyl ether to afford 60.4 mg of the title compound. HRMS m/e 727.1492 (M+H)+

To a solution of (S)-3-{4-[4-(3-amino-propoxy)-2,6-dichloro-benzoylamino]-phenyl}-[2-chloro-4-(3-hydroxy-benzylcarbamoyl)-benzoylamino]-propionic acid methyl ester hydrochloride (55 mg, 0.072 mmol) in methanol (1 mL) was added an aqueous solution of 2M NaOH (178 μL, 5 eq.). The resulting reaction mixture was stirred at room temperature overnight. Then it was neutralized with 1N HCl, lyophilized and used for the next step without further purification. MS m/e 713.0 (M+H)+

Example 1

Preparation of LFA-1 Ligand Reagent 1

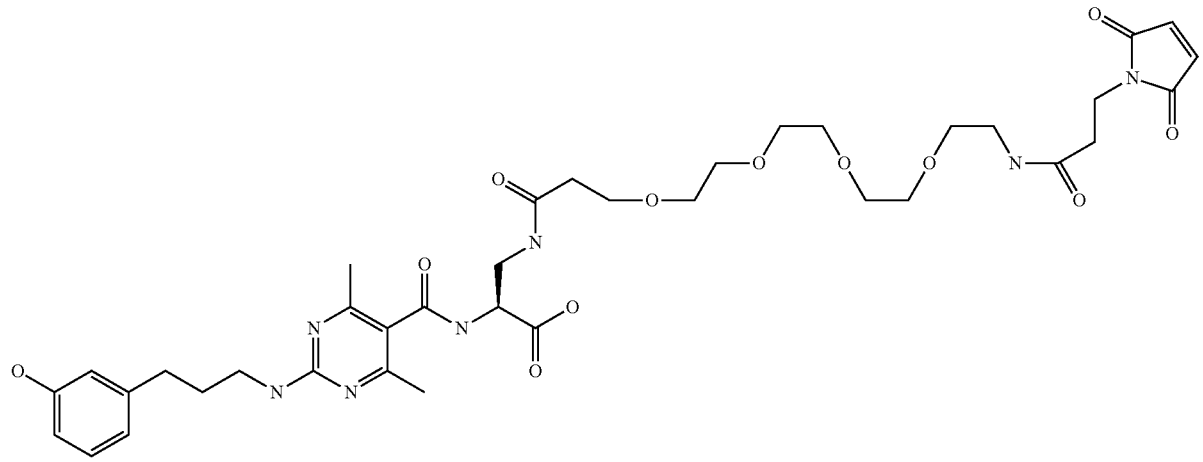 [SMILES: Cc1nc(NCCCc2cccc(O)c2)nc(C)c1C(=O)N[C@@H](CNC(=O)CCOCCOCCOCCOCCNC(=O)CCN1C(=O)C=CC1=O)C(=O)O]

A solution of (S)-3-amino-2-({2-[3-(3-hydroxy-phenyl)-propylamino]-4,6-dimethyl-pyrimidine-5-carbonyl}-amino)-propionic acid hydrochloride (0.114 mmol) in acetonitrile (1 mL) and a solution of succinimidyl-[(N-maleimidopropionamido)-tetraethyleneglycol] ester (58 mg, 0.114 mmol) in 1 mL of DMSO and diisopropylethylamine (40 µL, 0.228 mmol). Both solutions were combined and stirred at room temperature for 30 min. The crude reaction mixture was concentrated under reduced pressure and purified by SFC to afford 51 mg of the title product. HRMS m/e 786.3665 (M+H)$^+$

Example 2

Preparation of LFA-1 Ligand Reagent 2

The title compound was prepared in a similar manner with (S)-3-amino-2-({2-[3-(3-hydroxy-phenyl)-propylamino]-4,6-dimethyl-pyrimidine-5-carbonyl}-amino)-propionic acid hydrochloride and succinimidyl-[(N-maleimidopropionamido)-octaethyleneglycol]ester as shown in Example 1. HRMS m/e 984.4530 (M+Na)$^+$

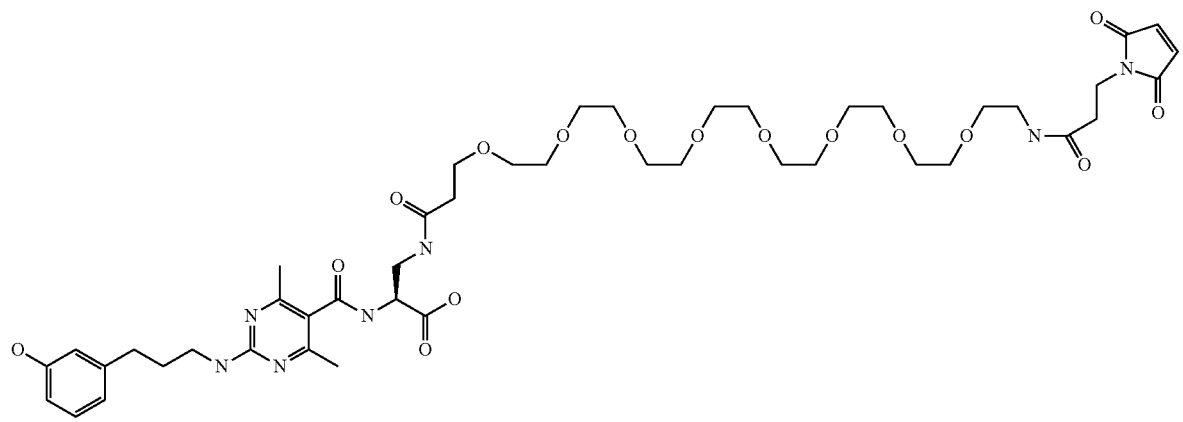 [SMILES: Cc1nc(NCCCc2cccc(O)c2)nc(C)c1C(=O)N[C@@H](CNC(=O)CCOCCOCCOCCOCCOCCOCCOCCOCCNC(=O)CCN1C(=O)C=CC1=O)C(=O)O]

Example 3
Preparation of LFA-1 Ligand Reagent 3
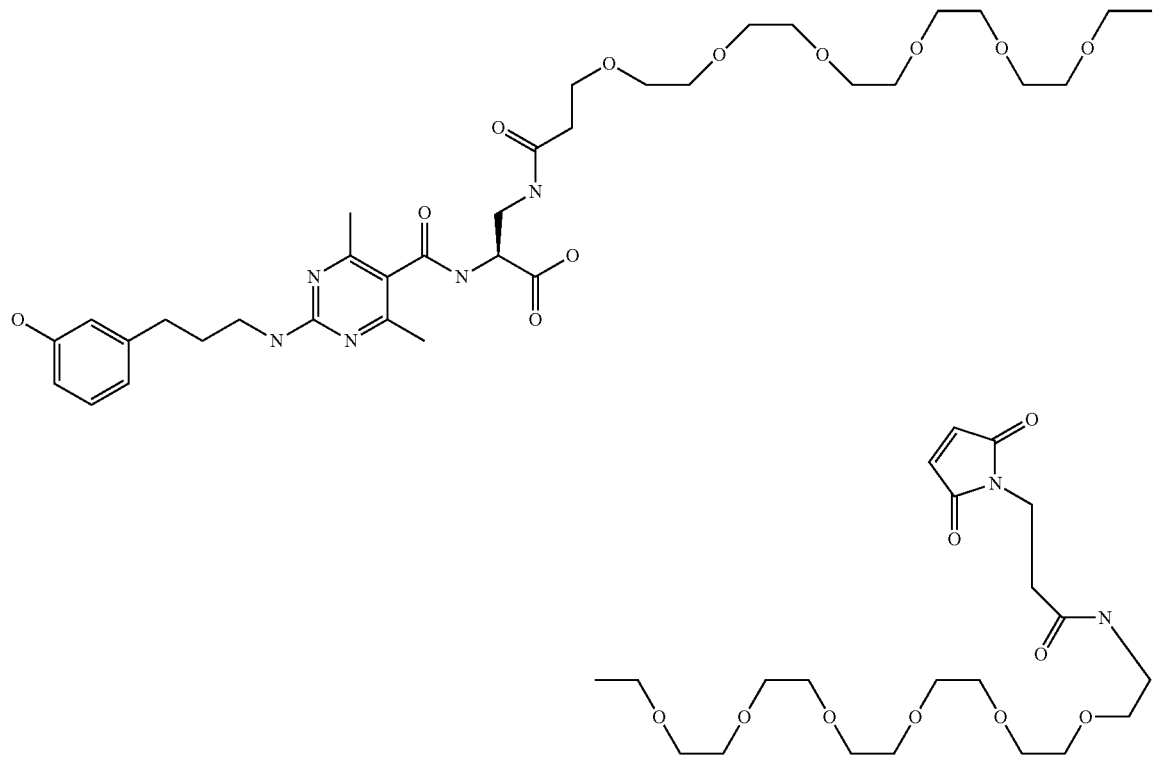
The title compound was prepared in a similar manner with (S)-3-amino-2-({2-[3-(3-hydroxy-phenyl)-propylamino]-4,6-dimethyl-pyrimidine-5-carbonyl}-amino)-propionic acid hydrochloride and succinimidyl-[(N-maleimidopropionamido)-dodecaethyleneglycol]ester as shown in Example 1.
HRMS m/e 1138.5761 (M+H)$^+$
Example 4
Preparation of LFA-1 Ligand Reagent 4
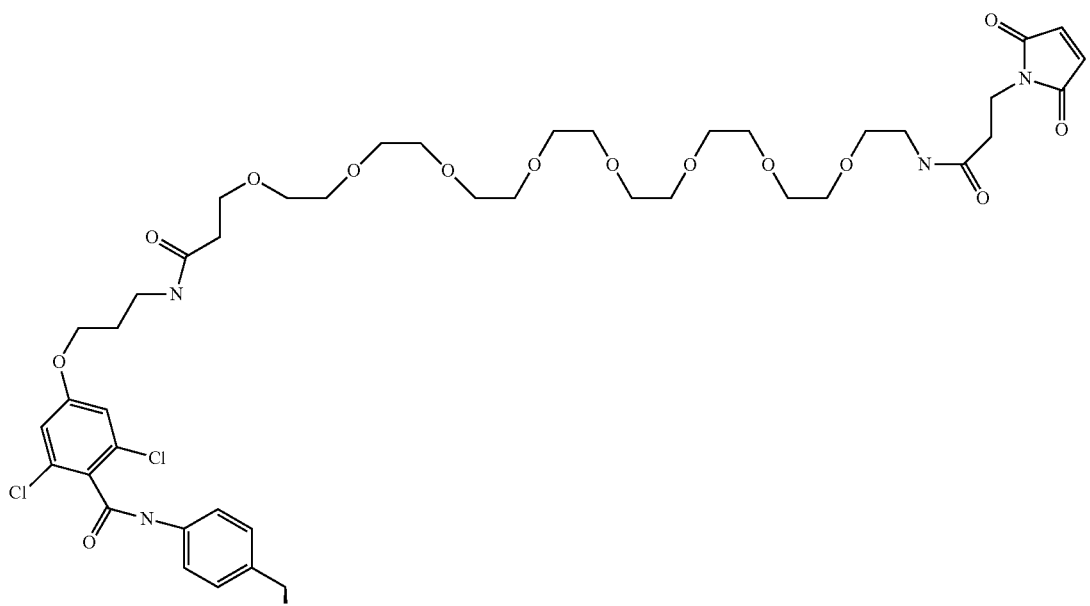

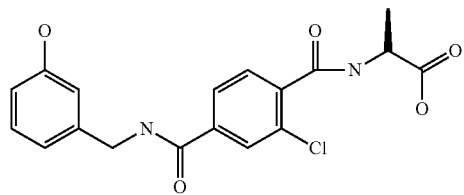

To a solution of (S)-3-{4-[4-(3-amino-propoxy)-2,6-dichloro-benzoylamino]-phenyl}-2-[2-chloro-4-(3-hydroxy-benzylcarbamoyl)-benzoylamino]-propionic acid (0.196 mmol) in DMSO (2 mL) were added DIEA (102 μL, 3 eq.) and succinimidyl-[(N-maleimidopropionamido)-octaethyleneglycol]ester (135 mg, 1 eq.). The resulting mixture was stirred at room temperature for 1 h. Crude material was purified by HPLC to afford 105 mg of the title compound.
HRMS m/e 1287.4077 (M+H)⁺

Example 5

Preparation of LFA-1 Ligand Reagent 5

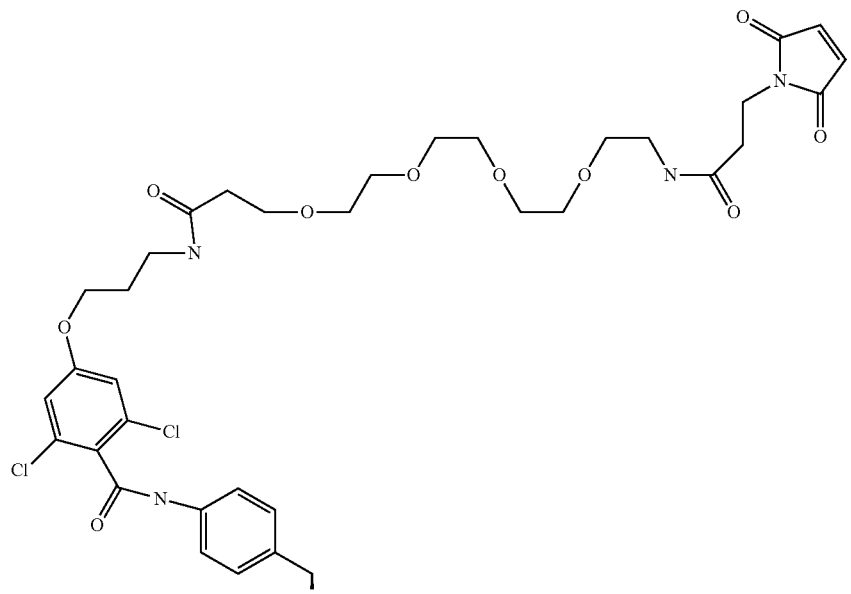

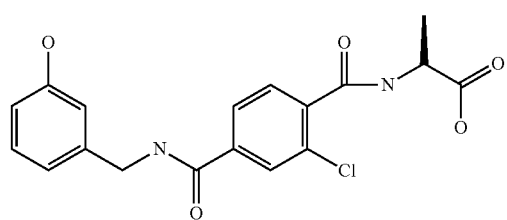

The title compound was prepared in a similar manner with (S)-3-{4-[4-(3-amino-propoxy)-2,6-dichloro-benzoylamino]-phenyl}-2-[2-chloro-4-(3-hydroxy-benzylcarbamoyl)-benzoylamino]-propionic acid and succinimidyl-[(N-maleimidopropionamido)-tetraethyleneglycol]ester as shown in Example 4.
HRMS m/e 1111.3021 (M+H)$^+$
Example 6
Preparation of LFA-1 Ligand Reagent 6
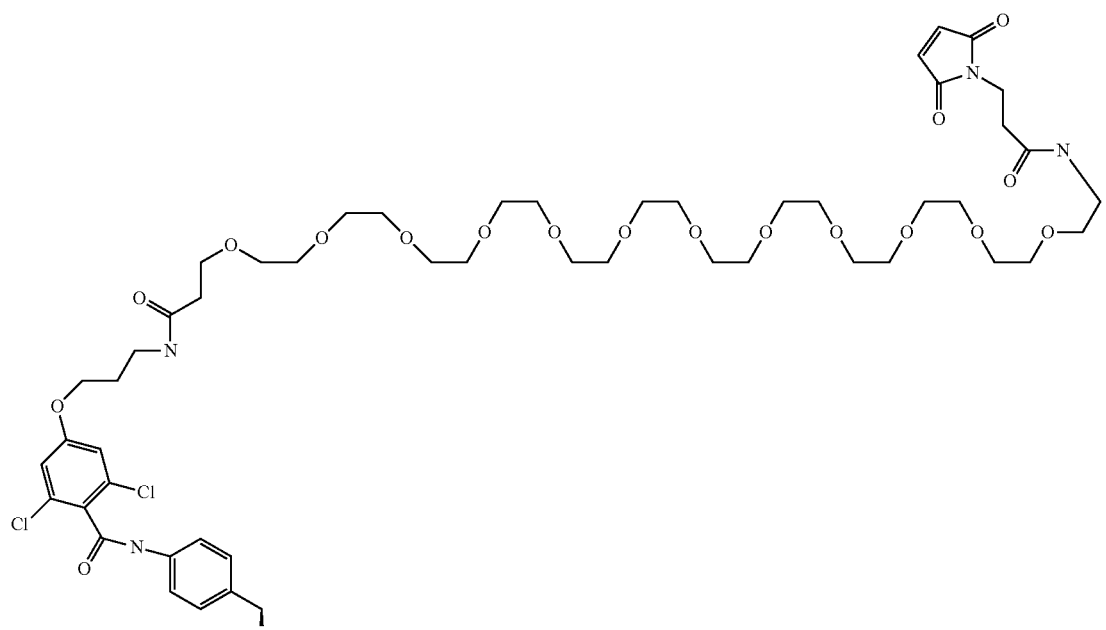
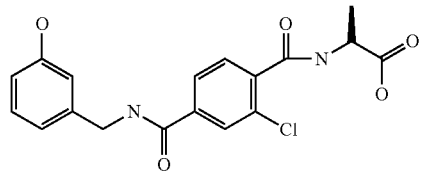

The title compound was prepared in a similar manner with of (S)-3-{4-[4-(3-amino-propoxy)-2,6-dichloro-benzoylamino]-phenyl}-2-[2-chloro-4-(3-hydroxy-benzylcarbamoyl)-benzoylamino]-propionic acid and succinimidyl-[(N-maleimidopropionamido)-dodecaethyleneglycol]ester as shown in Example 4.
HRMS m/e 732.2595 $(M+2H)^{2+}$
Example 7
Preparation of LFA-1 Ligand Reagent 7
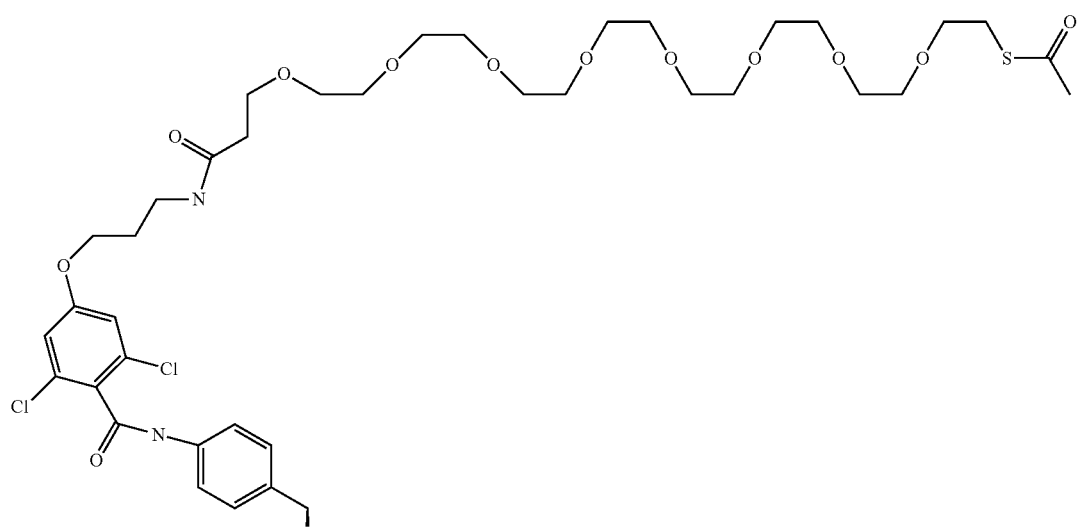
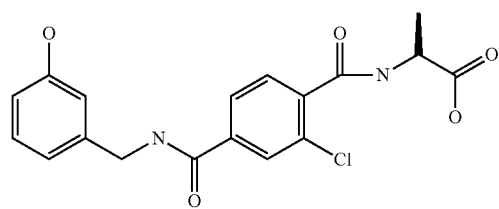

To a solution of (S)-3-{4-[4-(3-amino-propoxy)-2,6-dichloro-benzoylamino]-phenyl}-2-[2-chloro-4-(3-hydroxy-benzylcarbamoyl)-benzoylamino]-propionic acid (0.131 mmol) in DMSO (2 mL) were added DIEA (46 μL, 2 eq.) and 3-[2-(2-{2-[2-(2-{2-[2-(2-acetylsulfanyl-ethoxy)-ethoxy]-ethoxy}-ethoxy)-ethoxy]-ethoxy}-ethoxy)-ethoxy]-propionic acid 2,5-dioxo-pyrrolidin-1-yl ester (78 mg, 1 eq.). The resulting mixture was stirred at room temperature for 1 h. Crude material was purified by HPLC to afford 114 mg of the title compound.

HRMS m/e 1195.3511 (M+H)+

Example 8

Preparation of LFA-1 Ligand Reagent 8

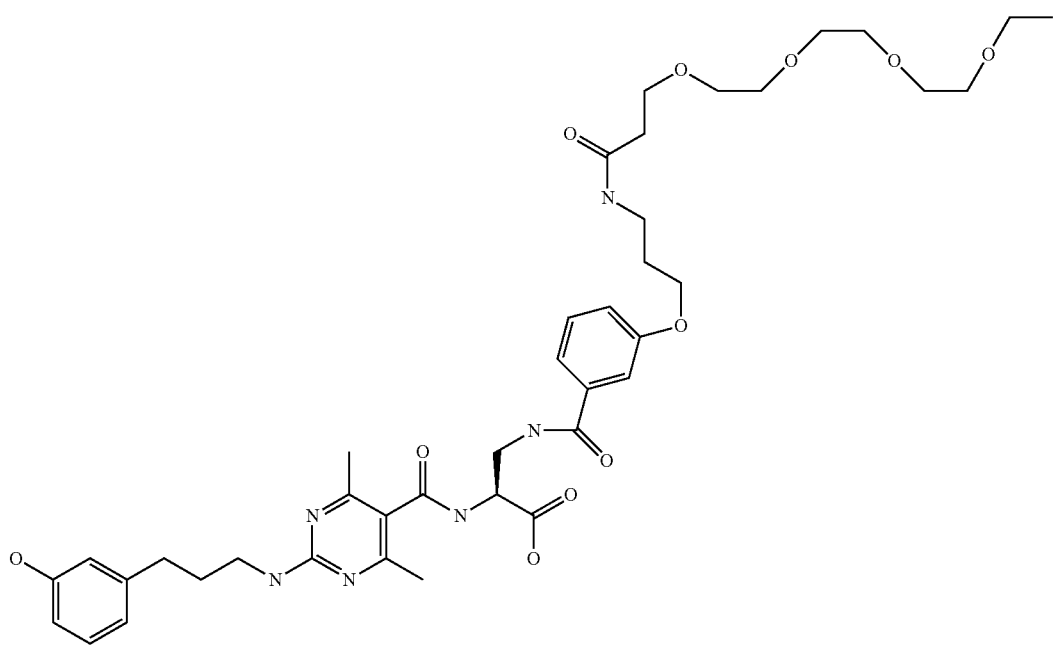

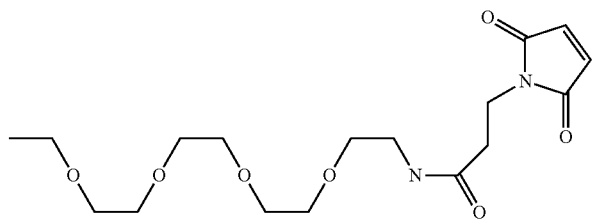

The title compound was prepared in a similar manner with (S)-3-[3-(3-amino-propoxy)-benzoylamino]-2-({2-[3-(3-hydroxy-phenyl)-propylamino]-4,6-dimethyl-pyrimidine-5-carbonyl}-amino)-propionic acid and succinimidyl-[(N-maleimidopropionamido)-octaethyleneglycol]ester as shown in Example 1.
HRMS m/e 1139.5511 (M+H)+
Example 9
Preparation of LFA-1 Ligand Reagent 9
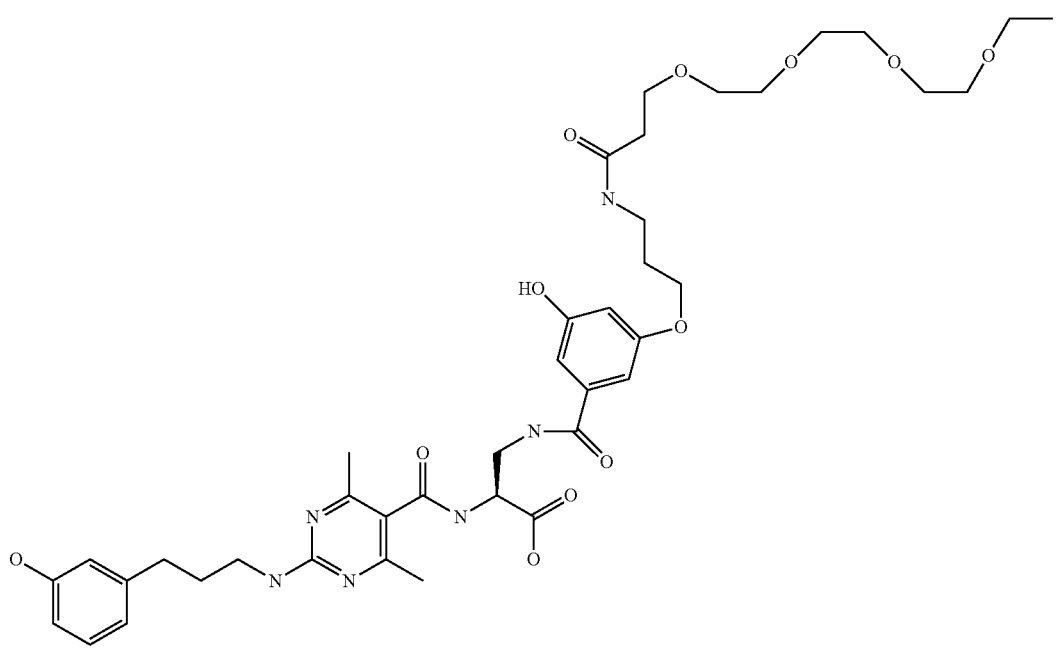
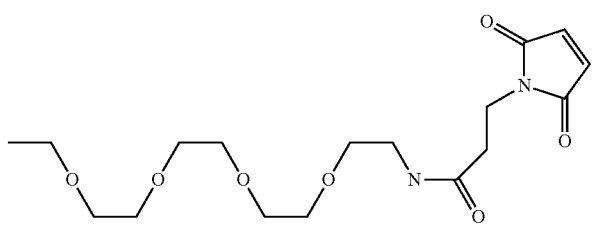

The title compound was prepared in a similar manner with (S)-3-[3-(3-amino-propoxy)-5-hydroxy-benzoylamino]-2-({2-[3-(3-hydroxy-phenyl)-propylamino]-4,6-dimethyl-pyrimidine-5-carbonyl}-amino)-propionic acid and succinimidyl-[(N-maleimidopropionamido)-octaethyleneglycol]ester as shown in Example 1.
HRMS m/e 1155.5448 (M+H)⁺
Example 10
Preparation of LFA-1 Ligand Reagent 10
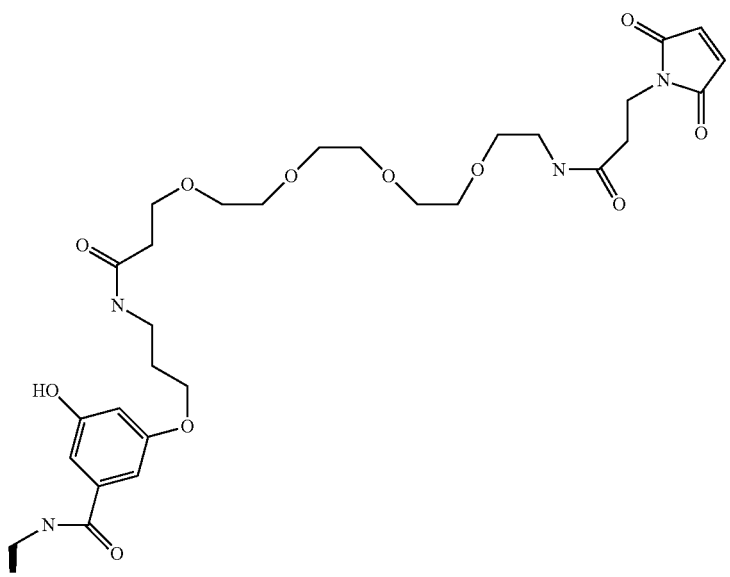
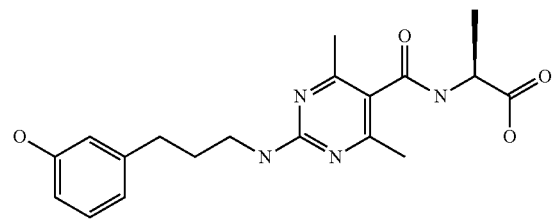

The title compound was prepared in a similar manner with (S)-3-[3-(3-amino-propoxy)-5-hydroxy-benzoylamino]-2-({2-[3-(3-hydroxy-phenyl)-propylamino]-4,6-dimethyl-pyrimidine-5-carbonyl}-amino)-propionic acid and succinimidyl-[(N-maleimidopropionamido)-tetraethyleneglycol] ester as shown in Example 1.

HRMS m/e 979.4403 (M+H)$^+$

Preparation of Fluorescein (FITC) Labeled Targeting Reagents

The targeting reagents may be derivatized with fluorophores that may be useful for studying their binding tracking to cells that express receptors to the targeting small molecules. Such molecules may be made in either or both of two methods. First, it is possible to perform the reaction of the targeted maleimides with 2-[(5-fluoroseinyl)aminocarbonyl]ethylmercaptane. Alternatively, the one-pot reaction of the integrin antagonist small molecule targeting ligands, with 2-[(5-fluoroseinyl)aminocarbonyl]ethylmercaptane and the bi-functional PEG reagent which is shown in Schemes 17 and 18.

Example of Method a)

Preparation of (S)—N-[4-[3-[3-[2-[2-[2-[2-[2-[2-[2-[2-[2-[2-[2-[3-(2,5-dioxo- 2,5-dihydro-pyrrol-1-yl)-propionylamino]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid-FITC To a yellow suspension of (S)—N-[4-[3-[3-[2-[2-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid (37.5 mg, 0.03 mmol) and 2-[(5-fluoroseinyl)aminocarbonyl]ethylmercaptane (FITC reagent) (15.6 mg, 0.036 mml) in methanol (5 mL) was added an excess of DIPEA (38.7 mg, 52 uL, 0.3 mmol) at room temperature under nitrogen atmosphere. The resulting light yellow suspension was stirred for 2 h at which time LCMS analysis indicated the absence of starting material. Then, the excess DIPEA was removed under vacuum and the desired product was isolated by purification using HPLC to obtain 25 mg (50% yield) of (S)—N-[4-[3-[3-[2-[2-[2-[2-[2-[2-[2-[2-[2-[2-[2-[3-(2,5- dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid-FITC derivative as a brown solid.

ES(+)-HRMS m/e calcd. for $C_{80}H_{104}N_{10}O_{28}S$ (M+2H)$^{2+}$ 843.3444, obsd. 843.3437.

LCMS data=M+H, 1687.6

Example of Method b)

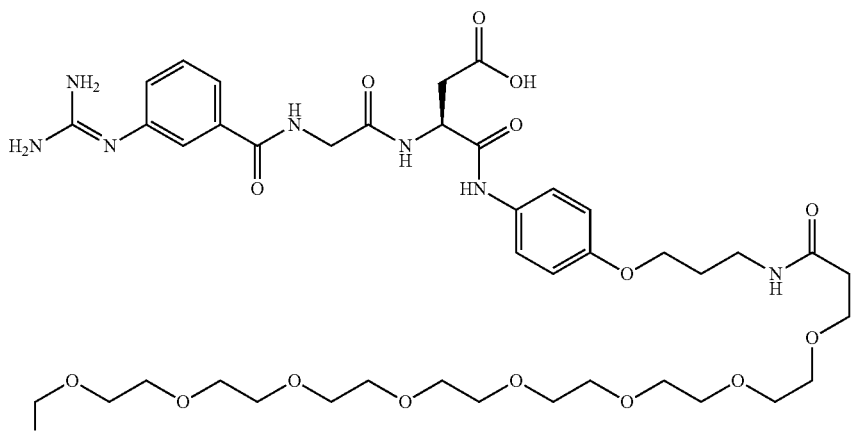

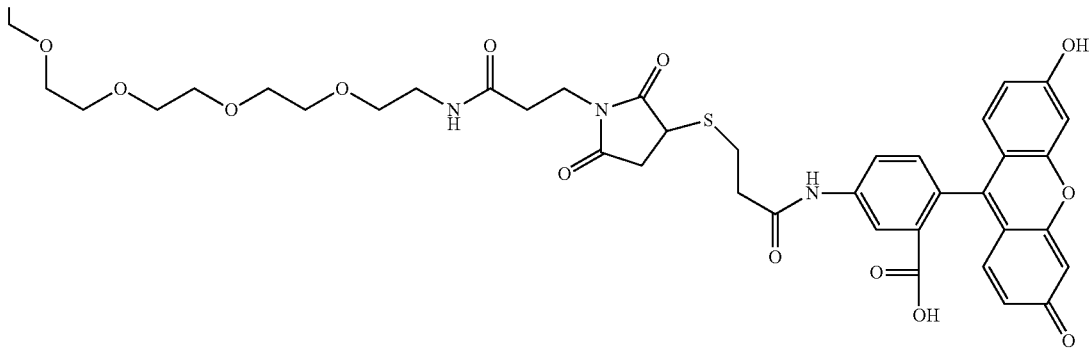

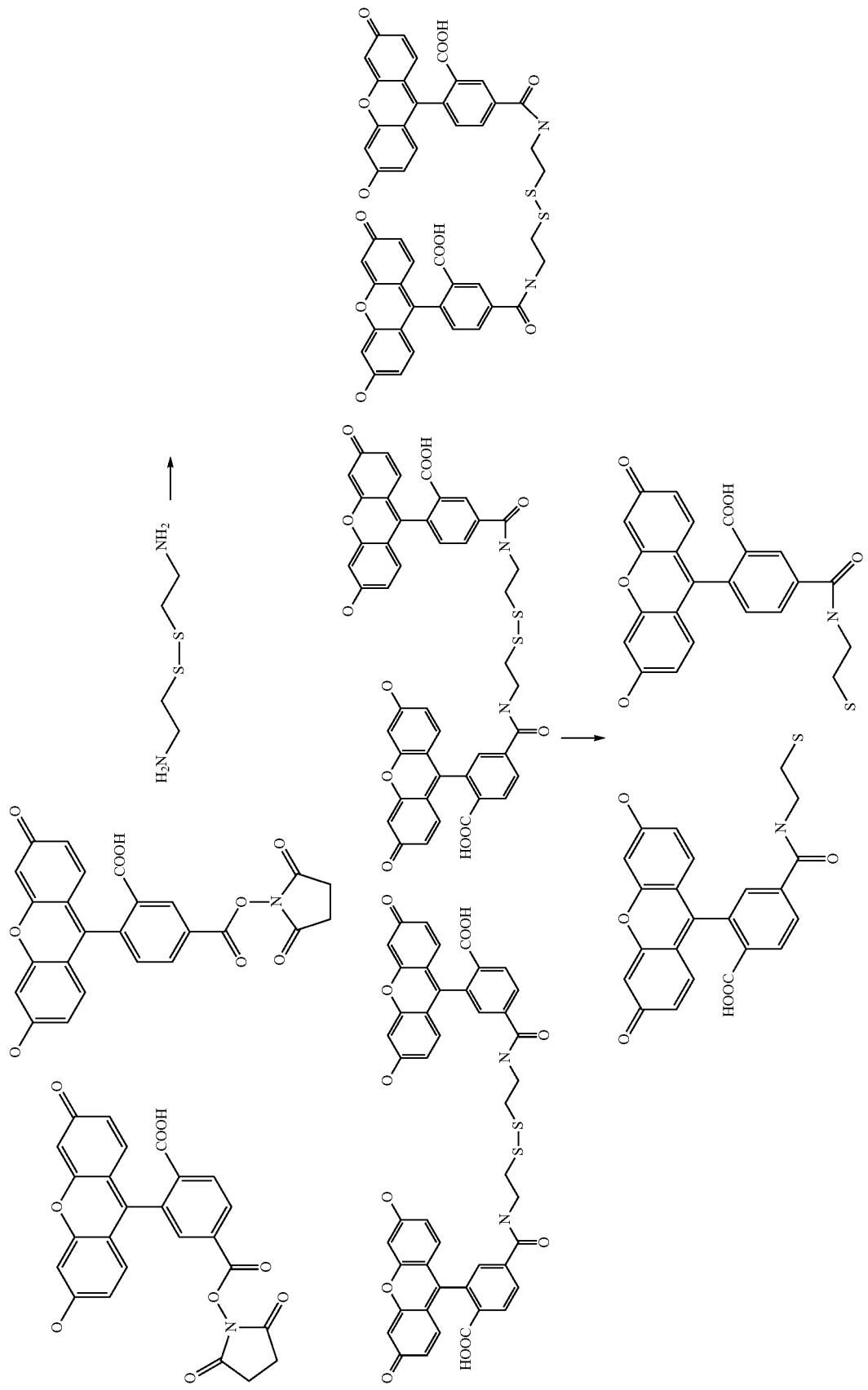

Step 1.

Cystamine dihydrochloride (68 mg, 0.301 mmol) and DIEA (110 μL, 2.1 eq.) were dissolved in DMF (10 mL), followed by addition of NHS-fluorescein, a mixture of 5- and 6-carboxyfluorescein (300 mg, 0.634 mmol) and the resulting reaction mixture was stirred overnight at room temperature. Then it was diluted with ethyl acetate and washed three times with water and one time with brine. The extract was dried over anhydrous sodium sulfate, concentrated under reduced pressure, redissolved in small amount of methanol and ethyl acetate, and then triturated with diethyl ether to obtain 140 mg of fluorescein-cystamine adduct as a bright orange solid.

Step 2.

The fluorescein-cystamine adduct (80 mg, 0.092 mmol) was dissolved in a 3:1 mixture of methanol and water (4 mL) and TCEP hydrochloride (80 mg, 3 eq.) was added. The resulting reaction mixture was stirred at room temperature for 2 h. The product was purified by HPLC to yield 78 mg of the product. LRMS (ESI) 435.0

Preparation of Fluorescein-Labeled Small Molecule-PEG Conjugates

Scheme 18
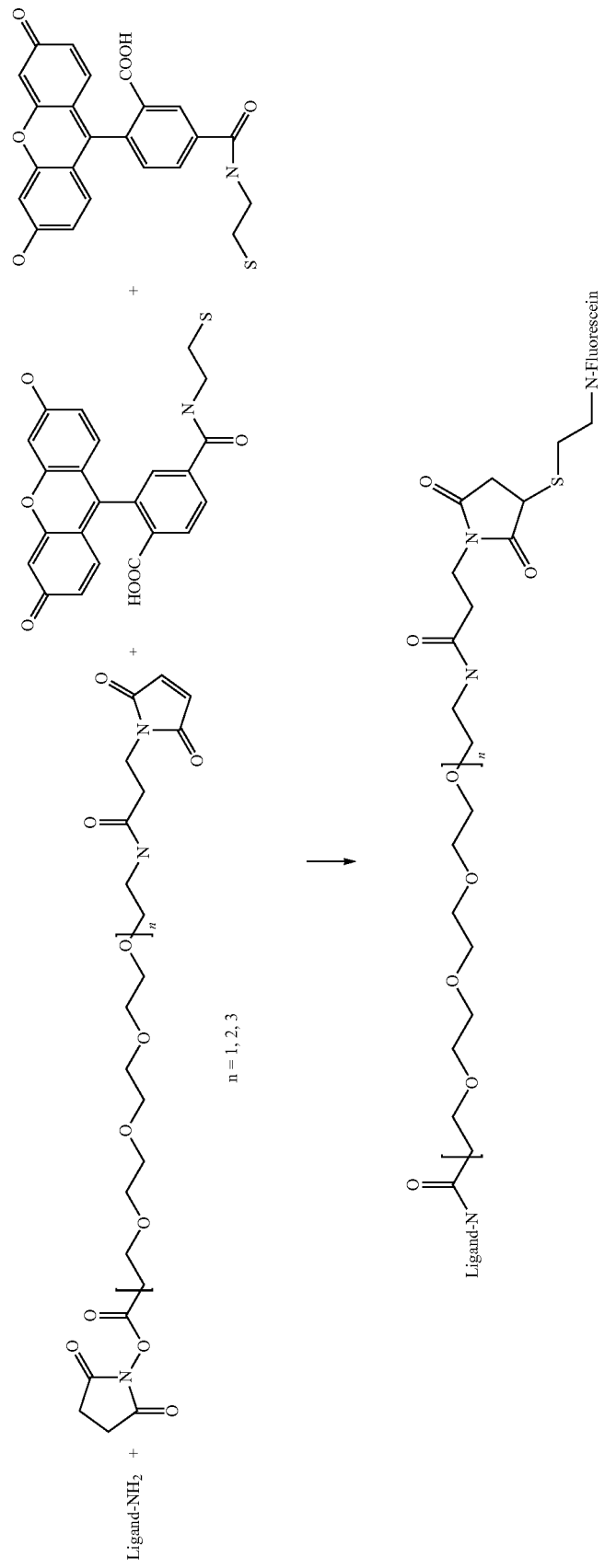

General Procedure:

To a solution of ligand (1 eq.) in DMSO was added DIEA (2 eq.) and SM(PEG)$_{4n}$ (1 eq.). The resulting reaction mixture was stirred at room temperature for 1 h. Next, fluorescein with thiol handle (1 eq.) was added and the reaction mixture was stirred for an additional 10 min. The product was purified by HPLC.

Procedures for Covalent Attachment to Small Molecule Integrin Targeting Ligands to 5'-Thiol-siRNA Oligonucleotides siRNA Preparation.

Oligoribonucleotide Synthesis

Oligoribonucleotides were synthesized according to the phosphoramidite technology on solid phase employing an ABI 394 synthesizer (Applied Biosystems) at the 10 µmol scale. Sequences:

```
Sense strand
                                    (SEQ ID NO. 1)
GGAuGAAGuGGAGAuuAGudTsdT Antisense strand
                                    (SEQ ID NO. 2)
ACuAAUCUCcACUUcAUCCdTsdT
```

The corresponding siRNAs are directed against the house keeping gene AHA1. Syntheses were performed on a solid support made of controlled pore glass (CPG, 520Å, with a loading of 75 µmol/g, obtained from Prime Synthesis, Aston, Pa., USA). Regular RNA phosphoramidites, 2'-O-Methyl-phosphoramidites as well as ancillary reagents were purchased from Proligo (Hamburg, Germany). Specifically, the following amidites were used: (5'-O-dimethoxytrityl-N$^6$-(benzoyl)-2'-O-t-butyldimethylsilyl-adenosine-3'-O-(2-cyanoethyl-N,N-diisopropylamino)phosphoramidite, 5'-O-dimethoxytrityl-N$^4$-(acetyl)-2'-O-t-butyldimethylsilyl-cytidine-3'-O-(2-cyanoethyl-N,N-diisopropylamino) phosphoramidite, (5'-O-dimethoxytrityl-N$^2$-(isobutyryl)-2'-O-t-butyldimethylsilyl-guanosine-3'-O-(2-cyanoethyl-N,N-diisopropylamino)phosphoramidite, and 5'-O-dimethoxytrityl-2'-O-t-butyldimethylsilyl-uridine-3'-O-(2-cyanoethyl-N,N-diisopropylamino)phosphoramidite. 2'-O-Methylphosphoramidites carried the same protecting groups as the regular RNA amidites. All amidites were dissolved in anhydrous acetonitrile (100 mM) and molecular sieves (3Å) were added. To generate the sulfhydryl linker at the 5'-end of the oligomer the 1-O-Dimethoxytrityl-hexyl-disulfide, 1'-[(2-cyanoethyl)-(N,N-diisopropyl)]-phosphoramidite linker from Glen Research (Sterling, Va., USA) was used. Prior to small molecule conjugation the disulfide linker was reduced using Tris-(2-carboxyethyl)phosphine (TCEP, see below). For 5'-end labeling with the Nu547 fluorophore the corresponding phosphoramidite obtained from Thermo Fisher (Milwaukee, Wis.) was employed. 5-Ethyl thiotetrazole (ETT, 500 mM in acetonitrile) was used as activator solution. Coupling times were 6 minutes. In order to introduce phosphorothioate linkages a 100 mM solution of 3-ethoxy-1,2,4-dithiazoline-5-one (EDITH, obtained from Link Technologies, Lanarkshire, Scotland) in anhydrous acetonitrile was employed.

Cleavage and Deprotection of Support Bound Oligomer

After finalization of the solid phase synthesis, the dried solid support was transferred to a 15 mL tube and treated with methylamine in methanol (2M, Aldrich) for 180 min at 45° C. After centrifugation the supernatant was transferred to a new 15 mL tube and the CPG was washed with 1200 µL N-methylpyrolidin-2-one (NMP, Fluka, Buchs, Switzerland). The washing was combined with the methanolic methylamine solution and 450 µL Triethylamine trihydrofluoride (TEA.3HF, Alfa Aesar, Karlsruhe, Germany) was added. This mixture was brought to 65° C. for 150 min. After cooling to room temperature 0.75 mL NMP and 1.5 mL of ethoxytrimethylsilane (Fluka, Buchs, Switzerland) was added. 10 min later, the precipitated oligoribonucleotide was collected by centrifugation, the supernatant was discarded and the solid was reconstituted in 1 mL buffer A (see below).

Purification of Oligoribonucleotides

Crude oligoribonucleotides were purified by strong anion exchange (SAX) HPLC employing a preparative 22×250 mm DNA Pac 100 column (Dionex, Idstein, Germany) on an AKTA Explorer system (GE Healthcare). Buffer A consisted of 10 mM NaClO$_4$, 1 mM EDTA, 10 mM Tris, pH 7.4, 6M Urea and 20% acetonitrile. Buffer B had 500 mM NaClO$_4$ in Buffer A. A flow rate of 4.5 mL/min was employed. UV traces at 260 and 280 nm were recorded. A gradient of 20% B to 45% B within 55 min was employed. Appropriate fractions were pooled and precipitated with 3M NaOAc, pH=5.2 and 70% Ethanol.

Crude Nu547 labeled oligomers were purified by RP HPLC using a XTerra Prep MS C8 10×50 mm column (Waters, Eschborn, Germany) on an AKTA Explorer system (GE Helthcare). Buffer A was 100 mM triethylammonium acetate (Biosolve, Valkenswaard, The Netherlands) and buffer B contained 50% acetonitrile in buffer A. A flow rate of 5 mL/min was employed. UV traces at 260, 280 and 547 nm (in case of Nu547 labeled oligoribonucleotide) were recorded. A gradient of 5% B to 60% B within 58 column volumes (CV) was employed. Appropriate fractions were pooled and precipitated with 3M NaOAc, pH=5.2 and 70% Ethanol.

Finally, the purified oligomer was desalted by size exclusion chromatography on a column containing Sephadex G-25 (GE Healthcare). The concentration of the solution was determined by absorbance measurement at 260 nm in a UV photometer (Beckman Coulter, Krefeld, Germany). Until annealing the individual strands were stored as frozen solutions at −20° C.

Preparation of Small Molecule RNA Conjugates

Small molecules equipped with a maleimide functionality were covalently conjugated to the RNA through a thioether linkage. To enable this chemistry, ~60 mg of the RNA containing the 5'-disulfide linker was reduced in water (5 mL) to the corresponding thiol using 1 mL TCEP (0.5 M in water, obtained from Sigma Aldrich). Once analytical anion exchange HPLC indicated completion of the reaction (~2 h at room temperature) the RNA was precipitated with 30 mL ethanol/3M NaOAc (pH 5.4) 32:1 (v/v) over night at −20° C. The pellet was collected by centrifugation and used for the subsequent small molecule conjugation.

In a typical conjugation reaction 10 mg RNA was dissolved in 2 mL sodium phosphate buffer (0.1 M, pH 7.0). To this solution the small molecule (0.12 mM) in ACN/NMP 1:1 (v/v) was added over a period of 5 minutes. Once RP LC-ESI MS showed consumption of the input RNA the mixture was diluted with water (~10 mL) and ~40 mL ethanol/3M NaOAc (pH 5.4) 32:1 (v/v) was added to precipitate the conjugated RNA over night at −20° C. The pellet was collected by centrifugation, dissolved in water and if necessary purified by anion exchange HPLC pursuing the procedure given above. If the conjugate is sufficiently pure the reaction mixture was filtered through a size exclusion column (Sephadex G-25, GE Healthcare).

Annealing of Oligoribonucleotides to Generate siRNA

Complementary strands were annealed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 95° C. which was cooled to rt within 3 h. Table 3: siRNA sequence information; lower case letters: 2'-OMe nucleotide; s: phosphorothioate linkage; dT: deoxythymidine; (C6SSC6): C-6 disulfide linker; (Cy5): cyanine 5 dye.

The following assay was conducted to assess effect of targeted molecules on the sLFA-1/ICAM-1 ELISA and Mac-1/ICAM-1 interactions.

Plates were coated with either 50 µl/well of 2.0 ug/ml solution of sLFA-1 or Mac-1 receptor in divalent cation buffer (1 mM MnCl$_2$, 0.14M NaCl, 20 mM HEPES pH 7.2) at 4° C. overnight. Two hundred fifty µl of blocking buffer (1% BSA in divalent cation buffer) was added to each well 1 hour at 37° C. Plates were washed 3 times with wash buffer (TBS/0.05% Tween-20/1 mM MnCl$_2$). The compound to be tested was solubilized in DMSO. A series of 1:3 dilutions were performed to achieve a concentration range of 0.45 nM-3 uM. Fifty µl of binding buffer (0.5% BSA in divalent cation buffer)/1% DMSO and 50 µl of the solutions to be tested were added to the appropriate wells and incubated for 1 hour. Fifty µl of 5dICAM-Fc (27 ng/ml) was added to the appropriate wells and 50 µl binding buffer was added to non-specific binding wells and incubated for 2 hours and washed. One hundred µl of 1:4000 HRP-goat anti-huIgG was added to each well and incubated for 1 hour and washed. One hundred µl of 1:1 TMB solution was added to each well and developed for 20 min at room temperature. Color development was stopped by adding 100 µl H$_3$PO$_4$ to each well. Absorbance was measured at 450 nm. These results are shown below in the Table 4 and 5.

The control compounds (142 and 143) were determined to have an IC$_{50}$ of about 37 and 11 nM respectively. The LFA-1 receptors of the cells were presumably bound to or associated with the control compound.

142

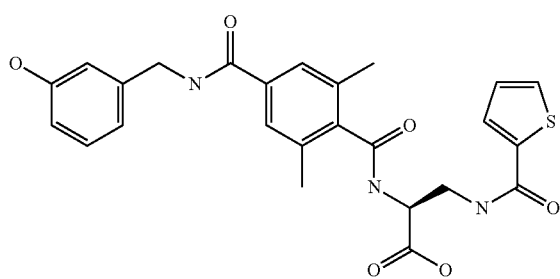

143

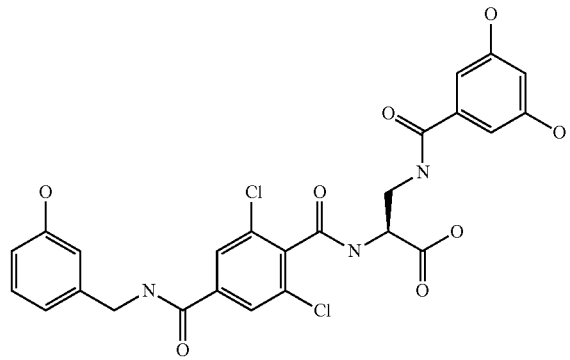

Evidence of Cellular Permeability and Localization of Small Molecule Derivatives for Covalently Linked Integrin Antagonists to FITC Fluorophores and siRNA for Targeted Delivery Procedure AML MV4-11 cells in growth medium (RPMI 1640 with 10% FBS) were incubated with Duplex-27 (500 nM) for 1 hour at 37° C. For determining VLA-4 independent binding, 140 (10 µM) was included in one condition to block VLA-4 dependent binding. After incubation, the cells were then washed twice with D-PBS and fixed in 1% paraformaldehyde for 10 minutes. The uptake of siRNA was analyzed by imaging flow cytometry using ImageStreamx (Aminis Corporation, Seattle). The results are shown in Table A and in FIGS. 1-4.

TABLE A

| Compound (concentration) | Mean Cy3 intensity |
|---|---|
| Nothing | 638 |
| 140 (10 µM) | 663 |
| Duplex-27 (500 nM) | 4007 |
| 140 (10 µM) + Duplex-27 (500 nM) | 2273 |

Assay of 5'-Sense Strand Modified siRNA for Knock-Down of AHA1 mRNA in Cellular Systems Materials and Methods
Reference gene: GAPDH
Cell line: H1299_Nut-Onc
Plating density: 5,000 cells/well
Plating format: 96-well
Time from plating to treatment: 0
Control treatment: mock, untreated, control siRNA
Transfection reagent: DharmaFect1
Transfection Method Reverse TF
TF Reagent volume/well 0.15 mL
siRNA final concentration 50 nM
Assay method: Day 1 manual/Day 2 Washer Reverse transfection: H1299 cells were transfected with indicated siRNA at final concentration of 50 nM using DharmaFect-1 transfection reagent at 0.15 µl/well. Cells were then plated into 96-well plate at 5000 cells/well and incubated at 37° C. for 48 hours.

Figure 5:
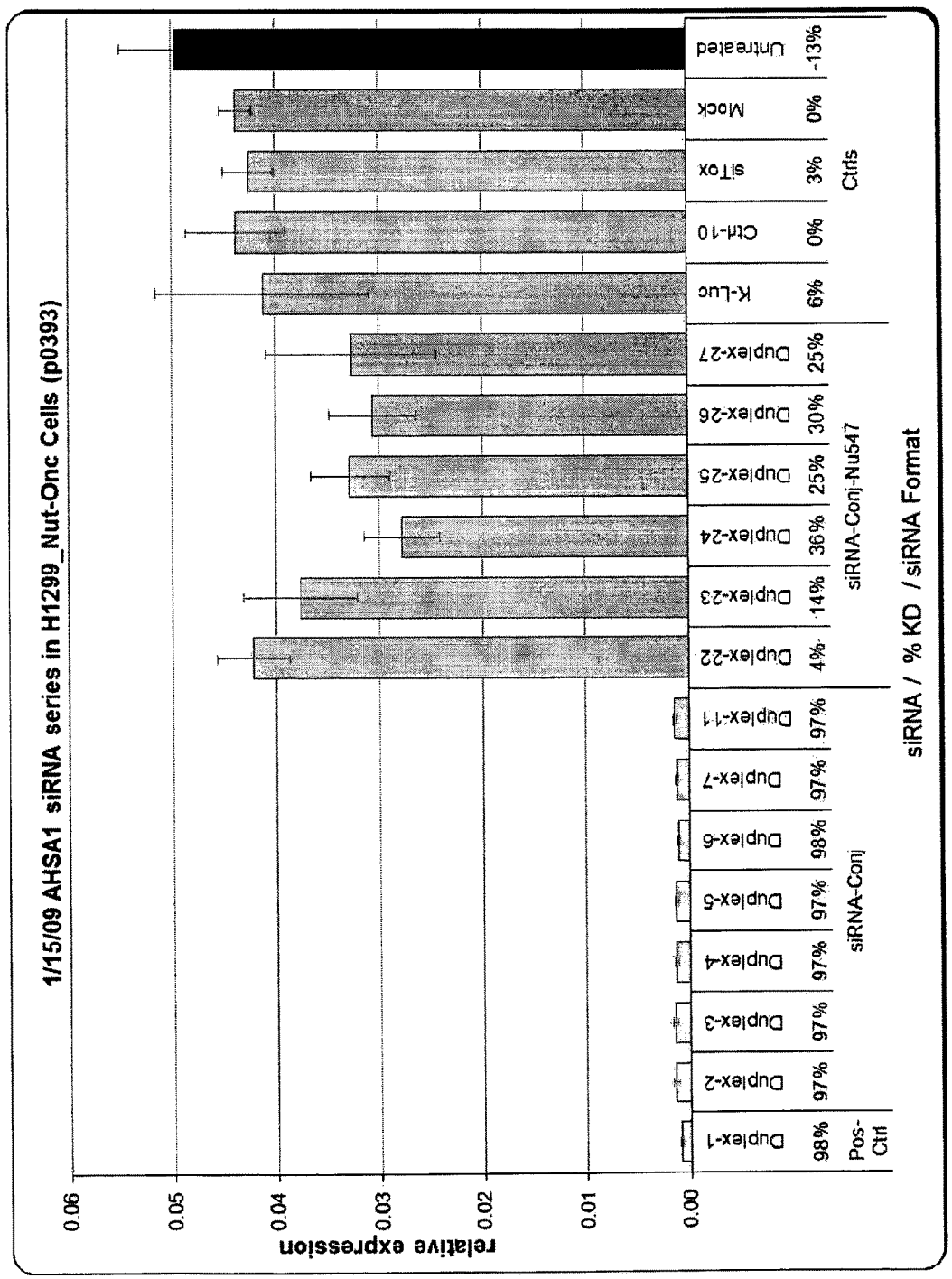
FIG. 5 shows the reduction of AHA1 expression in H1299 cells when treated with siRNA duplexes which have been derivatized on the 5'-sense strand with an integrin targeting small molecule. The y-axis indicates the observed expression level of AHA1. The lower bar indicates a greater degree of knock-down (a higher degree of siRNA transfection); a high bar, a lesser degree of knock-down (i.e., a lesser degree of siRNA transfection). Duplexes in blue have targeting modifications on the 5'-end of the sense strand; those in pink have targeting modifications on the 5'-end of the sense strand as well as Nu547 fluorophore attached to the 5'-end of the antisense strand.
Figure 6:
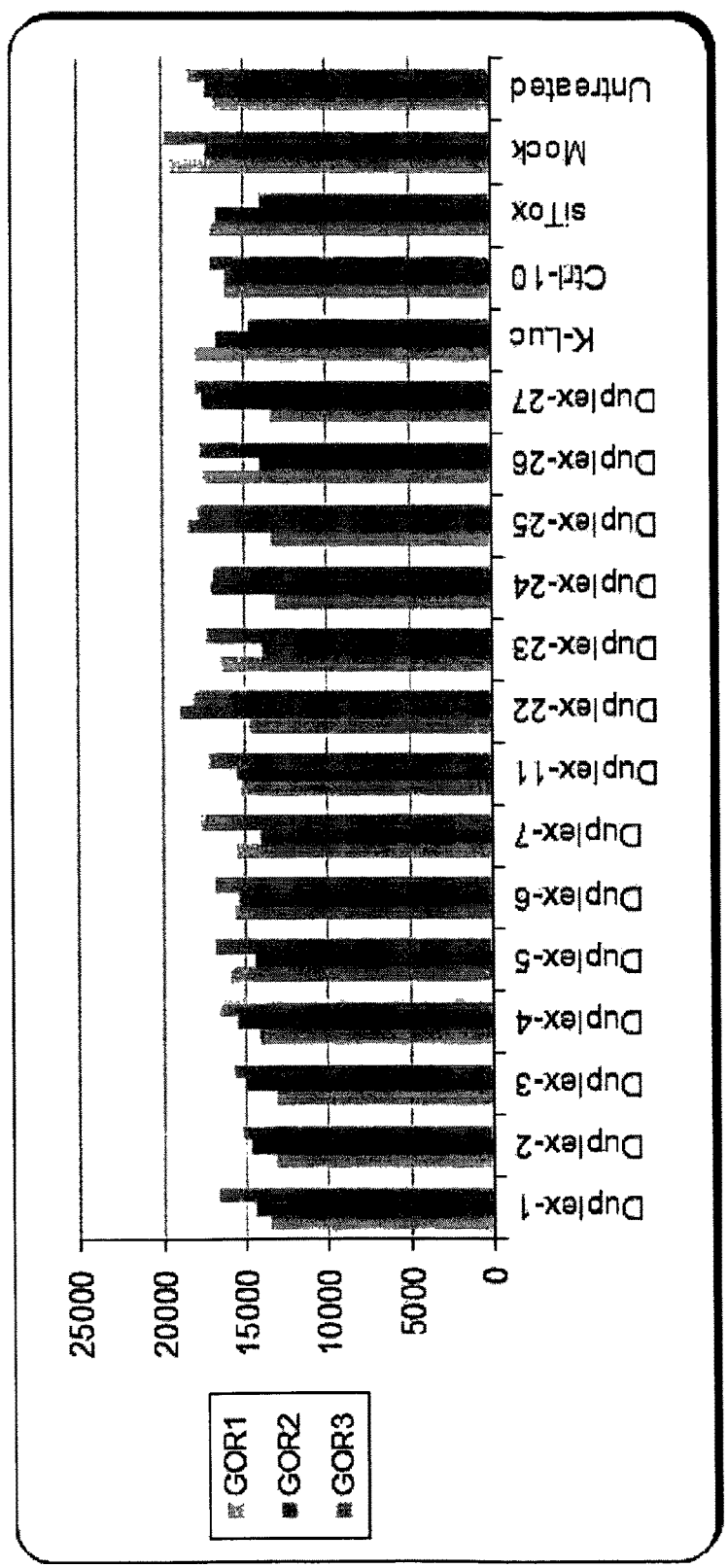
FIG. 6 shows the levels of GAPDH mRNA expression, a marker of cell health. The similarity of the expression levels for those cells treated with derivatized siRNA to that of the mock and untreated cells is an indication of the lack of cellular toxicity at the treatment concentration and duration.

The efficacy of siRNA knock-down was measured with a Branched DNA Assay as reported by the vendor; the results of such knockdown are shown in FIG. 5. The relative cell viability was assessed by the absolute expression of GAPDH in the same well (FIG. 6).

Unless stated to the contrary, all compounds in the examples were prepared and characterized as described. All patents and publications cited herein are hereby incorporated by reference in their entirety.

The invention claimed is:

1. A compound of formula I:

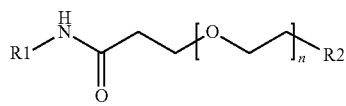

or a pharmaceutically acceptable salt or ester thereof, wherein n is 1-24 and wherein:

R1 is selected from the group consisting of:

a compound of the formula:

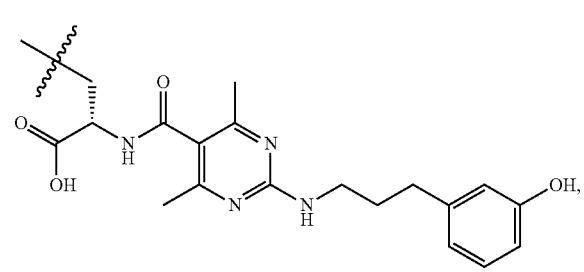 [SMILES: *C[C@H](NC(=O)c1c(C)nc(NCCCc2cccc(O)c2)nc1C)C(=O)O]

a compound of formula:

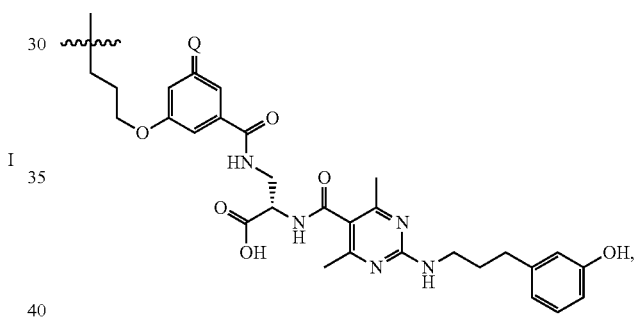

a compound of the formula:

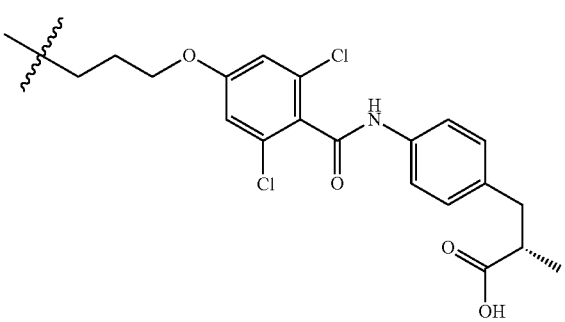

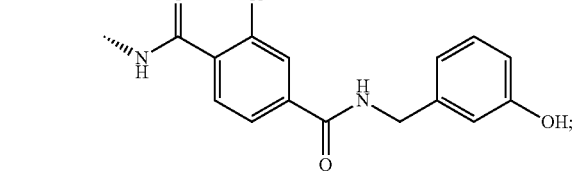

and
a compound of the formula:

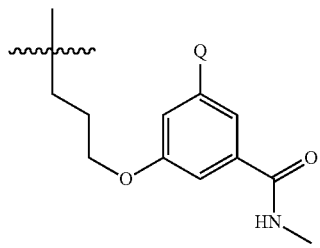

wherein Q is H or OH;
R2 is selected from the group consisting of:
a compound of the formula:

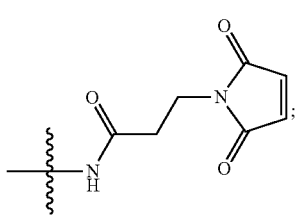 [SMILES: *NC(=O)CCN1C(=O)C=CC1=O]

a compound of the formula:

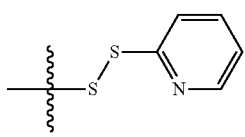 [SMILES: *SSc1ccccn1]

a compound of the formula:

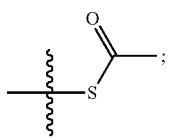 [SMILES: *SC(C)=O]

and
a compound of the formula:

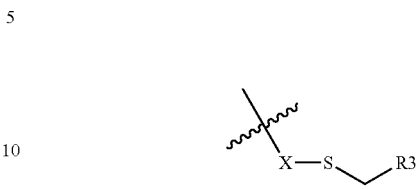

wherein R3 is a conjugated moiety and X represents either sulfur or a compound of the formula:

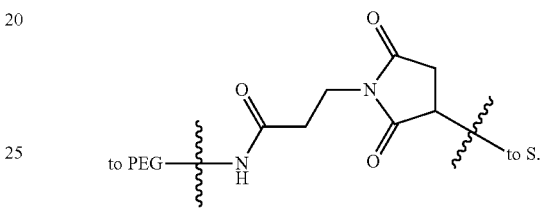

2. A compound according to claim 1, wherein R1 is a compound of the formula:

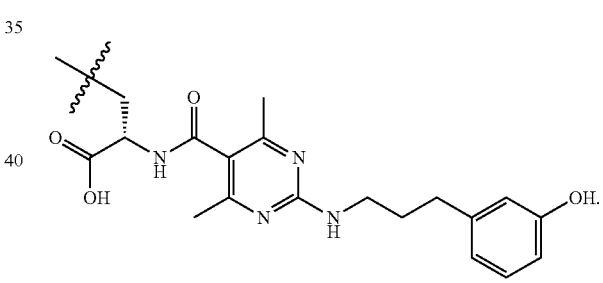

3. A compound according to claim 1, wherein R1 is a compound of the formula:

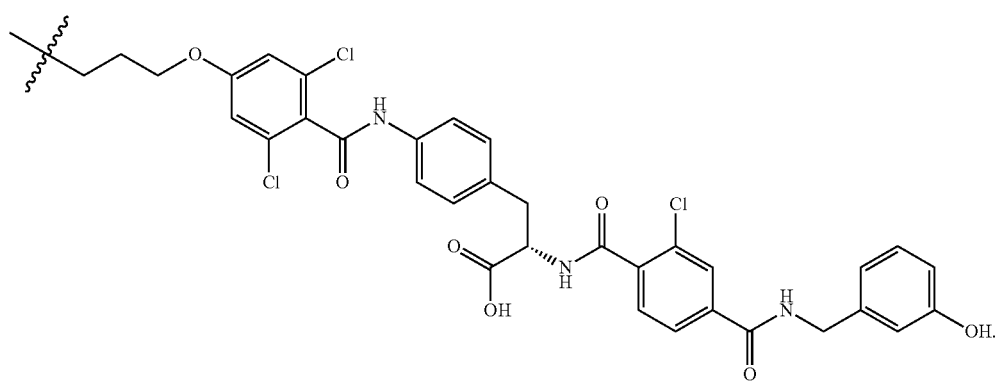 [SMILES: *CCCOc1cc(Cl)c(C(=O)Nc2ccc(C[C@H](NC(=O)c3ccc(C(=O)NCc4cccc(O)c4)cc3Cl)C(=O)O)cc2)c(Cl)c1]

4. A compound according to claim 1, wherein R1 is a compound of the formula:

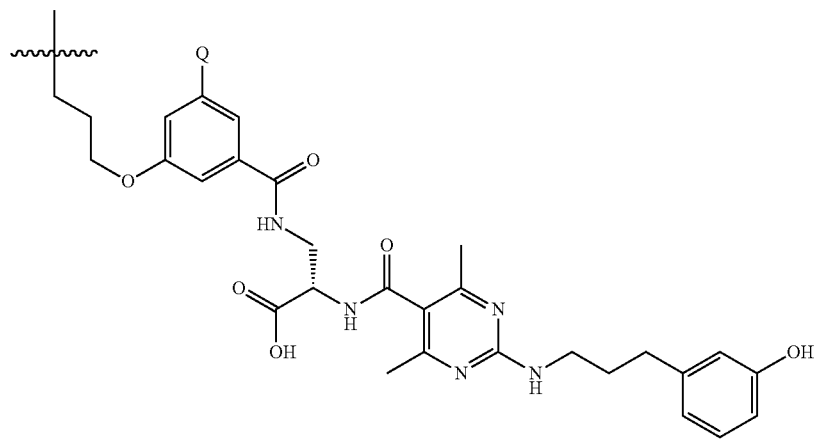

wherein Q is H or OH.

5. A compound according to claim 4, wherein Q is H.

6. A compound according to claim 4, wherein Q is OH.

7. A compound according to claim 1, wherein R2 is a compound of the formula:

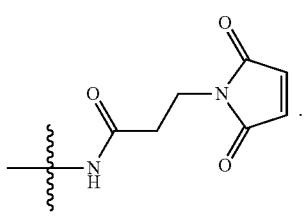 [SMILES: *NC(=O)CCN1C(=O)C=CC1=O]

8. A compound according to claim 2, wherein R2 is a compound of the formula:

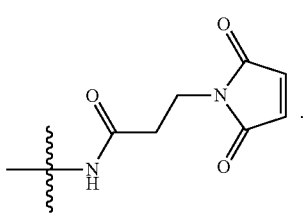 [SMILES: *NC(=O)CCN1C(=O)C=CC1=O]

9. A compound according to claim 3, wherein R2 is a compound of the formula:

10. A compound according to claim 4, wherein R2 is a compound of the formula:

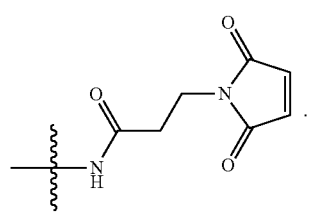 [SMILES: *NC(=O)CCN1C(=O)C=CC1=O]

11. A compound according to claim 5, wherein R2 is a compound of the formula:

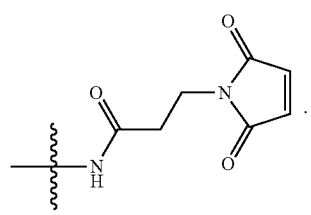 [SMILES: *NC(=O)CCN1C(=O)C=CC1=O]

12. A compound according to claim 6, wherein R2 is a compound of the formula:

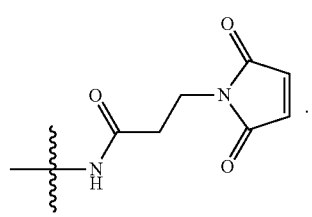 [SMILES: *NC(=O)CCN1C(=O)C=CC1=O]

13. A compound according to claim 7, wherein R2 is a compound of the formula:

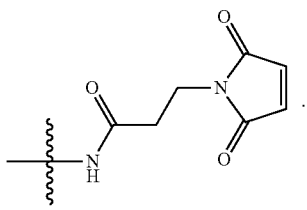 [SMILES: *NC(=O)CCN1C(=O)C=CC1=O]

14. A compound according to claim 1, wherein R2 is a compound of the formula:

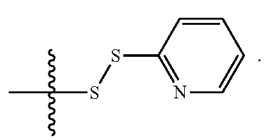 [SMILES: *SSc1ccccn1]

15. A compound according to claim 2, wherein R2 is a compound of the formula:

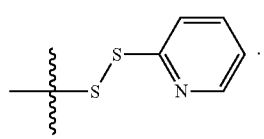 [SMILES: *SSc1ccccn1]

16. A compound according to claim 3, wherein R2 is a compound of the formula:

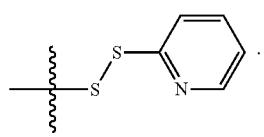 [SMILES: *SSc1ccccn1]

17. A compound according to claim 4, wherein R2 is a compound of the formula:

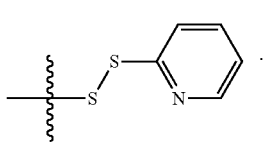

18. A compound according to claim 5, wherein R2 is a compound of the formula:

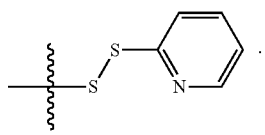

19. A compound according to claim 6, wherein R2 is a compound of the formula:

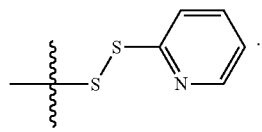

20. A compound according to claim 7, wherein R2 is a compound of the formula:

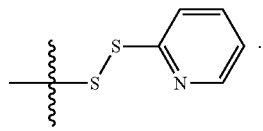 [SMILES: *SSc1ccccn1]

21. A compound according to claim 1, wherein R2 is a compound of the formula:

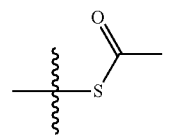

22. A compound according to claim 2, wherein R2 is a compound of the formula:

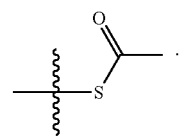 [SMILES: *SC(C)=O]

23. A compound according to claim 3, wherein R2 is a compound of the formula:

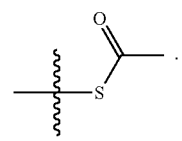 [SMILES: *SC(C)=O]

24. A compound according to claim 4, wherein R2 is a compound of the formula:

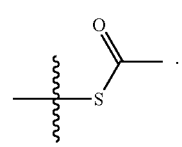 [SMILES: *SC(C)=O]

25. A compound according to claim 5, wherein R2 is a compound of the formula:

26. A compound according to claim 6, wherein R2 is a compound of the formula:

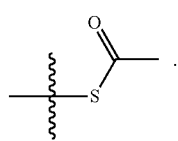 [SMILES: *SC(C)=O]

27. A compound according to claim 7, wherein R2 is a compound of the formula:

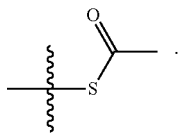 [SMILES: *SC(C)=O]

28. A compound according to claim 1, wherein R2 is a compound of the formula:

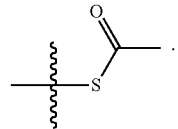

wherein R3 is a single or double stranded oligonucleotide and X represents either sulfur or a compound of the formula:

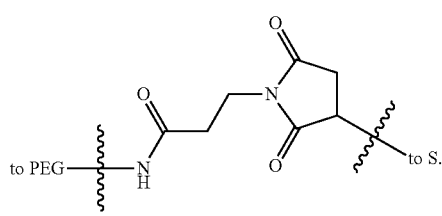

29. A compound according to claim 2, wherein R2 is a compound of the formula:

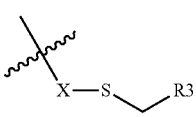

wherein R3 is a single or double stranded oligonucleotide and X represents either sulfur or a compound of the formula:

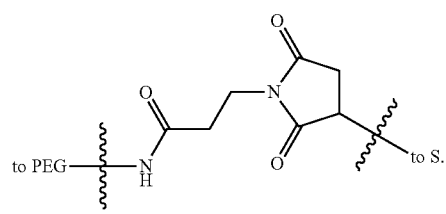

30. A compound according to claim 3, wherein R2 is a compound of the formula:

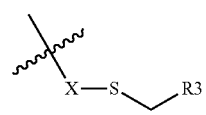

wherein R3 is a single or double stranded oligonucleotide and X represents either sulfur or a compound of the formula:

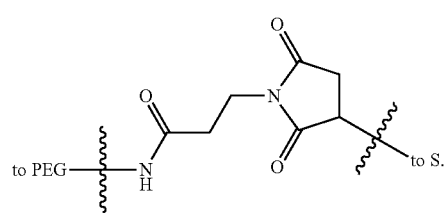

31. A compound according to claim 4, wherein R2 is a compound of the formula:

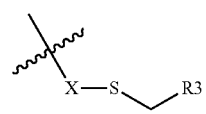

wherein R3 is a single or double stranded oligonucleotide and X represents either sulfur or a compound of the formula:

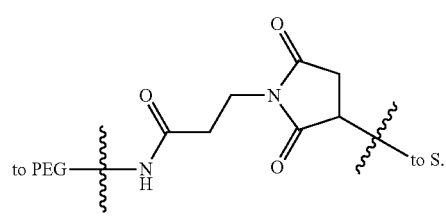

32. A compound according to claim 5, wherein R2 is a compound of the formula:

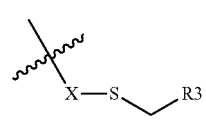

wherein R3 is a single or double stranded oligonucleotide and X represents either sulfur or a compound of the formula:

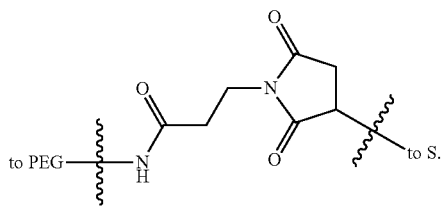

33. A compound according to claim 6, wherein R2 is a compound of the formula:

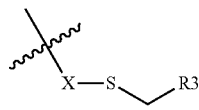

wherein R3 is a single or double stranded oligonucleotide and X represents either sulfur or a compound of the formula:

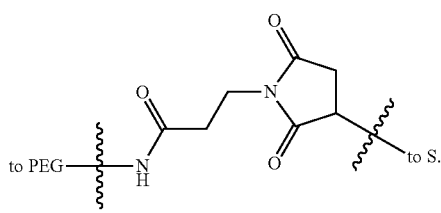

34. A compound according to claim 7, wherein R2 is a compound of the formula:

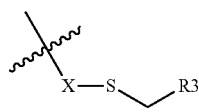

wherein R3 is a single or double stranded oligonucleotide and X represents either sulfur or a compound of the formula:

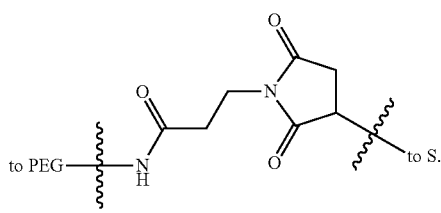

35. A compound according to claim 28, wherein X represents sulfur.

36. A compound according to claim 29, wherein X represents sulfur.

37. A compound according to claim 30, wherein X represents sulfur.

38. A compound according to claim 31, wherein X represents sulfur.

39. A compound according to claim 32, wherein X represents sulfur.

40. A compound according to claim 33, wherein X represents sulfur.

41. A compound according to claim 34, wherein X represents sulfur.

42. A compound according to claim 28, wherein R3 is a siRNA molecule.

43. A compound according to claim 29, wherein R3 is a siRNA molecule.

44. A compound according to claim 30, wherein R3 is a siRNA molecule.

45. A compound according to claim 31, wherein R3 is a siRNA molecule.

46. A compound according to claim 32, wherein R3 is a siRNA molecule.

47. A compound according to claim 33, wherein R3 is a siRNA molecule.

48. A compound according to claim 34, wherein R3 is a siRNA molecule.

49. A compound according to claim 35, wherein R3 is a siRNA molecule.

50. A compound according to claim 36, wherein R3 is a siRNA molecule.

51. A compound according to claim 37, wherein R3 is a siRNA molecule.

52. A compound according to claim 38, wherein R3 is a siRNA molecule.

53. A compound according to claim 39, wherein R3 is a siRNA molecule.

54. A compound according to claim 40, wherein R3 is a siRNA molecule.

55. A compound according to claim 41, wherein R3 is a siRNA molecule.

56. A compound according to claim 21, wherein R1 is a compound of the formula:

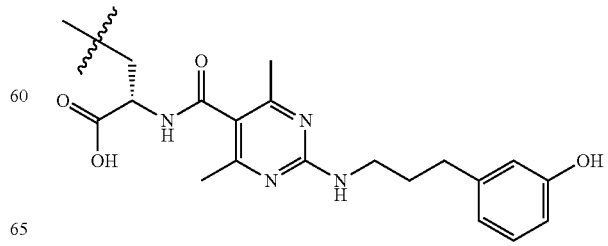

or a compound of the formula:

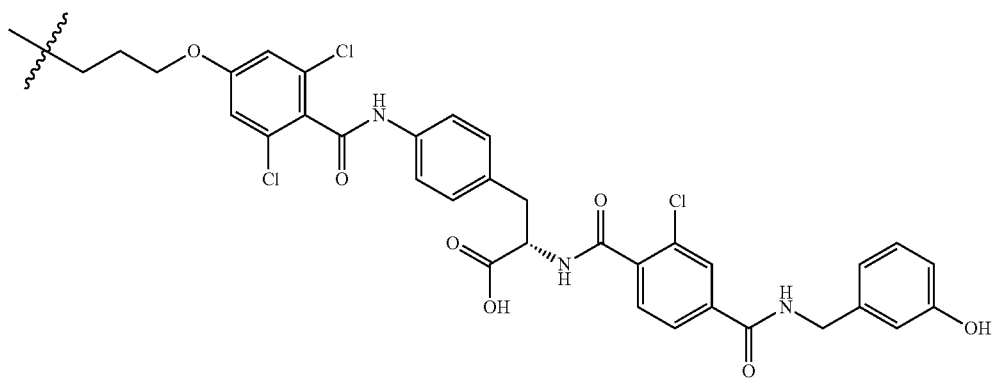 [SMILES: *CCCOc1cc(Cl)c(C(=O)Nc2ccc(C[C@H](NC(=O)c3ccc(C(=O)NCc4cccc(O)c4)cc3Cl)C(=O)O)cc2)c(Cl)c1]

or a compound of the formula:

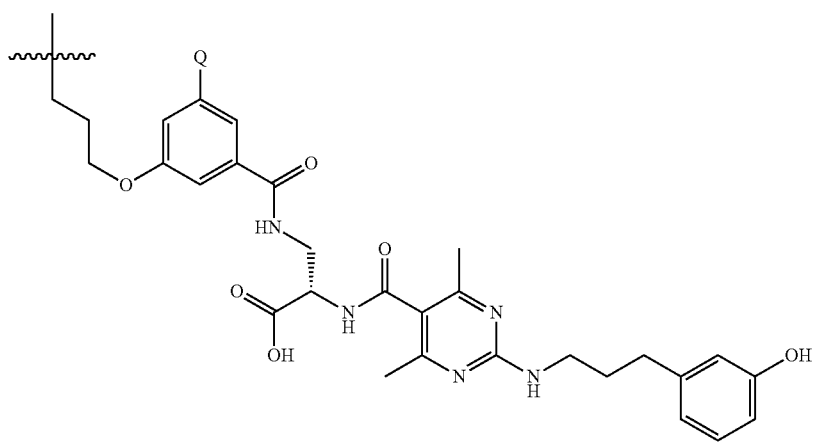

wherein Q is H or OH.

57. A compound according to claim 1, selected from the group consisting of:
(S)-3-{3-{2-[2-(2-{2-[3-(2,5-Dioxo-2,5-dihydro-pyrrol-1-yl)-propionylamino]-ethoxy]-ethoxy}-ethoxy)-ethoxy]-propionylamino}-2-({2-[3-(3-hydroxy-phenyl)-propylamino]-4,6-dimethyl-pyrimidine-5-carbonyl}amino)propionic acid; and
(S)-3-{3-(2-{2-[2-(2-{2-[2-(2-{2-[3-(2,5-Dioxo-2,5-dihydro-pyrrol-1-yl)-propionylamino]-ethoxy)-ethoxy]-ethoxy-ethoxy)-ethoxy]-ethoxy}-ethoxy)-ethoxy]-propionylamino-2-({2-[3-(3-hydroxy-phenyl)-propylamino]-4,6-dimethyl-pyrimidine-5-carbonyl}amino)propionic acid.

58. A compound according to claim 1, selected from the group consisting of:
(S)-3-{3-[2-(2-2-[2-(2-{2-[2-(2-{2-[2-(2-{2-[3-(2,5-Dioxo-2,5-dihydro-pyrrol-1-yl)-propionylamino]-ethoxy-ethoxy)-ethoxy]-ethoxy-ethoxy)-ethoxy]-ethoxy}-ethoxy)-ethoxy]-ethoxy-ethoxy)-ethoxy]-propionylamino}-2-({2-[3-(3-hydroxy-phenyl)-propylamino]-4,6-dimethyl-pyrimidine-5-carbonyl}amino)propionic acid; and
(S)-3-4-[4-(3-(2-{2-[2-(2-{2-[2-(2-{2-ethoxy)-ethoxy]-ethoxy}-ethoxy)-ethoxy]-ethoxy}-ethoxy)-ethoxy]-amino-propoxy)-2,6-dichloro-benzoylamino]-phenyl}-2-[2-chloro-4-(3-hydroxy-benzylcarbamoyl)-benzoyl amino]-propionic acid-PEGS.

59. A compound according to claim 1, selected from the group consisting of:
S)-2-[2-Chloro-4-(3-hydroxy-benzylcarbamoyl)-benzoylamino]-3-(4-{2,6-dichloro-4-[3-(3-{2-[2-(2-{2-[3-(2,5-dioxo-2,5-dihydro-pyrrol-1-yl)-propionylamino]-ethoxy}-ethoxy)-ethoxy]-ethoxy}-propionylamino)-propoxy]-benzoylamino}-phenyl)-propionic acid; and
S)-2-[2-Chloro-4-(3-hydroxy-benzylcarbamoyl)-benzoylamino]-3-(4-{2,6-dichloro-4-(3-(3-{2-[2-(2-{2-2-[2-(2-{2-2-[2-(2-{2-[3-(2,5-dioxo-2,5-dihydro-pyrrol-1-yl)-propionylamino]-ethoxy}-ethoxy)-ethoxy]-ethoxy}-ethoxy}-ethoxy)-ethoxy]-ethoxy-propionylamino)-propoxy]-benzoylamino-phenyl)-propionic acid.

60. A compound according to claim 1, selected from the group consisting of:
S)-2-[2-Chloro-4-(3-hydroxy-benzylcarbamoyl)-benzoylamino]-3-(4-{2,6-dichloro-4-[3-(3-{2-[2-(2-{2-2-[2-(2-{2-[3-(2,5-dioxo-2,5-dihydro-pyrrol-1-yl)-propionylamino]-ethoxy}-ethoxy)-ethoxy]-ethoxy]-ethoxy}-ethoxy)-ethoxy]-ethoxy}-propionylamino)-propoxy]-benzoylamino}-phenyl)-propionic acid; and
(S)-3-{[(3-{3-[3-(2-{2-[2-(2-{2-[2-(2-{2-(2-{2-3-(2,5-Dioxo-2,5-dihydro-pyrrol-1-yl)-propionylamino]-ethoxyethoxy)-ethoxy]-ethoxy-ethoxy)-ethoxy]-ethoxy-
ethoxy)-propionylamino]-propyl-oxy}-phenyl)-
carbonyl]-amino}-2-({2-[3-(3-hydroxy-phenyl)-
propylamino]-4,6-dimethyl-pyrimidine-5-carbonyl}-
amino)-propionic acid.

61. A compound according to claim 1, selected from the group consisting of:

(S)-3-{[(3-{3-[3-(2-{2-[2-(2-{2-[2-(2-{2-[3-(2,5-Dioxo-2,5-dihydro-pyrrol-1-yl)-propionylamino]-ethoxy-ethoxy)-ethoxy]-ethoxy-ethoxy)-ethoxy]-ethoxy-ethoxy)-propionylamino]-propyl-oxy 1-5-hydroxy-phenyl)-carbonyl]-amino}-2-({2-[3-(3-hydroxy-phenyl)-propylamino]-4,6-dimethyl-pyrimidine-5-carbonyl}-amino)-propionic acid; and (S)-3-[({3-[3-(3-{2-[2-(2-}2-[3-(2,5-Dioxo-2,5-dihydro-pyrrol-1-yl)-propionylamino]-ethoxy}-ethoxy)-ethoxy]-ethoxy}-propionylamino)-propyl-oxy]-5-hydroxy-phenyl}-carbonyl)-amino]-2-({2-[3-(3-hydroxy-phenyl)-propylamino]-4,6-dimethyl-pyrimidine-5-carbonyl}-amino)-propionic acid.

62. A pharmaceutical composition comprising a compound according to claim 1 and a pharmaceutically acceptable carrier.

\* \* \* \* \*